United States Patent
Giovenzana et al.

(10) Patent No.: US 7,893,223 B2
(45) Date of Patent: *Feb. 22, 2011

(54) MULTIDENTATE AZA LIGANDS ABLE TO COMPLEX METAL IONS AND THE USE THEREOF IN DIAGNOSTICS AND THERAPY

(75) Inventors: Giovanni Battista Giovenzana, Milan (IT); Giovanni Palmisano, Milan (IT); Massimo Sisti, Milan (IT); Camilla Cavallotti, Milan (IT); Silvio Aime, Milan (IT); Luisella Calabi, Milan (IT); Rolf Swenson, Princeton, NJ (US); Ramalingam Kondareddiar, Dayton, NJ (US); Luciano Lattuada, Milan (IT); Pierfrancesco Morosini, Milan (IT)

(73) Assignee: Bracco Imaging S.p.A., Milan (IT)

( * ) Notice: Subject to any disclaimer, the term of this patent is extended or adjusted under 35 U.S.C. 154(b) by 1275 days.

This patent is subject to a terminal disclaimer.

(21) Appl. No.: 11/165,793

(22) Filed: Jun. 24, 2005

(65) Prior Publication Data

US 2006/0034773 A1    Feb. 16, 2006

Related U.S. Application Data

(63) Continuation-in-part of application No. 10/484,111, filed as application No. PCT/EP02/07658 on Jul. 10, 2002, now Pat. No. 7,186,400.

(30) Foreign Application Priority Data

Jul. 17, 2001    (IT)    .......................... MI2001A1518

(51) Int. Cl.
   *C07F 13/00*    (2006.01)
(52) U.S. Cl. .............................. 534/14; 534/10; 534/15; 424/1.11; 424/1.65
(58) Field of Classification Search ................ 424/1.11, 424/1.49, 1.65, 1.69, 1.73, 1, 81, 1.85, 1.89, 424/9.1, 9.3, 9.4, 9.5, 9.6, 9.7, 9.8, 9.36, 424/9.361; 534/7, 10–16; 540/450
See application file for complete search history.

(56) References Cited

U.S. PATENT DOCUMENTS

| 3,107,260 | A | * | 10/1963 | Knell | ............................... | 71/1 |
| 6,193,950 | B1 | * | 2/2001 | Platzek et al. | ............... | 424/9.36 |
| 6,403,055 | B1 | | 6/2002 | Calabi et al. | | |
| 7,186,400 | B2 | * | 3/2007 | Giovenzana et al. | ....... | 424/9.36 |

FOREIGN PATENT DOCUMENTS

| GB | 926351 A | 5/1963 |
| WO | 92/09283 A1 | 6/1992 |
| WO | 98/05625 A1 | 2/1998 |

OTHER PUBLICATIONS

Caravan P. et al; "Gadolinium(III) Chelates as MRI Contrast Agents: Structure, Dynamics, and Applications", Chem. Rev., 19999, published on Web Aug. 20, 1999, pp. 2293-2352, EPIX Medical, Inc., Cambridge, Massachusetts.

* cited by examiner

*Primary Examiner*—D L Jones
(74) *Attorney, Agent, or Firm*—M. Caragh Noone

(57) ABSTRACT

Compounds of general formula (I):

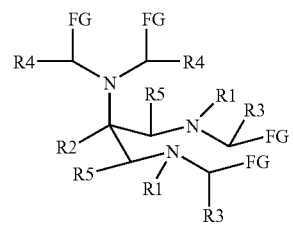

with substituents as defined herein and their chelates with bi-trivalent ions of the metal elements of atomic numbers 20 to 31, 39, 42, 43, 44, 49, and 57 to 83, and radioisotopes chosen among $^{203}$Pb, $^{67}$Ga, $^{68}$Ga, $^{72}$As, $^{111}$In, $^{113}$In, $^{90}$Y, $^{97}$Ru, $^{62}$Cu, $^{64}$Cu, $^{52}$Fe, $^{52m}$Mn, $^{140}$La, $^{175}$Yb, $^{153}$Sm, $^{166}$Ho, $^{149}$Pm, $^{177}$Lu, $^{142}$Pr, $^{159}$Gd, $^{212}$Bi, $^{47}$Sc, $^{149}$Pm, $^{67}$Cu, $^{111}$Ag, $^{199}$Au, $^{161}$Tb, $^{51}$Cr, $^{167}$Tm, $^{141}$Ce, $^{168}$Yb, $^{88}$Y, $^{165}$Dy, $^{166}$Dy, $^{97}$Ru, $^{103}$Ru, $^{186}$Re, $^{99m}$Tc, $^{211}$Bi, $^{213}$Bi, $^{214}$Bi, $^{105}$Rh, $^{109}$Pd, $^{177m}$Sn, $^{177}$Sn and $^{199}$Au, as well as the salts thereof with physiologically compatible bases or acids.

60 Claims, 2 Drawing Sheets

MULTIDENTATE AZA LIGANDS ABLE TO COMPLEX METAL IONS AND THE USE THEREOF IN DIAGNOSTICS AND THERAPY

This application is a continuation-in-part of and claims priority from U.S. Ser. No. 10/484,111, filed Jan. 15, 2004 now U.S. Pat. No. 7,186,400, which a national stage application for International Application No. PCT/EP02/07658, filed Jul. 10, 2002, pending, which claims priority from Italian Application No. MI2001 A001518, filed Jul. 17, 2001, pending, which are all incorporated by reference herein in their entirety.

The present invention relates to novel aza ligands able to complex metal ions, in particular paramagnetic ions, and the use of the corresponding complexes as contrast agents for magnetic resonance imaging (MRI).

A number of complexes of paramagnetic metal ions with cyclic and acyclic aza ligands are known as contrast agents in the MRI diagnostic technique (see for instance: The Chemistry of Contrast Agents in Medical Magnetic Resonance Imaging, Merbach A. E. and Toth E. Eds., John Wiley and sons, Chichester, 2001; Caravan P. et al. Chem. Rev. 1999, 99, 2293-2352 and U.S. Pat. No. 4,885,363; U.S. Pat. No. 4,916,246; U.S. Pat. No. 5,132,409; U.S. Pat. No. 6,149,890). Some of these complexes (Gd-DTPA, Gd-DOTA, Gd-HPDO3A, and the like) have recently been marketed.

The paramagnetic metal ions most extensively used in MRI diagnostics are either in the transitions metals and in the Lanthanide series. As far as Lanthanides are concerned, the attention is essentially focused on Gd(III) ion both for its high paramagnets (7 unpaired electrons) and for its favourable properties in terms of electronic relaxation. This metal does not possess any physiological function in mammalians, and its administration as free ion is strongly toxic even at low doses (10-20 micromol/Kg). For this reason, it is necessary to use ligands that form chelates with the lanthanide ion endowed with high thermodynamic and kinetic stability. This means that the chelating ligand should exhibit a high level of affinity and selectivity for the relevant paramagnetic ions as opposed to the physiological ions. Moreover, the ligand should show suitable pharmacokinetic properties (excretion, binding to plasma proteins, metabolical inertia, and the like), and optimal relaxivity properties, that is to say that the values of this parameter should be and remain high, independently of the surrounding environment, in particular the presence of physiological anions and pH changes.

A novel class of ligands has now been found, which form complexes having particularly favorable characteristics, above all in terms of stability and relaxivity.

Relaxivity ($r_{1p}$) is an intrinsic property of paramagnetic complexes which characterizes their ability to increase the nuclear magnetic relaxation rate of vicinal protons. High relaxation rates ensure increased contrast in the image, which makes it possible to obtain physiological information in a short amount of time with obvious advantages in terms of both image quality and economic cost.

The relaxivity of a Gd(III) complex is a property directly related to the number (q) of water molecules of the inner coordination sphere of the metal ion. As said before, contrast agents for magnetic resonance imaging (MRI) are mostly represented by stable complexes of Gd(III) ions the large majority of which are based on octadentate ligands to ensure a high thermodynamic stability. This choice has however implied that only one water molecule may enter in the inner coordination sphere of the Gd(III) ion which has a coordination number of nine (The Chemistry of Contrast Agents in Medical Magnetic Resonance Imaging, Merbach A. E. and Toth E. Eds., John Wiley and sons, Chichester, 2001).

A further contribution to the observed relaxation rate (of the water protons in an aqueous solution containing a paramagnetic complex) derives from the exchange between the molecule(s) of coordinated water and the molecules of the remaining solvent. In particular, the increase of the observed relaxation rate is inversely related to the residence time ($t_M$) of the protons of the water molecule(s) which are coordinated to the paramagnetic center the inner coordination sphere. Higher relaxivity is obtained at fast exchange conditions.

The ligands of the invention forms complexes whose high starting relaxivity is consistent with the presence of two water molecules in the inner coordination sphere and with simultaneous favorable $t_M$ values.

The ligands of the invention have the following general formula (I):

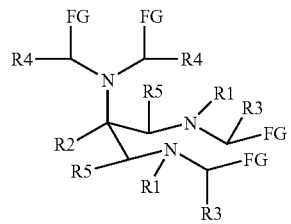

in which:

$R_1$ is hydrogen, $C_1$-$C_{20}$ alkyl optionally substituted with one or more carboxy groups, $C_3$-$C_{10}$ cycloalkyl, $C_4$-$C_{20}$ cycloalkylalkyl, aryl, arylalkyl or the two $R_1$ groups, taken together, form a straight or cyclic $C_2$-$C_{10}$ alkylene group or an ortho-disubstituted arylene;

$R_2$ is hydrogen, carboxy, or an optionally substituted group selected from $C_1$-$C_{20}$ alkyl, $C_3$-$C_{10}$ cycloalkyl, $C_4$-$C_{20}$ cycloalkylalkyl, aryl, arylalkyl, a group bearing an acidic moiety, and a group bearing an amino moiety, each of which may be further optionally substituted with functional groups which allow conjugation with a suitable molecule able to interact with physiological systems;

$R_3$, $R_4$ and $R_5$, which can be the same or different, are hydrogen, carboxy, or an optionally substituted group selected from $C_1$-$C_{20}$ alkyl, $C_3$-$C_{10}$ cycloalkyl, $C_4$-$C_{20}$ cycloalkylalkyl, aryl, arylalkyl, a group bearing an acidic moiety and a group bearing an amino moiety, each of which may be further optionally substituted with functional groups which allow conjugation with a suitable molecule able to interact with physiological systems;

FG, which can be the same or different, are carboxy, —$PO_3H_2$ or —RP(O)OH groups, wherein R is hydrogen, or an optionally substituted group selected from $C_1$-$C_{20}$ alkyl, $C_3$-$C_{10}$ cycloalkyl, $C_4$-$C_{20}$ cycloalkylalkyl, aryl, arylalkyl, a group bearing an acidic moiety and a group bearing an amino moiety, each of which may be further, optionally substituted with functional groups which allow conjugation with a suitable molecule able to interact with physiological systems.

Substituents within the definitions above are known to those skilled in the art and are illustrated by the compounds of the invention set forth in the Examples.

Figure 1:
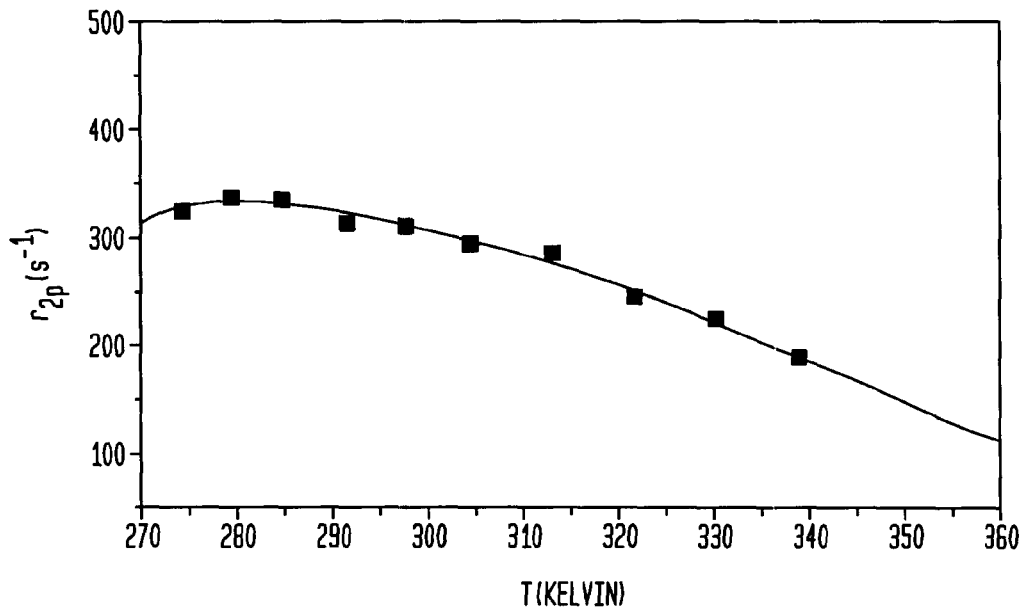
FIG. 1 is a measurement of the transverse water $^{17}$O NMR relaxation time of the Gd(III) complex of EXAMPLE 1 at variable temperature.

The above compounds can have one or more acids (or group bearing acidic moieties) or amines (or group bearing amino moieties). Thus, it is understood and within the scope of this invention that one or more of these groups may be protected by one or more protecting groups.

When an acid or amine is "protected", this means that the group is in modified form to preclude undesired side reactions at the protected site. Suitable protecting groups for the compounds of the present invention will be recognized from the present application taking into account the level of skill in the art, and with reference to standard textbooks, such as Greene et al., *Protective Groups in Organic Synthesis* (New York: Wiley, 1991).

Examples of protecting groups include tert-butyl, t-butyloxycarbonyl (Boc), benzyloxycarbonyl (Cbz), Fluorenylmethoxycarbonyl (Fmoc) and trichloroethoxycarbonyl (Troc) as carboxyl protecting groups and tetrachloro-phthaloyl (TCP), phthaloyl, pipecolinic acid (Pic-OH), Boc, COCF$_3$ and Cbz as amine protecting groups. Again, protecting groups are well known in the art and this list is not meant to be limiting on the scope of the invention. Any suitable protecting group is understood to be within the scope of the present inventions.

Functional groups which allow conjugation with targeting molecules or other molecules that are able to interact with physiological systems are known to those skilled in the art. Such groups include, for example, carboxylic acids, amines, aldehydes, alkyl halogens, alkyl maleimdes, sulfhydryl groups, hydroxyl groups, etc. Carboxylic acids and amines are particularly preferred. The invention further relates to the chelates of compounds of formula (I) with paramagnetic or radioactive metal ions, in particular with the bi-trivalent ions of the metal elements having atomic number ranging between 20 and 31, 39, 42, 43, 44, 49, and between 57 and 83, as well as the salts thereof with physiologically compatible bases or acids.

Particularly preferred for the diagnostic use as MRI contrast agents, are the complexes with paramagnetic ions such as Fe($^{2+}$), Fe($^{3+}$), Cu($^{2+}$), Cr($3+$), Gd($^{3+}$), Eu($^{3+}$), Dy($^{3+}$), La($^{3+}$), Yb($^{3+}$), Mn($^{2+}$), Mn($^{3+}$), Co($^{2+}$), Ni($^{2+}$), Pr($^{3+}$), Nd($^{3+}$), Sm($^{3+}$), Gd($^{3+}$), Tb($^{3+}$), Ho($^{3+}$) and Er($^{3+}$), and in particular gadolinium complexes.

On the other hand, for uses in radiotherapy or radiodiagnostics, preferred complexes are those with $^{203}$Pb, $^{67}$Ga, $^{68}$Ga, $^{72}$As, $^{111}$In, $^{113}$In, $^{90}$Y, $^{97}$Ru, $^{62}$Cu, $^{64}$Cu, $^{52}$Fe, $^{52m}$Mn, $^{140}$La, $^{175}$Yb, $^{153}$Sm, $^{166}$Ho, $^{149}$Pm, $^{177}$Lu, $^{142}$Pr, $^{159}$Gd, $^{212}$Bi, $^{47}$Sc, $^{149}$Pm, $^{67}$Cu, $^{111}$Ag, $^{199}$Au, $^{161}$Tb, $^{51}$Cr, $^{167}$Tm, $^{141}$Ce, $^{168}$Yb, $^{88}$Y, $^{165}$Dy, $^{166}$Dy, $^{97}$Ru, $^{103}$Ru, $^{186}$Re, $^{99m}$Tc, $^{211}$Bi, $^{213}$Bi, $^{214}$Bi, $^{105}$Rh, $^{109}$Pd, $^{117m}$Sn, $^{177}$Sn and $^{199}$Au and oxides and nitrides thereof. The choice of metal will be determined based on the desired therapeutic or diagnostic application For example, for diagnostic purposes (e.g., to diagnose and monitor therapeutic progress in e.g., primary tumors and metastases), the preferred radionuclides include $^{64}$Cu, $^{67}$Ga, and $^{111}$In, with $^{111}$In being especially preferred. For therapeutic purposes (e.g., to provide radiotherapy for primary tumors and metastasis related to cancers of the prostate, breast, lung, etc.), the preferred radionuclides include $^{64}$Cu, $^{90}$Y, $^{105}$Rh, $^{111}$In, $^{117m}$Sn, $^{149}$Pm, $^{153}$Sm, $^{161}$Tb, $^{166}$Dy, $^{166}$Ho, $^{175}$Yb, $^{177}$Lu, $^{186/188}$Re, and $^{199}$Au, with $^{177}$Lu and $^{90}$Y being particularly preferred.

The chelates of the invention can also be in the form of salts, when the ligand has salifiable functions.

Preferred cations of inorganic bases which can be suitably used to salify the complexes of the invention comprise ions of alkali or alkaline-earth metals such as potassium, sodium, calcium, magnesium.

Preferred cations of organic bases comprise, inter alia, those of primary, secondary and tertiary amines such as ethanolamine, diethanolamine, morpholine, glucamine, N-methylglucamine, N,N-dimethylglucamine.

Preferred anions of inorganic acids which can be suitably used to salify the complexes of the invention comprise the ions of halo acids such as chlorides, bromides, iodides or other ions such as sulfate.

Preferred anions of organic acids comprise those of acids routinely used in pharmaceutical technique for the salification of basic substances, such as acetate, succinate, citrate, fumarate, maleate, oxalate.

Preferred cations and anions of amino acids comprise, for example, those of taurine, glycine, lysine, arginine or ornithine or of aspartic and glutamic acids.

The $C_1$-$C_{20}$ alkyl group is a straight or branched group and preferably is a $C_1$-$C_6$ group, more preferably methyl, ethyl, propyl, isopropyl.

The $C_3$-$C_{10}$ cycloalkyl group is preferably a cyclopropyl, cyclopentyl or cyclohexyl group, optionally in turn substituted at one of the position of the ring, by an alkyl group as defined above.

The $C_4$-$C_{20}$ cycloalkylalkyl group is preferably cyclopropylmethyl, cyclohexylethyl, cyclohexylmethyl, cyclopentylmethyl, cyclopentylethyl.

Aryl is preferably phenyl or phenyl substituted with one to five substituents, which can be the same or different, selected from hydroxy, $C_1$-$C_2$ alkoxy, halogen, cyano, nitro, methyl, ethyl, carboxy, amino, $C_1$-$C_2$ alkyl- or dialkylamino, or alkyl groups variously substituted with one to three substituents such as hydroxy, $C_1$-$C_2$ alkoxy, halogen, cyano, nitro, methyl, ethyl, carboxy, amino, $C_1$-$C_2$ alkyl- or dialkylamino.

Ortho-disubstituted arylene is preferably optionally substituted 1,2-phenylene as indicated above.

$C_1$-$C_{20}$ Alkyl substituted with carboxy groups is preferably carboxymethyl.

FG is preferably a carboxy group.

$R_2$ is preferably methyl, alkyl as defined above, aryl or arylalkyl, all optionally substituted with functional groups such as optionally protected carboxy, amino, formyl, hydroxy or mercapto, which can be used as conjugation sites with other compounds without interfering with the structural integrity of the molecule.

$R_3$ is preferably hydrogen.

$R_4$ is preferably hydrogen or methyl.

$R_5$ is preferably hydrogen.

Preferred compounds of formula (I) are those in which the two $R_1$ groups form together an alkylene, in particular ethylene or propylene, preferably ethylene, or a cyclic alkylene and the other groups are as defined for the general formula (I) or have the preferred meanings indicated above.

In an alternative embodiment, two compounds of formula (I) can form a dimer with each other through their $R_2$ substituents. One example of this type of compound is shown in Example 10 below.

The preparation of dimers can be prepared by direct linking of two compounds of formula (I) via $R_2$ as in example 10 or by amide bond formation of an alkyl carboxyl or alkyl amine group at $R_2$ to a corresponding diamine or diacid. This approach can be generalized to prepare multimers by having a polyamine or polyacid for the attachment of the alkyl acid or alkyl amine of $R_2$. It is understood by those in the field that the amide bond formation step to prepare dimers or multimers from compounds of formula (I) can be substituted by alkylation, acylation, esterification, or reductive amination methods. The polyamine or polyacid can also be optionally substituted with a conjugating group to allow targeting of a peptide or antibody. The addition of 2 or more Gd-chelates in a molecule increases the relaxivity by at least an additive manner.

Compounds (I) in which $R_1$ is hydrogen, alkyl, cycloalkyl, cycloalkylalkyl or aryl can be prepared with a process which comprises:

a) reacting a compound (II)

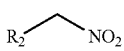

II wherein $R_2$ is as defined above, with formaldehyde and an amine (III)

$R_1$—$NH_2$       III

wherein $R_1$ is as defined above, to give a compound of formula (IV)

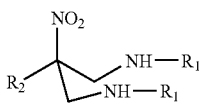

IV b) reducing the nitro group of compound (IV) to amino group, to give a compound of formula (V)

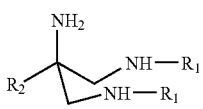

V reacting compounds of formula (V) with haloacetic acid esters, or methyl substituted haloacetic acid esters to give compounds (VI)

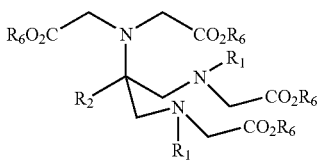

VI wherein $R_6$ is $C_1$-$C_6$ alkyl, and subsequent hydrolysis to give compounds (I), or reacting compounds (V) with formaldehyde and phosphorous acid or a compound of formula $RP(OH)_2$, wherein R is as defined above, to give the corresponding compounds (I) in which FG is —$PO_3H_2$ or RP(O)OH.

Compounds of formula (I) in which the two $R_1$ groups taken together form an alkylene group are obtained with a process comprising:

a) reacting a compound (II) with formaldehyde or a primary aliphatic aldehyde and a diamine of formula (VII)

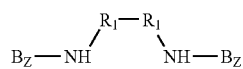

VII wherein $R_1$ is as defined above and Bz is benzyl or an aminoprotective group, to give compound of formula (VIII)

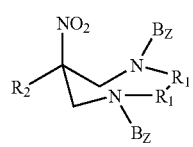

VIII b) reducing the nitro group and removing the benzyl groups. e.g. by catalytic hydrogenation, from compound (VIII) to give a compound of formula (IX)

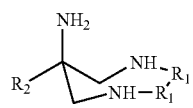

IX c) reacting (IX) with haloacetic acid esters to give a compound (X)

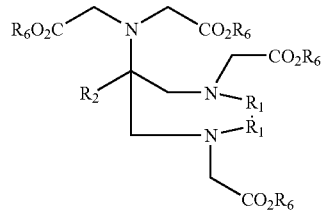

X wherein $R_6$ is as defined above, or with formaldehyde or a primary aliphatic aldehyde and phosphorous acid or a compound of formula $RP(OH)_2$, wherein R is as defined above, to give the corresponding compounds (I) in which FG is —$PO_3H_2$ or RP(O)OH;

d) hydrolyzing the carboxy ester groups to give compounds (I) wherein the $R_1$ groups form together an alkylene.

Compounds of formula (I) in which both carboxylic groups and phosphonic groups are present, can be obtained by suitably changing the reactions sequences reported above, introducing the carboxymethyl or phosphonomethyl groups on the previously deprotected compound of formula (VIII), for example first by reaction with haloacetic esters, subsequent reduction of the nitro group and further reaction with formaldehyde and $H_3PO_3$ or $RP(OH)_2$, as described above, or vice versa. According to this procedure can also be prepared compounds of formula (I) in which the FG groups on the nitrogen atom of the ring are different from the FG groups present on the exocyclic amino group.

Amines of formula (IX), both in the protected and unprotected form, are novel and are a further object of the invention, as intermediates.

The compounds of the invention can further be conjugated with one or more suitable molecules able to interact with physiological systems. Useful examples thereof, are bile acids, peptides, proteins, hormones, oligonucleotides, antibiotics, antibodies, enzymes, growth factors and the like.

Molecules able to interact with physiological systems are also called targeting moieties. A targeting moiety is any molecule that has a binding affinity for particular site or a specific metabolic function. The targeting moiety or moieties directs the compounds of the invention to the appropriate site, or involves the compounds in a reaction, where the desired diagnostic or therapeutic activity will occur. In an exemplary embodiment, a targeting moiety may be a peptide, equivalent, derivative or analog thereof which functions as a ligand that binds to a particular site. In another exemplary embodiment, the targeting moiety may be an enzyme, or a molecule that binds to an enzyme. In another exemplary embodiment, the targeting moiety may be an antibiotic. In yet another embodiment a targeting moiety may be an antibody or fragment thereof that binds to a site of interest, such as for example, a desired receptor.

In a preferred embodiment, the targeting moiety (or moieties) comprises a peptide that binds to a receptor or enzyme of interest. For example, the targeting peptide may be a peptide hormone such as, for example, luteinizing hormone releasing hormone (LHRH) such as that described in the literature [e.g., Radiometal-Binding Analogues of Luteinizing Hormone Releasing Hormone PCT/US96/08695; PCT/US97/12084 (WO 98/02192)]; insulin; oxytosin; somatostatin; Neuro kinin-1 (NK-1); Vasoactive Intestinal Peptide (VIP) including both linear and cyclic versions as delineated in the Literature, [e.g., Comparison of Cyclic and Linear Analogs of Vasoactive Intestinal Peptide. D. R. Bolin, J. M. Cottrell, R. Garippa, N. Rinaldi, R. Senda, B. Simkio, M. O'Donnell. Peptides: Chemistry, Structure and Biology Pravin T. P. Kaumaya, and Roberts S. Hodges (Eds). Mayflower Scientific LTD., 1996, pgs 174-175]; gastrin releasing peptide (GRP); bombesin and other known hormone peptides, as well as analogues and derivatives thereof.

Other useful targeting peptides include analogues of somatostatin which, for example, are Lanreotide (Nal-Cys-Thr-DTrp-Lys-Val-Cys-Thr-NH$_2$), Octreotide (Nal-Cys-Thr-DTrp-Lys-Val-Cys-Thr-ol), and Maltose (Phe-Cys-Thr-DTrp-Lys-Val-Cys-Thr-ol). These analogues are described in the literature [e.g., Potent Somatostatin Analogs Containing N-terminal Modifications, S. H. Kim, J. Z. Dong, T. D. Gordon, H. L. Kimball, S. C. Moreau, J.-P. Moreau, B. A. Morgan, W. A. Murphy and J. E. Taylor; Peptides: Chemistry, Structure and Biology Pravin T. P. Kaumaya, and Roberts S. Hodges (Eds)., Mayflower Scientific LTD., 1996, pgs 241-243.] Similarly, peptides which target angiogenesis-related receptors, such as, for example, VEGF receptors may be used as targeting moieties. Examples of such peptides are disclosed in PCT/US03/28787; U.S. Ser. No. 10/939,890; U.S. Ser. No. 09/871,974; and PCT/US01/18053, which are incorporated herein by reference.

Still other useful targeting peptides include Substance P agonists [e.g., G. Bitan, G. Byk, Y. Mahriki, M. Hanani, D. Halle, Z. Selinger, C. Gilon, Peptides: Chemistry, Structure and Biology, Pravin T. P. Kaumaya, and Roberts S. Hodges (Eds), Mayflower Scientific LTD., 1996, pgs 697-698; G Protein Antagonists A novel hydrophobic peptide competes with receptor for G protein binding, Hidehito Mukai, Eisuke Munekata, Tsutomu Higashijima, J. Biol. Chem. 1992, 267, 16237-16243]; NPY(Y1) [e.g., Novel Analogues of Neuropeptide Y with a Preference for the Y1-receptor, Richard M. Soll, Michaela, C. Dinger, Ingrid Lundell, Dan Larhammer, Annette G. Beck-Sickinger, Eur. J. Biochem. 2001, 268, 2828-2837; 99mTc-Labeled Neuropeptide Y Analogues as Potential Tumor Imaging Agents, Michael Langer, Roberto La Bella, Elisa Garcia-Garayoa, Annette G. Beck-Sickinger, Bioconjugate Chem. 2001, 12, 1028-1034; Novel Peptide Conjugates for Tumor-Specific Chemotherapy, Michael Langer, Felix Kratz, Barbara Rothen-Rutishauser, Heidi Wnderli-Allenspach, Annette G. Beck-Sickinger, J. Med. Chem. 2001, 44, 1341-1348]; oxytocin; endothelin A and endothelin B; bradykinin; Epidural Growth Factor (EGF); Interleukin-1 [Anti-IL-1 Activity of Peptide Fragments of IL-1 Family Proteins, I. Z. Siemion, A. Kluczyk, Zbigtniew Wieczorek, Peptides 1998, 19, 373-382]; and cholecystokinin (CCK-B) [Cholecystokinin Receptor Imaging Using an Octapeptide DTPA-CCK Analogue in Patients with Medullary Thyroid Carcinoma, Eur. J. Nucl Med. 200, 27, 1312-1317].

Literature which gives a general review of targeting peptides, can be found, for example, in the following: The Role of Peptides and Their Receptors as Tumor Markers, Jean-Claude Reubi, Gastrointestinal Hormones in Medicine, Pg 899-939; Peptide Radiopharmaceutical in Nuclear Medicine, D. Blok, R. I. J. Feitsma, P. Vermeij, E. J. K. Pauwels, Eur. J. Nucl Med. 1999, 26, 1511-1519; and Radiolabeled Peptides and Other Ligands for Receptors Overexpressed in Tumor Cells for Imaging Neoplasms, John G. McAfee, Ronald D. Neumann, Nuclear Medicine and Biology, 1996, 23, 673-676 (somatostatin, VIP, CCK, GRP, Substance P, Galanan, MSH, LHRH, Arginine-vasopressin, endothelin). All of the aforementioned literature in the preceding paragraphs are herein incorporated by reference in their entirety.

Other targeting peptide references include the following: Co-expressed peptide receptors in breast cancer as a molecular basis of in vivo multireceptor tumour targeting. Jean Claude Reubi, Mathias Gugger, Beatrice Waser. Eur. J. Nucl Med. 2002, 29, 855-862, (includes NPY, GRP); Radiometal-Binding Analogues of Leutenizing Hormone Releasing Hormone PCT/US96/08695 (LHRH); PCT/US97/12084 (WO 98/02192) (LHRH); PCT/EP90/01169 (radiotherapy peptides); WO 91/01144 (radiotherapy peptides); and PCT/EP00/01553 (molecules for the treatment and diagnosis of tumours), all of which are herein incorporated by reference in their entirety.

Additionally, analogues of a targeting peptide can be used. These analogues include molecules that target a desired site receptor with avidity that is greater than or equal to the targeting peptide itself, as well as muteins, retropeptides and retro-inverso-peptides of the targeting peptide. One of ordinary skill will appreciate that these analogues may also contain modifications which include substitutions, and/or deletions and/or additions of one or several amino acids, insofar that these modifications do not negatively alter the biological activity of the peptides described therein. These substitutions may be carried out by replacing one or more amino acids by their synonymous amino acids. Synonymous amino acids within a group are defined as amino acids that have sufficiently similar physicochemical properties to allow substitution between members of a group in order to preserve the biological function of the molecule. Synonymous amino acids as used herein include synthetic derivatives of these amino acids (such as for example the D-forms of amino acids and other synthetic derivatives).

Deletions or insertions of amino acids may also be introduced into the defined sequences provided they do not alter the biological functions of said sequences. Preferentially such insertions or deletions should be limited to 1, 2, 3, 4 or 5 amino acids and should not remove or physically disturb or displace amino acids which are critical to the functional conformation. Muteins of the peptides or polypeptides described herein may have a sequence homologous to the sequence disclosed in the present specification in which amino acid substitutions, deletions, or insertions are present at one or more amino acid positions. Muteins may have a biological activity that is at least 40%, preferably at least 50%, more preferably 60-70%, most preferably 80-90% of the peptides described herein. However, they may also have a biological activity greater than the peptides specifically exemplified, and thus do not necessarily have to be identical to the biological function of the exemplified peptides. Analogues of targeting peptides also include peptidomimetics or pseudopeptides incorporating changes to the amide bonds of the peptide backbone, including thioamides, methylene amines, and E-olefins. Also peptides based on the structure of a targeting peptide or its peptide analogues with amino acids replaced by N-substituted hydrazine carbonyl compounds (also known as aza amino acids) are included in the term analogues as used herein.

Targeting molecule may be attached via the methods disclosed herein and those known to the skilled artisan. For example, targeting peptides may be attached to a linker or to the chelator via the N or C terminus or via attachment to the epsilon nitrogen of lysine, the gamma nitrogen or ornithine or the second carboxyl group of aspartic or glutamic acid.

The present invention also includes coupling conditions for coupling functionalized Aazta-derivatives with targeting moieties. For example, Examples 4, 5, 6, 7 and 15 below disclose Aazta derivatives with an amino group or a protected amino group (deprotected before coupling). They can be coupled to T-NH2 (Targeting moiety containing an amino group) by method 1. T-CO$_2$H (Targeting moiety containing a carboxylic acid group) can be coupled to Aazta-NH$_2$ by method 2. (Activation methods known in the literature can be used)

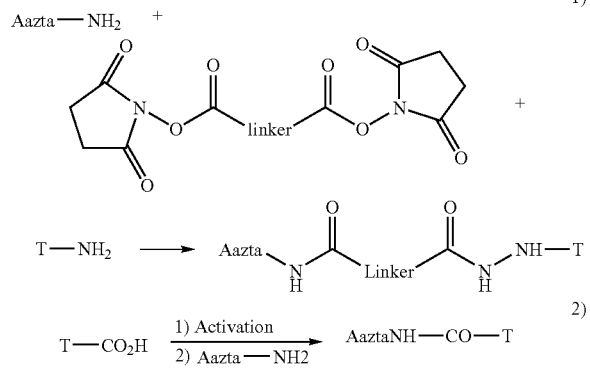

Examples 8, 9, 18, 22, 23, 24 below describe Aazta derivatives with a carboxylic acid side chain. The can be coupled to T-NH$_2$ targeting moiety containing an amino group by the methods shown below

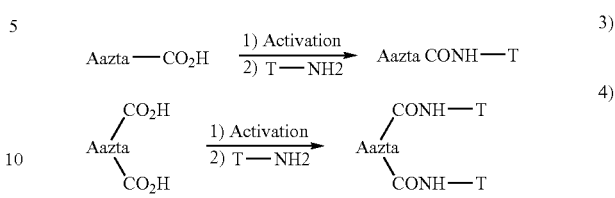

In two exemplary embodiments of the invention, shown more fully below, the targeting molecule targets fibrin or a GRP (gastrin releasing peptide) receptor (GRP-R). Where a targeting molecule binds to a GRP-R the compounds of the invention, when labeled with an appropriate metal, can be used to image or treat tumors expressing GRP receptors, such as, for example, primary or metastatic prostate, breast and lung tumors. Where a targeting molecule binds fibrin, compounds of the invention, when labeled with an appropriate metal, can be used to image or treat fibrin containing blood clots/thrombus, plaques, or tumors.

Cardiovascular disease is a major cause of death in the world. Sudden plaque rupture can lead to stroke and heart attacks and death. The ability to image plaques and especially unstable plaques is an important area of diagnostic imaging. These plaques contain fibrin, which can be effectively targeted with peptides or antibodies. Fibrin is also present in thrombus and in cancerous tumors. This provides additional applications for fibrin imaging.

Also included within the scope of the present invention is the use of one or more "spacer" or "linker" group to create a physical separation between the metal chelator and the targeting agent. The use of a spacer or linker is described in more detail in U.S. Pat. No. 5,976,495 to Pollak, et al, which is incorporated herein by reference.

Linking groups include a chemical group that serves to couple the chelator of the invention to the targeting moiety or moieties while not adversely affecting either the targeting function of the targeting moiety or the diagnostic or therapeutic function of the chelator. Suitable linking groups include, for example, peptides (i.e., amino acids linked together) alone, a non-peptide group (e.g., hydrocarbon chain) or a combination of an amino acid sequence and a non-peptide spacer. Other suitable linkers include polyethylene glycol (PEG) linkers.

In one embodiment, linking groups include L-glutamine and hydrocarbon chains, or a combination thereof.

In another embodiment, linking groups include a pure peptide linking group consisting of a series of amino acids (e.g., diglycine, triglycine, gly-gly-glu, gly-ser-gly, etc.).

In yet a further embodiment, linking groups can also include a hydrocarbon chain [i.e., $R_1$—$(CH_2)_n$—$R_2$] wherein n is 0-10, preferably n=3 to 9, $R_1$ is a group (e.g., $H_2N$—, HS—, —COOH) that can be used as a site for covalently linking the ligand backbone or the preformed metal chelator or metal complexing backbone; and $R_2$ is a group that is used for covalent coupling to the N-terminal $NH_2$-group of a given targeting peptide (e.g., $R_2$ is an activated COOH group). Several chemical methods for conjugating ligands (i.e., chelators) or chelates (chelators/ligands complexed with a radionuclide) to biomolecules (such as targeting moieties) have been well described in the literature [Wilbur, 1992; Parker, 1990; Hermanson, 1996; Frizberg et al., 1995]. One or more of these methods could be used to link either the uncomplexed ligand (chelator) or the radiometal chelate to the linker or to link the linker to the targeting moiety or other diagnostic or therapeutic moiety. These methods include the formation of acid anhydrides, aldehydes, arylisothiocyanates, activated esters, or N-hydroxysuccinimides [Wilbur, 1992; Parker, 1990; Hermanson, 1996; Frizberg et al., 1995].

In a preferred embodiment, linking groups may be formed from linker precursors having electrophiles or nucleophiles as set forth below:

LP1: a linker precursor having on at least two locations of the linker the same electrophile E1 or the same nucleophile Nu1;

LP2: a linker precursor having an electrophile E1 and on another location of the linker a different electrophile E2;

LP3: a linker precursor having a nucleophile Nut and on another location of the linker a different nucleophile Nu2; or LP4: a linker precursor having one end functionalized with an electrophile E1 and the other with a nucleophile Nut.

In one embodiment of the present invention, the linker contains at least one substituted bile acid. Bile acids are found in bile (a secretion of the liver) and are steroids having a hydroxyl group and a five carbon atom side chain terminating in a carboxyl group. In substituted bile acids, at least one atom such as a hydrogen atom of the bile acid is substituted with another atom, molecule or chemical group. For example, substituted bile acids include those having a 3-amino, 24-carboxyl function optionally substituted at positions 7 and 12 with hydrogen, hydroxyl or keto functionality.

Other useful substituted bile acids in the present invention include substituted cholic acids and derivatives thereof. Specific substituted cholic acid derivatives include:

(3β,5β)-3-aminocholan-24-oic acid;
(3β,5β,12α)-3-amino-12-hydroxycholan-24-oic acid;
(3β,5β,7α,12α)-3-amino-7,12-dihydroxycholan-24-oic acid;
Lys-(3,6,9)-trioxaundecane-1,11-dicarbonyl-3,7-dideoxy-3-aminocholic acid);
(3β,5β,7α)-3-amino-7-hydroxy-12-oxocholan-24-oic acid; and
(3β,5β,7α)-3-amino-7-hydroxycholan-24-oic acid.

Such linkers are described in more detail in PCT/US03/41656 and in U.S. Ser. No. 11/165,721, filed Jun. 24, 2005, now published as US-2006-0018830-A1, both of which are incorporated herein by reference in their entirety.

In another embodiment of the invention, the linker contains at least one non-alpha amino acid. Non-alpha amino acids are known in the art and include those which are naturally occurring or synthetic. Preferred non-alpha amino acids include:

8-amino-3,6-dioxaoctanoic acid;
N-4-aminoethyl-N-1-acetic acid; and
polyethylene glycol derivatives having the formula NH2-(CH2CH2O)n-CH2CO2H or NH2-(CH2CH2O)n-CH2CH2CO2H where n=2 to 100.

Such linkers are described in more detail in PCT/US03/41656 and in U.S. Ser. No. 11/165,721, filed Jun. 24, 2005, now published as US-2006-0018830-A1, both of which are incorporated herein by reference in their entirety.

In yet another embodiment of the present invention, the linker contains at least one non-alpha amino acid with a cyclic group. Non-alpha amino acids with a cyclic group include substituted phenyl, biphenyl, cyclohexyl or other amine and carboxyl containing cyclic aliphatic or heterocyclic moieties. Examples of such include:

4-aminobenzoic acid (hereinafter referred to as "Abz4 in the specification")
3-aminobenzoic acid
4-aminomethyl benzoic acid8-aminooctanoic acid
trans-4-aminomethylcyclohexane carboxylic acid
4-(2-aminoethoxy)benzoic acid
isonipecotic acid
2-aminomethylbenzoic acid
4-amino-3-nitrobenzoic acid
4-(3-carboxymethyl-2-keto-1-benzimidazolyl-piperidine
6-(piperazin-1-yl)-4-(3H)-quinazolinone-3-acetic acid
(2S,5S)-5-amino-1,2,4,5,6,7-hexahydro-azepino[3,21-hi]indole-4-one-2-carboxylic acid
(4S,7R)-4-amino-6-aza-5-oxo-9-thiabicyclo[4.3.0]nonane-7-carboxylic acid
3-carboxymethyl-1-phenyl-1,3,8-triazaspiro[4.5]decan-4-one
N1-piperazineacetic acid
N-4-aminoethyl-N-1-piperazineacetic acid
(3S)-3-amino-1-carboxymethylcaprolactam
(2S,6S,9)-6-amino-2-carboxymethyl-3,8-diazabicyclo-[4,3,0]-nonane-1,4-dione
3-amino-3-deoxycholic acid
4-hydroxybenzoic acid
4-aminophenylacetic acid
3-hydroxy-4-aminobenzoic acid
3-methyl-4-aminobenzoic acid
3-chloro-4-aminobenzoic acid
3-methoxy-4-aminobenzoic acid
6-aminonaphthoic acid
N,N'-Bis(2-aminoethyl)-succinamic acid Such linkers are described in more detail in PCT/US03/41656 and in U.S. Ser. No. 11/165,721, filed Jun. 24, 2005, now published as US-2006-0018830-A1, both of which are incorporated herein by reference in their entirety.

The complexes of compounds (11 can be administered as MRI contrast agents or radiopharmaceuticals parenterally, preferably formulated as a sterile aqueous solution or suspension, whose pH can range for example from 6.0 to 8.5.

Said aqueous solutions or suspensions can be administered in concentrations ranging from 0.002 to 1.0 molar.

Said formulations can be freeze-dried and supplied as such, to be reconstituted prior to use. For the gastrointestinal use or for injection to body cavities, these agents can be formulated as a solution or suspension containing suitable additives in order to, for example, control viscosity.

For the oral administration they can be formulated according to preparation methods routinely used in pharmaceutical technique, optionally also as coated formulations to gain extra protection from the acid pH of the stomach, inhibiting the release of the chelated metal ion, which usually occurs at typical pH values of gastric juices.

Other excipients, such as sweetening agents and/o flavoring agents, can also be added according to known techniques of pharmaceutical formulation.

Paramagnetic Gd(III) complexes with ligands of formula (I) are endowed with a particularly good starting relaxivity which can be explained with the presence of two water molecules in the inner coordination sphere of said complexes and with simultaneous favorable fast exchange rate of coordinated water molecules.

It has been reported that for some Gd(III) complexes with q=2 (i.e. Gd-DO3A-like systems, a decrease in relaxivity was observed upon increasing of the solution pH. This decrease is most probably due to the fact that some anions present in the solution, such as the and hydroxyl ions, are in competition with the water molecules for the coordination sites on Gd(III) and, through the formation of ternary complexes with metal chelate, remarkably reduces the relaxivity thereof (S. Aime et al, *J. Biol. Inorg. Chem.*, 5, 488-497, (2000) Decrease in relaxivity is also observed when bidentate ligands are present in solution. Systems showing such behaviour are usually characterized by a small relaxation enhancement upon binding to proteins such as HSA. This is due to the replacement of the water molecules by donor atoms on the protein.

Conversely, tests performed with the Gd(III) complex of example 1 of the invention quite interestingly pointed out the ligands of the invention show a very low affinity for any anions and anionic metabolites present in solution.

This result strongly indicates that the relaxivity of the complex compounds of the invention is not "lowered" even in the presence of high concentrations of bidentate anions.

It further indicates that the ligands of the invention can advantageously be used to prepare paramagnetic complex compounds with q=2, able to be conjugated to or to non-covalently interact with human serum albumin or other suitable macromolecules without that the donor atoms on said macromolecule, (for example, from aspartate or glutamate), could interact with the coordination sites of Gd(III) and induce a reduction of the attainable relaxivity.

Most probably, the substantial change in the ligands structure when compared with that of (DO3A) and of the corresponding DO3MA trimethyl-derivate is responsible of the completely different behavior of the complex towards the bidentate anions.

When labeled with diagnostically or therapeutically useful metals, compounds of the present invention can also be used to treat and/or detect diseases such as cancers, including tumors, as well as cardiovascular disases, by procedures established in the arts of diagnostic imaging, radiodiagnostics and radiotherapeutics. [Bushbaum, 1995; Fischman et al., 1993; Schubiger et al., 1996; Lowbertz et al., 1994; Krenning et al., 1994].

The diagnostic application of these compounds can be as a first line diagnostic screen for the presence of targeted cells using diagnostic imaging (such as, for example, scintigraphic or magnetic resonance imaging), as an agent for targeting selected tissue using hand-held radiation detection instrumentation in the field of radioimmuno guided surgery (RIGS), as a means to obtain dosimetry data prior to administration of the matched pair radiotherapeutic compound, and as a means to assess a targeted receptor population as a function of treatment over time.

The compounds of the invention are also therapeutically useful. Specifically, compounds of the invention labeled with the appropriate therapeutic radionuclide are useful in radio-isotope therapy. Radioisotope therapy (radiotherapy) involves the administration of a radiolabeled compound in sufficient quantity to damage or destroy the targeted tissue. After administration of the compound (by e.g., intravenous, subcutaneous, or intraperitonal injection), the radiolabeled pharmaceutical localizes preferentially at the disease site (e.g, tumor tissue, etc,) Once localized, the radiolabeled compound then damages or destroys the diseased tissue with the energy that is released during the radioactive decay of the isotope that is administered. As discussed herein, the compounds of the invention may be used in radiotherapy in combination with adjuvant chemotherapy (or in combination with any other appropriate therapeutic agent).

The design of a successful radiotherapeutic involves several critical factors:
1. selection of an appropriate targeting group to deliver the radioactivity to the disease site;
2. selection of an appropriate radionuclide that releases sufficient energy to damage that disease site, without substantially damaging adjacent normal tissues; and
3. selection of an appropriate combination of the targeting group and the radionuclide without adversely affecting the ability of this conjugate to localize at the disease site. For radiometals, this often involves a chelating group that coordinates tightly to the radionuclide, combined with a linker that couples said chelate to the targeting group, and that affects the overall biodistribution of the compound to maximize uptake in target tissues and minimize uptake in normal, non-target organs.

The chelators of the present invention when complexed with an appropriate radionuclide and, preferably targeting group and linker are useful for radiotherapy.

Compounds of the invention useful for radiotherapy are advantageously complexed with a 3+ metal ion from the class of elements known as the lanthanides (elements of atomic number 57-71) and their analogs (i.e. M3+ metals such as yttrium and indium). Typical radioactive metals in this class include the isotopes 90-Yttrium, 111-Indium, 149-Promethium, 153-Samarium, 166-Dysprosium, 166-Holmium, 175-Ytterbium, and 177-Lutetium. All of these metals (and others in the lanthanide series) have very similar chemistries, in that they remain in the +3 oxidation state, and prefer to complex to ligands that bear hard (oxygen/nitrogen) donor atoms, such as the chelators of the invention.

The chealtors of the invention complex with and prevent the release of free (unbound) radiometal into the body. This is important, as in vivo dissociation of 3+ radiometals from their chelate can result in uptake of the radiometal in the liver, bone and spleen [Brechbiel M W, Gansow O A, "Backbone-substituted DTPA ligands for $^{90}$Y radioimmunotherapy", Bioconj. Chem. 1991; 2: 187-194; Li, W P, Ma D S, Higginbotham C, Hoffman T, Ketring A R, Cutler C S, Jurisson, S S, "Development of an in vitro model for assessing the in vivo stability of lanthanide chelates." Nucl. Med. Biol. 2001; 28(2): 145-154; Kasokat T, Urich, K. Arzneim.-Forsch, "Quantification of dechelation of gadopentetate dimeglumine in rats". 1992; 42(6): 869-76]. Unless one is specifically targeting these organs, such non-specific uptake is highly undesirable, as it leads to non-specific irradiation of non-target tissues, which can lead to such problems as hematopoietic suppression due to irradiation of bone marrow.

The selection of a proper radionuclide for use in a particular radiotherapeutic application depends on many factors, including:
a. Physical half-life—This should be long enough to allow synthesis and purification of the radiotherapeutic construct from radiometal and conjugate, and delivery of said construct to the site of injection, without significant radioactive decay prior to injection. Preferably, the radionuclide should have a physical half-life between about 0.5 and 8 days.
b. Energy of the emission(s) from the radionuclide—Radionuclides that are particle emitters (such as alpha emitters, beta emitters and Auger electron emitters) are particularly useful, as they emit highly energetic particles that deposit their energy over short distances, thereby producing highly localized damage. Beta emitting radionuclides are particularly preferred, as the energy from beta particle emissions from these isotopes is deposited within 5 to about 150 cell diameters. Radiotherapeutic agents prepared from these nuclides are capable of killing diseased cells that are relatively close to their site of localization, but cannot travel long distances to damage adjacent normal tissue such as bone marrow.

c. Specific activity (i.e. radioactivity per mass of the radionuclide)-Radionuclides that have high specific activity (e.g. generator produced 90-Y, 111-In, 177-Lu) are particularly preferred. The specific activity of a radionuclide is determined by its method of production, the particular target that is used to produce it, and the properties of the isotope in question.

Many of the lanthanides and lanthanoids include radioisotopes that have nuclear properties that make them suitable for use as radiotherapeutic agents, as they emit beta particles. Some of these are listed in the table below.

| Isotope | Half-Life(days) | Max b-energy(MeV) | Gamma energy(keV) | Approximate range of b-particle(cell diameters) |
|---|---|---|---|---|
| $^{149}$-Pm | 2.21 | 1.1 | 286 | 60 |
| $^{153}$-Sm | 1.93 | 0.69 | 103 | 30 |
| $^{166}$-Dy | 3.40 | 0.40 | 82.5 | 15 |
| $^{166}$-Ho | 1.12 | 1.8 | 80.6 | 117 |
| $^{175}$-Yb | 4.19 | 0.47 | 396 | 17 |
| $^{177}$-Lu | 6.71 | 0.50 | 208 | 20 |
| $^{90}$-Y | 2.67 | 2.28 | — | 150 |
| $^{111}$-In | 2.810 | Auger electron emitter | 173,247 | <5*m |

Pm Promethium,
Sm Samarium,
Dy Dysprosium,
Ho Holmium,
Yb Ytterbium,
Lu Lutetium,
Y Yttrium,
In Indium Methods for the preparation of radiometals such as beta-emitting lanthanide radioisotopes are known to those skilled in the art, and have been described elsewhere [e.g., Cutler C S, Smith C J, Ehrhardt G J.; Tyler T T, Jurisson S S, Deutsch E. "Current and potential therapeutic uses of lanthanide radioisotopes." Cancer Biother, Radiopharm. 2000; 15(6): 531-545]. Many of these isotopes can be produced in high yield for relatively low cost, and many (e.g. $^{90}$-Y, $^{149}$-Pm, $^{177}$-Lu) can be produced at close to carrier-free specific activities (i.e. the vast majority of atoms are radioactive). Since non-radioactive atoms can compete with their radioactive analogs for binding to receptors on the target tissue, the use of high specific activity radioisotope is important, to allow delivery of as high a dose of radioactivity to the target tissue as possible.

Therapeutic application of compounds of the invention complexed with therapeutic radionuclides can be defined either as radiopharmaceutical that will be used as a first line therapy in the treatment of a disease such as cancer, as a combination therapy where the radiotherapeutic agents of the invention could be utilized in conjunction with adjuvant chemotherapy (e.g, with one of the other therapeutic agents disclosed herein), or as the therapeutic part of a matched pair therapeutic agent. The matched pair concept refers to a single unmetallated compound which can serve as both a diagnostic and a therapeutic agent depending on the radiometal that has been selected for binding to the appropriate chelate. If the chelator cannot accommodate the desired metals appropriate substitutions can be made to accommodate the different metal while maintaining the pharmacology such that the behaviour of the diagnostic compound in vivo can be used to predict the behaviour of the radiotherapeutic compound.

The following examples illustrate the invention in greater detail.

EXAMPLE 1

1,4-Bis(carboxymethyl)-6-[bis(carboxymethyl)amino]-6-methyl-perhydro-1,4-diazepine

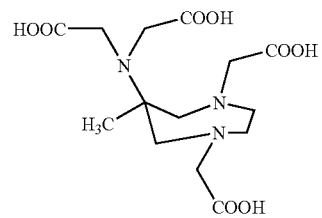

a) 1,4-Dibenzyl-6-methyl-6-nitroperhydro-1,4-diazepine

In a 250 mL round-bottom flask N,N'-dibenzylethylenediamine diacetate (18.4 g, 51.0 mmol) and nitroethane (3.66 mL, 50.9 mmol) are dissolved in ethanol (80 mL). Paraformaldehyde (5.00 g, 166.5 mmol) is added in portions to the solution and the resulting suspension is refluxed. The mixture becomes homogeneous (dissolution of paraformaldehyde) at about 60° C. and a slightly exothermic reaction takes place. After 3 h at reflux, the mixture is evaporated, taken up with aqueous saturated Na$_2$CO$_3$ solution and the organic product is repeatedly extracted with methylene chloride. The combined organic extracts are washed with water and dried over Na$_2$SO$_4$. After filtration and evaporation of methylene chloride, the waxy residue is purified by silica gel chromatography.

Elution with methylene chloride yields the pure title compound (15.65 g, 90.6%). Increasing the polarity of the eluent (CH$_2$Cl$_2$/MeOH 9:1), the acyclic derivative N,N'-dibenzyl-N-(2-nitropropyl)ethanediamine (0.350 g, 2.1%) is obtained.

Waxy white solid, m.p. 49.5-50° C. (n-hexane)

$^1$H-NMR (CDCl$_3$)

7.32 (m, 10H), 3.78 (d, 2H, J=13.2 Hz), 3.65 (d, 2H, J=13.2 Hz). 3.60 (d, 2H, J=14.1 Hz), 2.96 (d, 2H, J=14.1 Hz), 2.60 (m, 4H). 1.35 (s, 3H).

$^{13}$C-NMR (CDCl$_3$)

139.0 (s), 128.8 (d), 128.1 (d), 127.1 (d), 91.5 (s), 63.7 (t), 63.4 (t), 58.1 (t), 24.2 (q).

MS (CI) 340 (MH$^+$).

Anal. Calc. for C$_{20}$H$_{25}$N$_3$O$_2$ (339.43): C, 70.77; H, 7.42; N, 12.38. Found: C, 70.57; H, 7.60; N, 12.27.

b) 6-Amino-6-methylperhydro-1,4-diazepine

To a solution of the compound obtained in a) (6.00 g, 17.7 mmol) in a mixture of ethanol (45 mL) and water (5 mL) is added the catalyst consisting of 10% palladium on charcoal (1.0 g). The mixture is introduced in a Parr apparatus, hydrogenated at 28 atm (2.84 MPa) and room temperature. After 2 h, hydrogen is no longer absorbed. The reaction mixture is filtered through Celite®. The filtrate is evaporated to obtain the title compound (2.25 g, 98.3%) sufficiently pure for the subsequent step, in the form of a colorless oil.

$^1$H-NMR (CDCl$_3$)

2.82 (m, 4H), 2.63 (d, 2H, J=13.6 Hz), 2.57 (d, 2H, J=13.6 Hz), 1.86 (bs, 4H, exchange with D$_2$O), 0.96 (s, 3H).

$^{13}$C-NMR (CDCl$_3$)

62.2 (t), 53.8 (s), 51.7 (t), 26.5 (q).

MS (CI) 130 (MH$^+$).
Anal. Calc. for $C_6H_{15}N_3$ (129.21): C, 55.78; H, 11.70; N, 32.52. Found: C, 55.56; H, 11.91; N, 32.29.

c) 1,4-Bis(t-butoxycarbonylmethyl)-6-[bis(t-butoxy-carbonylmethyl)-amino]-6-methylperhydro-1,4-diazepine To a solution of the compound obtained in b) (0.909 g, 7.04 mmol) in dry acetonitrile (25 mL), powdered potassium carbonate (6.53 g, 47.24 mmol) and sodium sulfate (ca. 3 g) are added. After cooling to 0-5° C. (ice bath) t-butyl bromoacetate (4.50 mL, 30.45 mmol) is added in 10 minutes and the mixture is left at this temperature for 15 minutes. Subsequently, the reaction mixture is refluxed for 4 hours, then cooled to room temperature, inorganic salts are filtered off and the filtrate is evaporated under vacuum. The resulting residue is purified by "flash" chromatography on silica gel. Elution with n-hexane/ethyl acetate 8:2 yields the pure title compound (3.15 g, 76.4%) as colorless oil.

$^1$H-NMR (CDCl$_3$)
3.68 (s, 4H), 3.27 (s, 4H), 3.03 (d, 2H, J=14.1 Hz), 2.72 (m, 4H), 2.61 (d, 2H, J=14.1 Hz), 1.44 (s, 36H), 1.09 (s, 3H).
$^{13}$C-NMR (CDCl$_3$)
172.6 (s), 170.8 (s), 80.6 (s), 80.1 (s), 66.1 (t), 62.3 (t), 60.6 (s), 59.1 (t), 51.5 (t), 28.1 (q), 28.0 (q), 24.1 (q).
MS (CI) 586 (MH$^+$).
Anal. Calc. for $C_{30}H_{55}N_3O_8$ (585.78): C, 61.51; H, 9.46; N, 7.17. Found: C, 61.42; H, 9.62; N, 6.98.

d) 1,4-Bis(carboxymethyl)-6-[bis(carboxymethyl)amino]-6-methyl-perhydro-1,4-diazepine In a 50 mL round-bottom flask, the ester obtained in c) (3.03 g, 5.17 mmol) is dissolved in trifluoroacetic acid (10 mL). The resulting solution is left at room temperature overnight, then is evaporated under vacuum, concentrated HCl is added and evaporated to dryness. The solid residue is loaded on an Amberlite® XAD 1600 resin column (3 cm ID×30 cm). Elution with water/acetone (100/0→70/30) yields the pure title compound (1.33 g, 71.1%) as white crystals, m.p. 178-181° C. (dec.) (H$_2$O).

$^1$H-NMR (D$_2$O)
3.65 (s, 8H), 3.51 (m, 4H), 3.38 (m, 4H), 1.06 (s, 3H)
$^{13}$C-NMR (D$_2$O)
175.9 (s), 173.3 (s), 65.7 (s), 61.2 (t), 61.1 (t), 56.1 (t), 54.3 (t), 19.5 (q).
MS (FAB$^+$) 362 (MH$^+$).
Anal. Calc. for $C_{14}H_{23}N_3O_8$ (361.35): C, 46.53; H, 6.42; N, 11.63. Found: C, 46.56; H, 6.70; N, 11.39.
Operating analogously to the procedure described above, the following compounds may be synthesized:

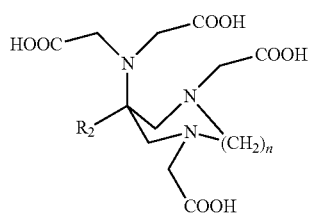

n = 2, 3
R$_2$ = CH$_3$, Ar, (CH$_2$)$_n$COOR, (CH$_2$)$_n$NPG$_2$

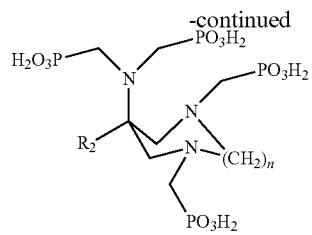

n = 2, 3
R$_2$ = CH$_3$, Ar, (CH$_2$)$_n$COOR, (CH$_2$)$_n$NPG$_2$

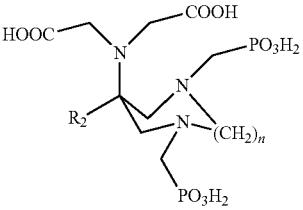

n = 2, 3
R$_2$ = CH$_3$, Ar, (CH$_2$)$_n$COOR, (CH$_2$)$_n$NPG$_2$

In particular the following ligands may be prepared:

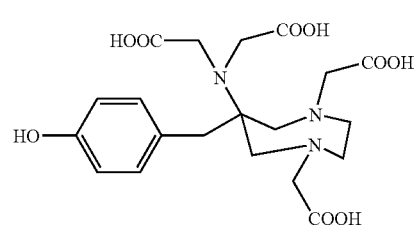

A

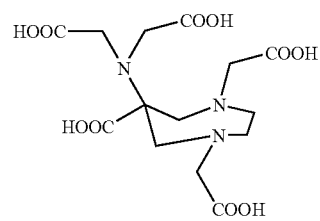

B

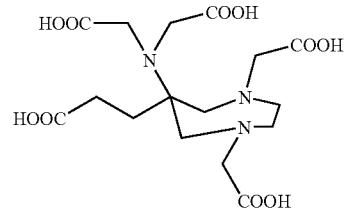

C

See, in particular Example 8, where the preparation of Ligand C is detailed.

e) Gd(III) Complex of 1,4-Bis(carboxymethylmethyl)-6-[bis(hydroxycarbonyl-methyl)amino]-6-methylperhydro-1,4-diazepine In a 100 mL round-bottom flask, the ligand from d) (3.61 g, 10 mmol) is suspended in 30 mL of H$_2$O, 1N NaOH (10 mL) is added to obtain a clear solution, to which Gd$_2$O$_3$ (1.81 g, 5 mmol) and heated at 50° C. for 15 hours. After cooling at room temperature, the solution is filtered and evaporated to dryness to obtain a white solid.

Anal. Calc. for $C_{14}H_{19}GdN_3NaO_8$ (537.56): C, 31.28; H, 3.56; N, 7.82; Na, 4.28; Gd, 29.25. Found: C, 30.98; H, 3.71; N, 7.99; Na 4.01; Gd 29.59.

This procedure (together with any modifications known to one skilled in the art) may be used to label any of the compounds of the invention with a paramagnetic metal such as gadolinium.

EXAMPLE 2

N,N''-diisopropyl-2-methyl-1,2,3-propanetriamino-N,N',N',N''-tetraacetic acid

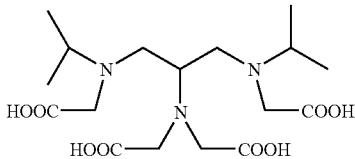

a) N,N'-Diisopropyl-2-methyl-2-nitro-1,3-propanediamine

A 250 mL round-bottom flask containing isopropylamine (20.6 g, 349 mmol) is cooled to 3-5° C. on ice bath and 37% aqueous formaldehyde solution (26.3 mL, 350 mmol) is added in about 30 min so that the reaction temperature does not exceed 10° C. After completion of the addition, the mixture is stirred for 15 minutes, then nitroethane (13.1 g, 174.5 mmol) is added in a single portion. The mixture is left to warm to room temperature, then $Na_2SO_4$ (20 g) is added, stirring to complete dissolution. The two phases formed are separated and the lower aqueous layer is discarded. Further $Na_2SO_4$ (20 g) is added to the organic phase and left to stand for 60 hours. The mixture is filtered and the solid is repeatedly washed with diethyl ether. Filtrate and washings are combined and evaporated under vacuum. The residue is distilled under vacuum, collecting the fraction which distils at 88-90° C. under 3 mmHg, corresponding to the title product (25.9 g, 68.2%) as a colorless oil, p.eb. 88-90° C. (3 mmHg).

$^1$H-NMR ($CDCl_3$)

1.01 (d, 12H, J=6.2 Hz), 1.50 (bs, 2H, exchanges with $D_2O$). 1.55 (s, 3H), 2.73 (sept, 2H, J=6.2 Hz), 2.99 (AB, 4H, J=12.8 Hz).

$^{13}$C-NMR ($CDCl_3$)

20.7 (q), 22.8 (q), 48.9 (t), 52.5 (d), 91.9 (s).

MS (CI) 218 (MH$^+$).

Anal. Calc. for $C_{10}H_{23}N_3O_2$ (217.31): C, 55.27; H, 10.67; N, 19.34. found: C, 55.11; H, 10.81; N, 19.39.

b) N,N''-Diisopropyl-2-methyl-1,2,3-propanetriamine

To a solution of the compound obtained in a) (18.50 g, 85.1 mmol) in $CH_3OH$ (100 mL), Nickel Raney 50% in $H_2O$ (3.5 g) is added. The mixture is placed into a Parr apparatus and hydrogenated at 60 atm and room temperature. After about 3 h no more hydrogen absorption is observed. The mixture is filtered through Celite® and the residue is washed with $CH_3OH$ (2×15 mL). Filtrate and washings are combined and evaporated. The residue is distilled under vacuum, collecting the fraction distilling at 98-100° C. under 3 mmHg, corresponding to the title product (15.15 g, 95.0%), which is a lightly yellow clear oil, p.eb. 88-90° C. (3 mmHg).

$^1$H-NMR ($CDCl_3$)

1.02 (s, 3H), 1.03 (d, 12H, J=6.2 Hz), 1.40 (bs, 4H, exchanges with $D_2O$), 2.46 (AB, 4H, J=11.6 Hz), 2.71 (sept, 2H, J=6.2 Hz).

$^{13}$C-NMR ($CDCl_3$)

22.9 (q), 25.4 (q), 49.2 (t), 51.6 (s), 56.9 (d).

MS (CI) 188 (MH$^+$).

Anal. Calc. for $C_{10}H_{25}N_3$ (187.33): C, 64.12; H, 13.45; N, 22 43. Found: C, 63.89; H, 13.61; N, 22.49.

c) N,N''-Diisopropyl-N,N',N',N''-tetrakis(t-butoxycarbonylmethyl)-2-methyl-1,2,3-propanetriamine To a solution of the triamine from b) (1.25 g, 6.67 mmol) in acetonitrile (10 mL), N,N-diisopropylethylamine (11.6 mL, 66.6 mmol) is added. t-Butyl bromoacetate (5.90 mL, 36.5 mmol) is added dropwise in 30 minutes under stirring and cooling on ice bath; after completion of the addition the ice bath is removed and the mixture is left at room temperature for further 30 minutes, then refluxed for 15 hours. After that, the mixture is cooled and evaporated under vacuum. The residue is partitioned between $CH_2Cl_2$ and a 10% aqueous $Na_2CO_3$ solution, and the aqueous phase is further extracted with $CH_2Cl_2$ (2×20 mL). The organic phases are dried over $Na_2SO_4$, filtered and evaporated under vacuum. The residue is purified by column chromatography ($SiO_2$, gradient hexane/$Et_2O$ 100/0→50/50, 30 mL fractions) to obtain the pure title tetraester (3.57 g, 83.0%) as a slightly yellow clear oil.

Rf ($SiO_2$, $CHCl_3$) 0.70.

$^1$H-NMR ($CDCl_3$)

0.91 (d, 6H, J=6.6 Hz), 0.96 (d, 6H, J=6.8 Hz), 1.16 (s, 3H), 1.41 (s, 36H), 2.57 (AB, 4H, J=14.3 Hz), 2.87 (sept, 2H, J=6.6 Hz), 3.38 (s, 4H), 3.52 (s, 4H).

$^{13}$C-NMR ($CDCl_3$)

17.7 (q), 19.8 (q), 19.9 (q), 27.9 (q), 51.2 (s), 53.9 (t), 54.0 (t), 55.0 (t), 63.1 (d), 79.7 (d), 80.0 (s), 172.0 (s), 172.9 (s).

MS (EI) 645, 644 (MH$^+$), 530, 457, 343, 287, 231, 186, 160, 130, 112, 88, 70.

Anal. Calc. for $C_{34}H_{65}N_3O_8$ (643.91): C, 63.42; H, 10.18; N, 6.53. found: C, 63.29; H, 10.33; N, 6.39.

d) N,N''-diisopropyl-2-methyl-1,2,3-propaneriamino-N,N',N',N''-tetraacetic acid

The ester from c) (5.96 g, 9.10 mmol) is placed in a 100 mL round-bottom flask and concentrated hydrochloric acid (20 mL) is added. The mixture is refluxed for 7 hours, then cooled, diluted with $H_2O$ (20 mL) and extracted with $CH_2Cl_2$ (3×15 mL). The aqueous phase is evaporated to dryness; the residue is recrystallized from conc. HCl/ethanol, to yield the title ligand as dihydrochloride (4.08 g, 91.0%).

$^1$H-NMR ($CDCl_3$)

1.14 (d, 6H, J=6.3 Hz), 1.17 (d, 6H, J=6.3 Hz), 1.33 (s, 3H), 3.21 (AB, 4H, J=15.1 Hz), 3.57 (sept, 2H, J=6.3 Hz), 3.68 (s, 8H).

MS (FAB$^+$) 420 (MH$^+$), 442 (MNa$^+$), 458 (MK$^+$) [Calc. for $C_{13}H_{33}N_3O_8$: 419.47].

Anal. Calc. for $C_{18}H_{33}N_3O_8$·2HCl (492.39): C, 43.91; H, 7.16; N, 8.57. Found: C, 43.66; H, 7.30; N, 8.41.

MS (FAB$^+$) 420 (MH$^+$), 442 (MNa$^+$), 458 (MK$^+$) [Calc. for $C_{18}H_{33}N_3O_8$: 419.47].

Anal. Calc. for $C_{18}H_{33}N_3O_8 \cdot 2HCl$ (492.39): C, 43.91; H, 7.16; N, 8.57. Found: C, 43.66; H, 7.30; N, 8.41.

EXAMPLE 3

Stability Properties of the Gd(III) Complex of Example 1

Potentiometric Measurements

All the pH metric measurements (pH=−log [H+]) were carried out in degassed 0.1 mol dm$^{-3}$ NMe$_4$NO$_3$ solutions, at 298.1 K, by using a Metrohm 670 Titroprocessor equipped with a Metrohm 6.0203.100 combined pH electrode. Prior to each potentiometric titration, the combined Metrohm electrode was calibrated as a hydrogen concentration probe by titrating known amounts of HCl with CO$_2$-free NMe$_4$OH solutions and determining the equivalent point by the Gran's method which allows to determine the standard potential $E^O$, and the ionic product of water. In the complexation experiments the metal ion concentration was about 80% of the ligand concentration. At least three measurements (about 100 data points each one) were performed for each system in the pH range 2.5-10.5 and the relevant e.m.f. data were treated by means of the computer programs SUPERQUAD and HYPERQUAD which furnished the protonation and the complexation constants.

| Reaction | Log $K_H$ |
|---|---|
| H + L = HL | 11.80 (2) |
| HL + H = H$_2$L | 6.55 (2) |
| H$_2$L + H = H$_3$L | 4.09 (3) |
| H$_3$L + H = H$_4$L | 2.60 (3) |
| H$_4$L + H = H$_5$L | 1.44 (4) |

| Reaction | Log$K_{Gd}$ |
|---|---|
| M + L = ML | 21.52 (1) |

Log$K_{Gd}$ (conditional, pH 7.4) = 17.06

Relaxometric Properties of the Gd(III) Complex of Example 1.

The relaxivity determined at 25° C., pH 7 and 20 MHz for said complex is 7.1 mM$^{-1}$s$^{-}$.

The exchange time ($t_M$) value of the Gd(III) complex of the example 1 has been assessed by measuring the transverse water $^{17}$O NMR relaxation time at variable temperature according to the procedure described by Aime et al., in the above cited literature. The results are set forth in FIG. 1.

Obtained value turned out to be 90 ns at 298 K. Albeit the optimal value (about 30 ns) has not been attained, this exchange rate can be considered quite fast, especially if compared with that of (Gd-DO3A), the Gd(III) compsex of reference, with two water molecules in the inner sphere, whose $t_M$ value is 160 ns.

Figure 2:
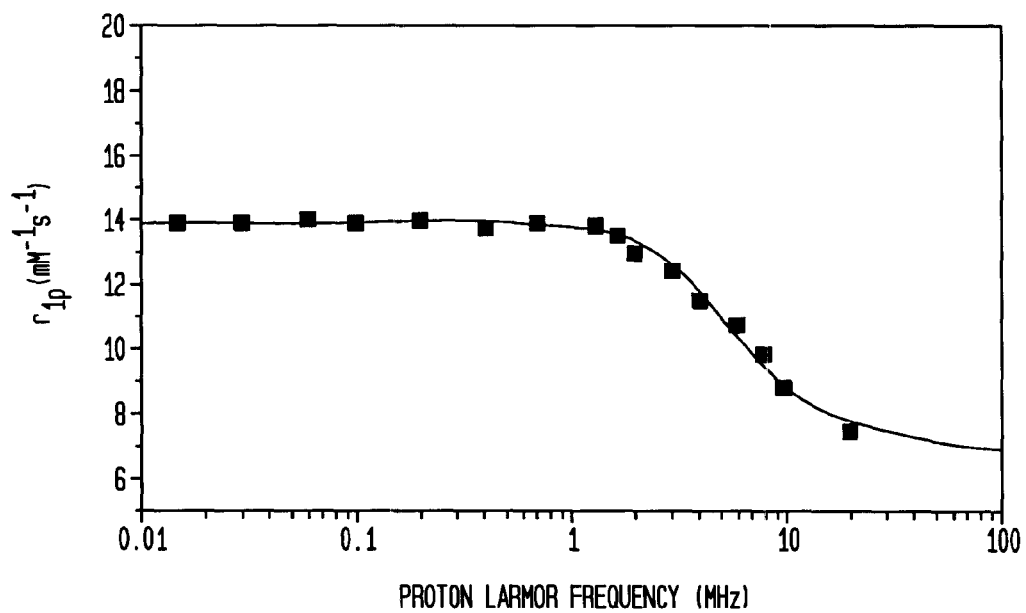
FIG. 2 shows the NMRD profile of the Gd(III) complex of EXAMPLE 1.

FIG. 2 shows the NMRD profile of the Gd(III) complex of the example 1, from whose fitting we could calculate a $t_R$ (the molecular reorientational time) value of 80 ps and electronic relaxation time values similar to those of other small-sized Gd(III) complexes (see Merbac A. E., cited above).

Figure 3:
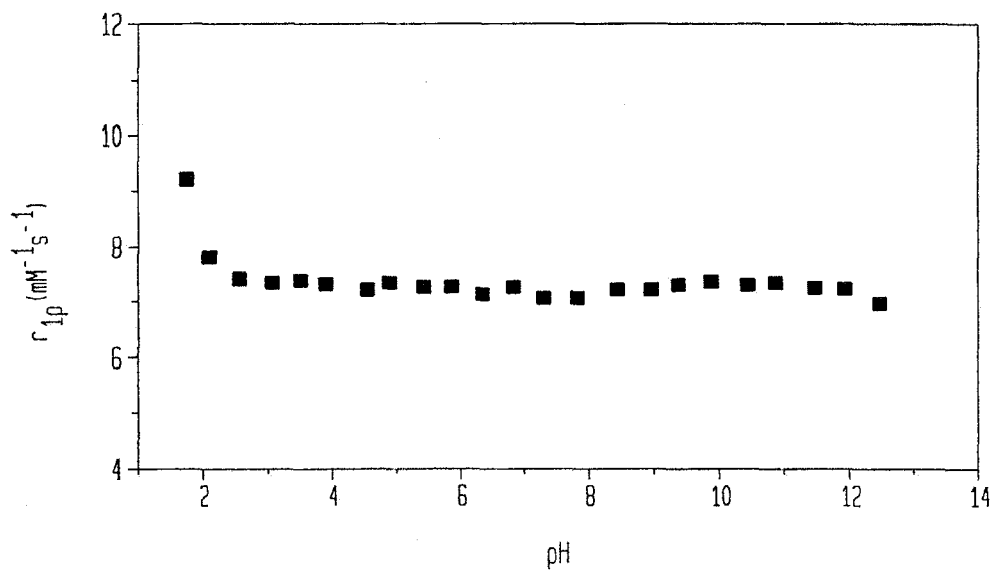
FIG. 3 shows the relaxivity of the Gd(III) complex of EXAMPLE 1 as a function of the pH.

The relaxivity of this complex was further tested as a function of the pH. FIG. 3 shows the obtained results.

Surprisingly enough, the relaxation rate of the tested complex compound was found to be substantially constant over all the investigated pH range. This result clearly indicates that the Gd complex with the ligands of the invention shows a low affinity for hydroxyl and carbamate anions present in solution at basic pH. On the contrary, they would have remarkably reduced the measured relaxivity.

Figure 4:
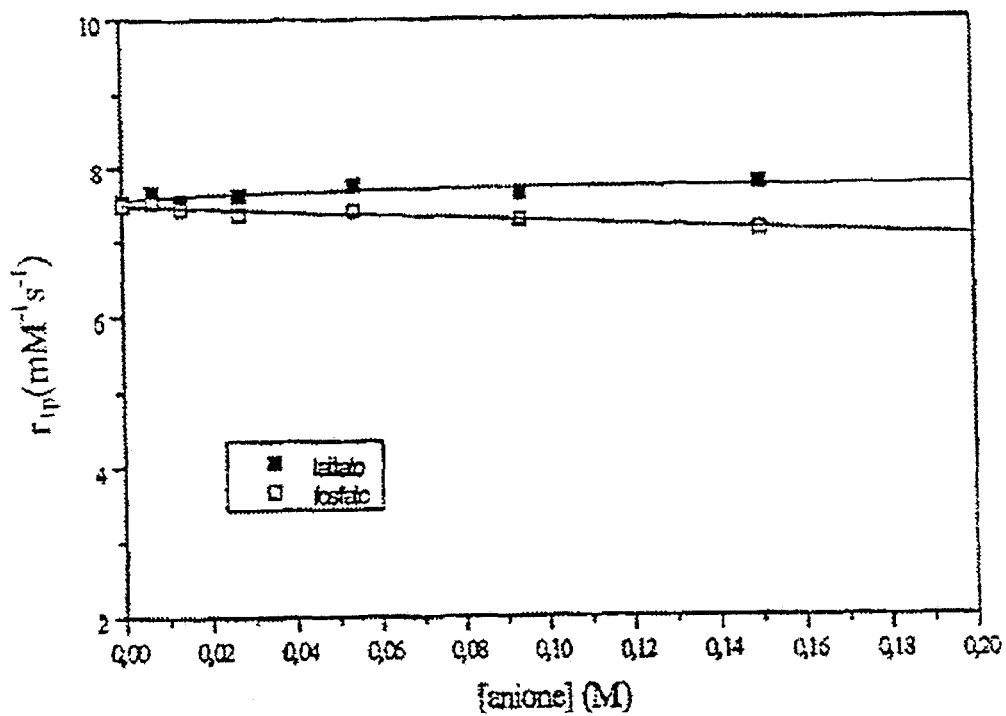
FIG. 4 shows the affinity of the compound of EXAMPLE 1 for lactate and phosphate ions.

A test, to further evaluate the lack of formation of ternary complexes was performed. As a non-limiting example, we measured the affinity of the compound of example 1 for lactate and phosphate ions. The determination was performed directly by adding increasing amounts of each anion to a 1 mM solution of the Gd(III) complex. The obtained results, shown in FIG. 4, indicate the complete absence of interaction even in presence of high concentration of bidentate endogenous anions.

Conversely analogous titrations of Gd-DO3A and Gd-DO3MA (both endowed with q=2) with lactate ions yielded $K_A$ values of 150 M$^{-1}$ and 110 M$^{-1}$, respectively.

The Gd complex of Ligand 1, which does not show any measurable association constant, is definitely the complex having lower affinity for this anion.

This result shows that the relaxivity of the Gd-complexes with the ligands of the invention is not "lowered" even in the presence of high concentrations of bidentate endogenous anions.

Furthermore, the high exchange rate of coordinated water makes this type of paramagnetic complexes particularly interesting for obtaining high relaxivities (r1 and/or r2) once their molecular motion is slowed for example through binding with macromolecules. As it is known by those skilled in the art, a number of procedures are available to carry out the binding (both covalent and non-covalent) of a ligand and/or of a metal complex thereof (both covalent and non-covalent) with the concerned molecules.

EXAMPLE 4

Compound for Attaching Targeting Moieties at R$_2$

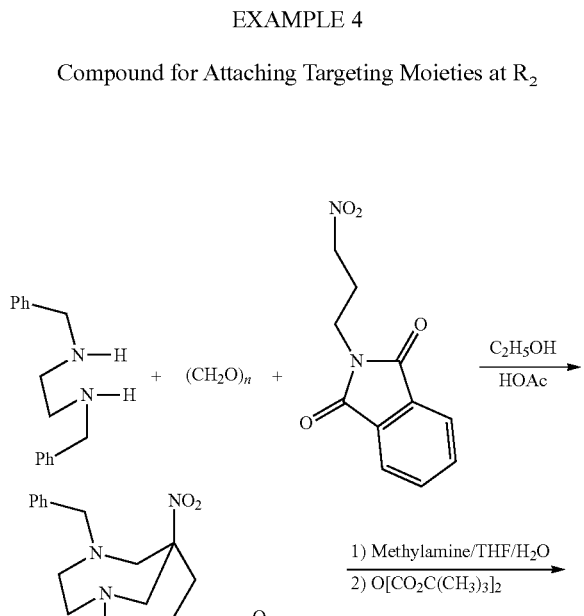

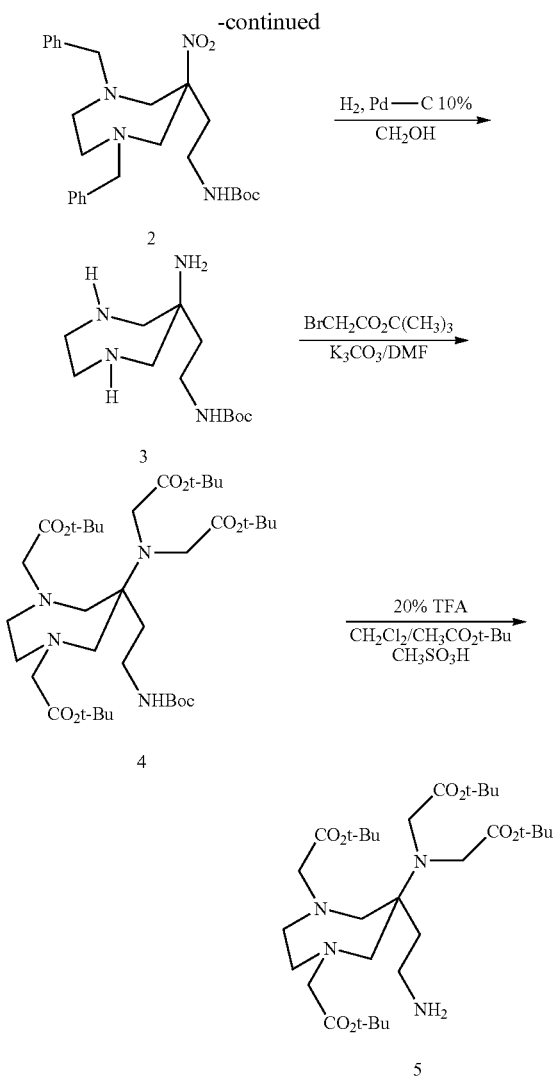

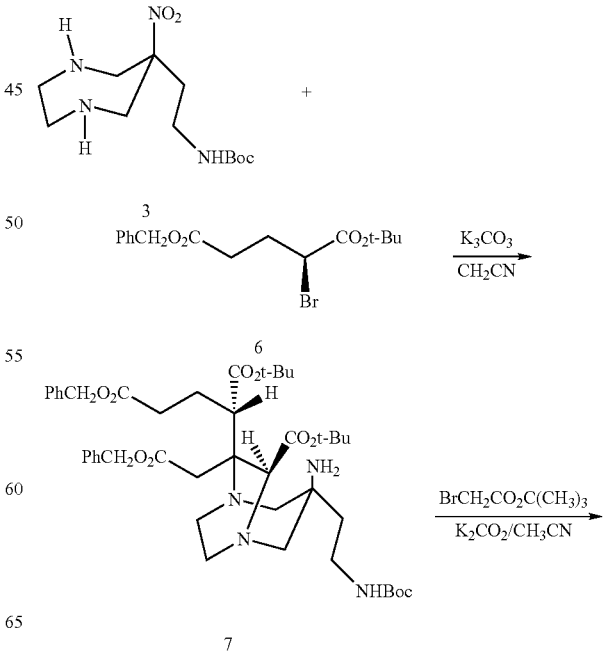

using hexane-ethyl acetate (7:3). UV visible fractions were collected and evaporated to give 2, as an oil. Yield 18.20 g (92%).

MS: 469.2 (M+H).

Compound (3). Pd—C 10% (750 mg) was added to a solution of the nitro compound 2 (2.0 g, 4.27 mmol) in methanol (40 mL), and the mixture was hydrogenated at 45 psi for 24 h. The catalyst was removed by filtration and methanol was removed on a rotary evaporator to give the amine 3 as a thick oil. Yield 1.0 g (91%).

MS: 259.2 (M+H).

Compound (4). tert-Butyl bromoacetate (3.8 g, 2.88 mL, 19.5 mmol) was added to a mixture of the amine 3 (1.0 g, 3.87 mmol) and potassium carbonate (2.69 g, 19.5 mmol) in DMF (4 mL) and the mixture was stirred at 40° C. for 12 h. DMF was removed under vacuum and the oil obtained was dissolved in ethyl acetate (150.0 mL), washed with water and dried. ($Na_2SO_4$). Evaporation of ethyl acetate gave an oil which was purified by column chromatography using hexane-ethyl acetate (7:3). Product containing fractions (Rf 0.7) were collected and evaporated to give a thick oil. Yield 1.10 g (40%).

MS: 715.5 (M+H), 737.4 (M+Na)

Compound (5). Boc derivative 4 (0.82 g 1.15 mmol) was added to a mixture of methylene chloride (5 mL), t-butyl acetate (15 mL), and TFA (4 mL) and the mixture was stirred for 10 min. Methanesulfonic acid (300 μL) in methylene chloride (1 mL) was added in portions over a period of 10 min and stirred for 12 h. The solution was neutralized by sodium bicarbonate solution and extracted with ethyl acetate. The ethyl acetate solution was washed with water and dried ($Na_2SO_4$). Evaporation of ethyl acetate gave an oil which was dried under vacuum to give a foamy solid. Yield 0.7 g (99%).

MS: 615.4 (M+H).

EXAMPLE 5

Compound for Derivatization at $R_2$ with Additional Derivatization Possible at $R_3$ Compound (1). Acetic acid (6.0 mL) was added to a solution of N,N-dibenzylethylene diamine (12.18 g, 50.6 mmol) in ethanol (80 mL) and the solution was stirred at 60° C. for 10 min (A white solid formed which dissolved on heating to 80° C.). N-(3-nitropropyl) phthalimidel (11.7 g, 50.0 mmol) was added and the stirring was continued at 80° C. to obtain a clear solution. Paraformaldehyde (5.0 g, 1166 mmol) was added to this solution in small portions over a period of 30 min and the stirring continued for 5 h at 80° C. The reaction mixture was cooled and the solid formed was filtered, washed with cold ethanol and dried under vacuum. Yield 22.0 g (88%).

MS: 499.5 (M+H).

Compound (2). Phthalimido derivative 1 (21.0 g, 42.0 mmol) was added to a mixture of $CH_3NH_2$/THF (40.0 mL) $CH_3NH_2/H_2O$ (80 mL) and stirred at room temperature for 48 h. Excess methylamine was removed by passing a stream of nitrogen and the solvent was removed under vacuum. The solid obtained was dissolved in a mixture of tetrahydrofuran (100 mL) and water (10 mL). Di-tert-butyl dicarbonate (19.0 g, 87.0 mmol) was added to the THF-water solution and stirred for 16 h. Solvents were removed and the pasty solid obtained was dissolved in ethyl acetate (400 mL), washed with sodium chloride solution (2×200 mL) and dried ($Na_2SO_4$). Evaporation of ethyl acetate gave a yellow oil, which was purified by silica gel column chromatography

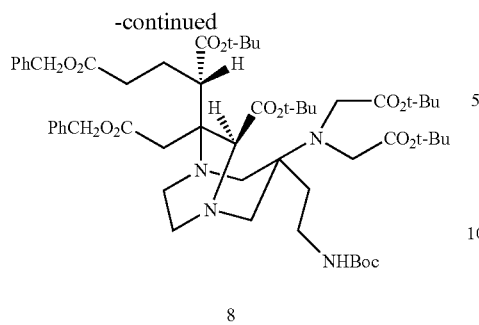

8

Compound (7). Bromo-ester[2] 6 (0.8 g, 2.24 mmol) was added to a mixture of the amine 3 (0.26 g, 1.0 mmol) and potassium carbonate (0.5 g, 3.62 mmol) in acetonitrile (4 mL) and the mixture was stirred for 8 h. The reaction mixture was filtered and acetonitrile was evaporated under vacuum. The thick oil obtained was dissolved in ethyl acetate, washed with water and dried ($Na_2SO_4$). Evaporation of ethyl acetate gave an oil which was purified by silica gel column chromatography using methylene chloride-methanol (95:5). Fractions (Rf 0.5) were collected and evaporated to give the ester 7 as an oil. Yield 0.3 g (37%).

MS: 811.4 (M+H), 849.3 (M+K)

Compound (8). tert-Butyl bromoacetate (0.29 g, 0.22 mL, 1.4 mmol) was added to a mixture of the amine 7 (0.3 g, 0.37 mmol), and potassium carbonate (0.2 g, 1.45 mmol) in acetonitrile (3 mL) and the mixture was stirred at 70° C. for 24 h. Acetonitrile (15 mL) was added to the reaction mixture and filtered. Acetonitrile was removed and the oil obtained was dissolved in ethyl acetate, washed with water (2×10 mL) and dried ($Na_2SO_4$). Evaporation of the solvent gave a brown oil, which was purified by column chromatography (silica gel, hexane-ethyl acetate, 7:3). UV visible fraction (Rf 0.45) were collected and evaporated to give 8, as an oil, which solidified on standing. Yield 0.27 g (70%).

MS: 1040.4 (M+H)

The final compound or a derivatized version including, e.g., a targeting moiety, may be de-protected and labeled with, for example, Gd or $^{177}$Lu, using procedures known in the art or disclosed herein.

EXAMPLE 6

Compound with Cyclohexyl at $R_1$ Allowing Derivativization at $R_2$

Compound 13 is particularly useful for attaching antibody targeting moieties (e.g., removing the Boc group and attaching an antibody using isothiocyanate).

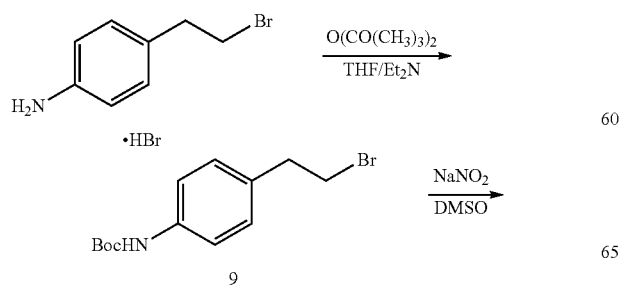

9

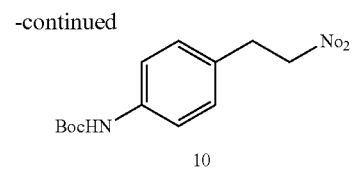

10

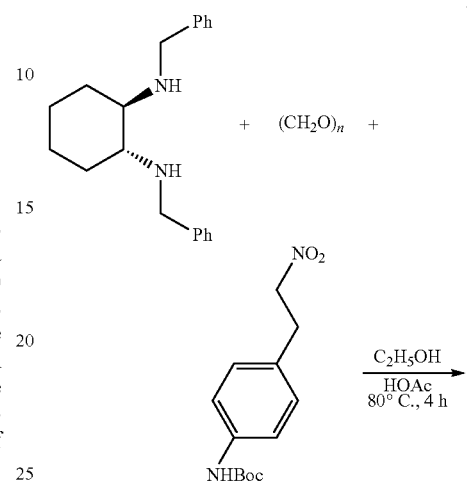

10

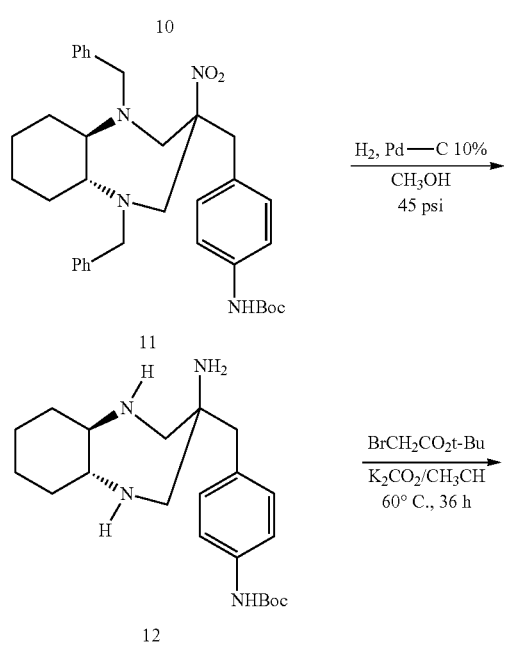

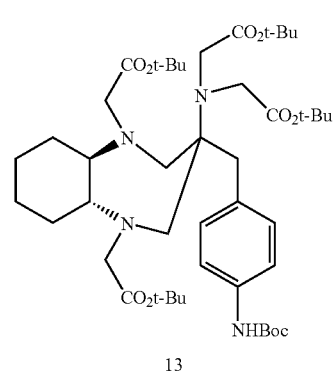

13

Compound (9). Di-tert-butyl dicarbonate (30.0 g 138 mmol) was added to a ice cooled mixture of p-aminophenylethyl bromide hydrobromide 3 (36.0 g, 128 mmol) and triethylamine (10 mL) and the mixture was stirred at room temperature for 24 h. Solvents were removed and the pasty solid was treated with water and extracted with ethyl acetate. Evaporation of ethyl acetate gave a solid, which was purified by column chromatography using hexane-ethyl acetate. UV visible fractions were collected and evaporated to give a white solid. Yield 34.2 g (88%)

MS: 324.2 (M+Na)

Compound (10). Compound 9 (3.0 g, 10.0 mmol) was added to a mixture of sodium nitrite (1.4 g, 20.0 mmol) in DMSO (5 mL), and the mixture was stirred for 2 h. A semi-solid was formed after 30 min. After the reaction, the mixture was poured in to water and extracted with ethyl acetate. The ethyl acetate solution was washed with water and dried ($Na_2SO_4$). Evaporation of ethyl acetate gave an yellow solid, which was purified by column chromatography using hexane-ethyl acetate (7:3). UV visible fractions were collected and evaporated to give a yellow solid. Yield 1.29 g (48.5%).

MS: 289.2 (M+Na)

Compound (11). Acetic acid (0.6 mL) was added to a solution of trans-N,N-dibenzyl-1,2-diaminocyclohexane[4] (1.43 g, 4.85 mmol) in ethanol (5.0 mL) and stirred at 60° C. for 10 min. Compound 10 (1.29 g, 4.84 mmol) was added to this solution and the stirring was continued at 60° C. for additional 10 min. Paraformaldehyde (0.5 g, 16.6 mmol) was added in small portions over a period of 30 min and the reaction mixture was stirred at 80° C. for 5 h. Ethanol was removed and the residue was extracted with ethyl acetate, washed with water and dried. Evaporation of ethyl acetate gave an oil, which was purified by silica gel column chromatography (hexane-ethyl acetate 7:3). UV visible fractions were collected and evaporated to give an oil. Yield 2.2 g (76%).

MS: 585.3 (M+H),

Compound (12). Pd—C 10% (1.0 g) was added to a warm slurry of compound 10 (2.1 g, 3.6 mmol) in methanol (40 mL) and the mixture was hydrogenated at 45 psi for 24 h at RT. The catalyst was removed by filtration and the solvent was removed under vacuum to give an oil which was used in the next step without further purification. Yield 1.28 g (95%).

MS: 375.3 (M+H), 389.4 (M+Na)

Compound (13). tert-Butyl bromoacetate (2.34 g, 1.78 mL, 12 mmol) was added to a solution of the amine 12 (0.75 g, 2.0 mmol) and potassium carbonate (1.66 g, 12.0 mmol) in DMF (4 mL) and the mixture was stirred at 70° C. for 24 h. Methylene chloride (10.0 mL) was added to the reaction mixture and filtered. The solvents were removed and the brown oil obtained was purified by silica gel column chromatography ($CH_2C_{12}$:$CH_2OH$, 95:5). UV visible fractions (Rf 0.48) were collected and evaporated to give an oil which solidified on standing. Yield 0.75 g, (45%).

MS: 831.5 (M+H).

The final compound or a derivatized version including, e.g. a targeting moiety, may be de-protected and labeled with, for example, Gd or $^{177}$Lu, using procedures known in the art or disclosed herein.

EXAMPLE 7

Compound with Cyclohexyl at $R_1$, Amine at $R_2$ for Coupling (I.E., Derivatization at the Amine)

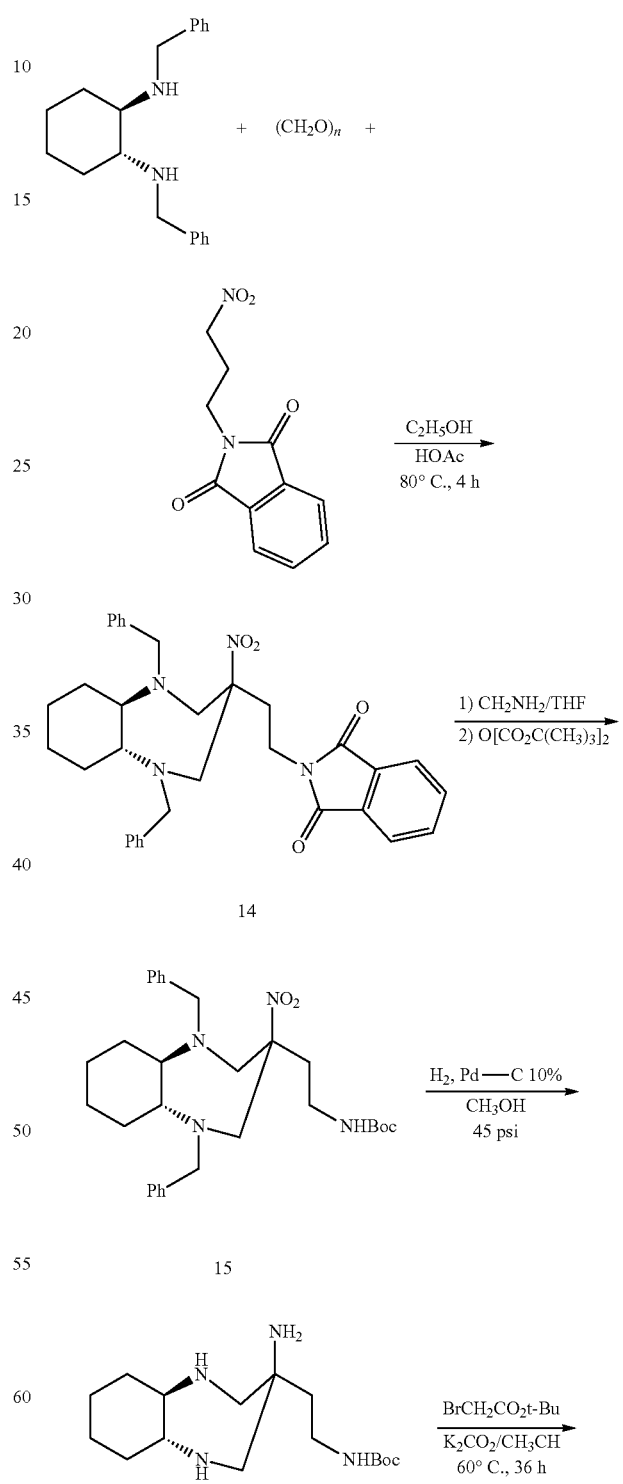

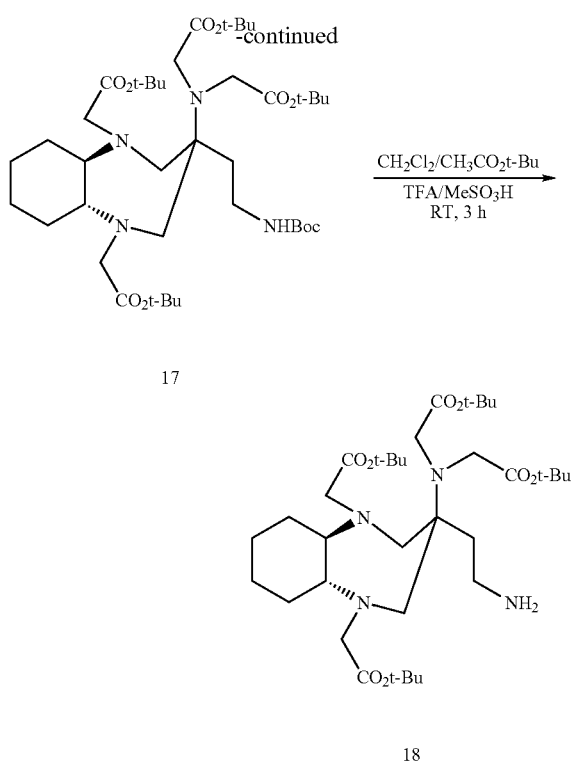

17

18

Compound (14). Acetic acid (3.60 mL) was added to a solution of trans-N,N-dibenzyl-1,2-diaminocyclohexane (8.82 g, 30.0 mmol) in ethanol (60 mL) and the solution was stirred at 60° C. for 10 min. N-(3-nitropropyl) phthalimide (7.1 g, 30.3 mmol) was added and the stirring was continued at 60° C. for additional 30 min. Paraformaldehyde (3.75 g, 126 mmol) was added to this solution in small portions over a period of 30 min and the stirring was continued for 5 h at 80° C. Ethanol was removed and the thick oil obtained was dissolved in ethyl acetate (200 mL) and the ethyl acetate solution was washed with sodium bicarbonate solution, water and dried ($Na_2SO_4$). Ethyl acetate solution was concentrated and the resulting oil was purified by silica gel column chromatography (7:3). Fractions (Rf 0.48) were collected and evaporated to give a thick yellow oil, which was dried under vacuum to give a foamy solid. The foamy solid obtained was dissolved in methanol (50.0 mL) and allowed to stand for 30 min. The solid formed was filtered, washed with cold ethanol and dried under vacuum. Yield 8.3 g (50.0%).

MS: 553.3 (M+H).

Compound (15). Phthalimido derivative 14 (8.0 g, 14.5 mmol) was added to a mixture of 2 M solution of $CH_3NH_2$ in THF (75 mL) and 40% solution of $CH_3NH_2$ in H2O (30 mL) and the mixture was stirred at room temperature for 48 h. Excess methylamine was removed by passing a stream of nitrogen and the solvent was removed under vacuum. The yellow solid obtained was dissolved in a mixture of tetrahydrofuran (100 mL) and water (10 mL). Di-tert-butyl dicarbonate (8.72 g, 40.0 mmol) was added to the THF solution and stirred for 6 h. THF was removed and the pasty solid obtained was dissolved in ethyl acetate (300 mL), washed with sodium carbonate solution, then washed with sodium chloride solution (2×200 mL) and dried ($Na_2SO_4$). Evaporation of ethyl acetate gave an yellow oil which was purified by silica gel column chromatography using hexane-ethyl acetate (9:1, and 8:2). UV visible fractions were collected and evaporated to give 14 as an oil. The oil obtained was dissolved in methanol (50 mL) and allowed to stand for 1 h. The white solid formed was filtered and dried under vacuum. Yield 5.1 g (67.5%).

MS: 523.3 (M+H).

Compound (16). Compound 14 (4.80 g, 9.2 mmol) in methanol (50 mL), was hydrogenated at 45 psi for 72 h in the presence of Pd—C 10% (2.0 g). The catalyst was removed by filtration and methanol was removed under reduced pressure to give 2.6 g (90%) of the amine 16.

MS: 313.2 (M+H).

Compound (17). tert-Butyl bromoacetate (3.51 g, 2.65 mL, 18.0 mmol) was added to a slurry of potassium carbonate (2.5 g, 18.0 mmol) and amine 16 (0.93 g, 3.0 mmol) in DMF (4 mL) and the mixture was stirred at 70° C. for 24 h. Methylene chloride (10 mL) was then added to the reaction mixture and filtered. The solvents were removed and the brown oil obtained was purified by silica gel column chromatography (hexane-ethyl acetate 7:3). Fractions (Rf 0.48) were collected and evaporated to give an oil, which solidified on standing. Yield 1.1 g, (48.0%).

MS: 769.5 (M+H).

Compound (18). Boc derivative 4 (1.1 g 1.43 mmol) was added to a mixture of methylene chloride (5 mL), t-butyl acetate (25 mL), and TFA (5 mL) and the mixture was stirred for 10 min. Methanesulfonic acid (400 μL) in methylene chloride (1 mL) was added in portions over a period of 10 min and the reaction was allowed to stir for 3 h. The solution was neutralized by sodium bicarbonate solution and extracted with ethyl acetate. The ethyl acetate solution was washed with water and dried ($Na_2SO_4$). Evaporation of ethyl acetate gave an oil, which was dried under vacuum to give a foamy solid. Yield 0.82 g (99%).

MS: 669 (M+H).

The final compound or a derivatized version including, e.g., a targeting moiety, may be de-protected and labeled with, for example, Gd or $^{177}$Lu, using procedures known in the art or disclosed herein.

EXAMPLE 8

Compound Including a Carboxylic Acid for Dervitization at $R_2$

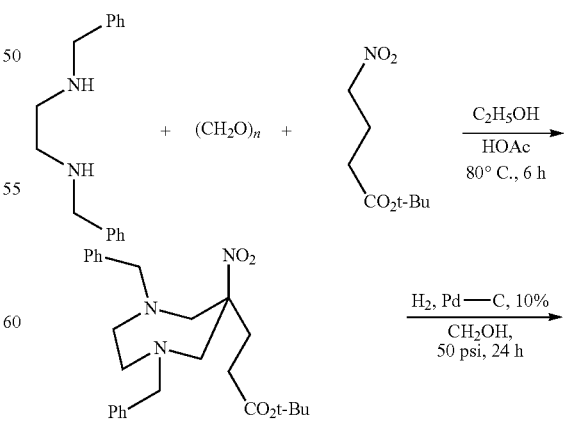

19

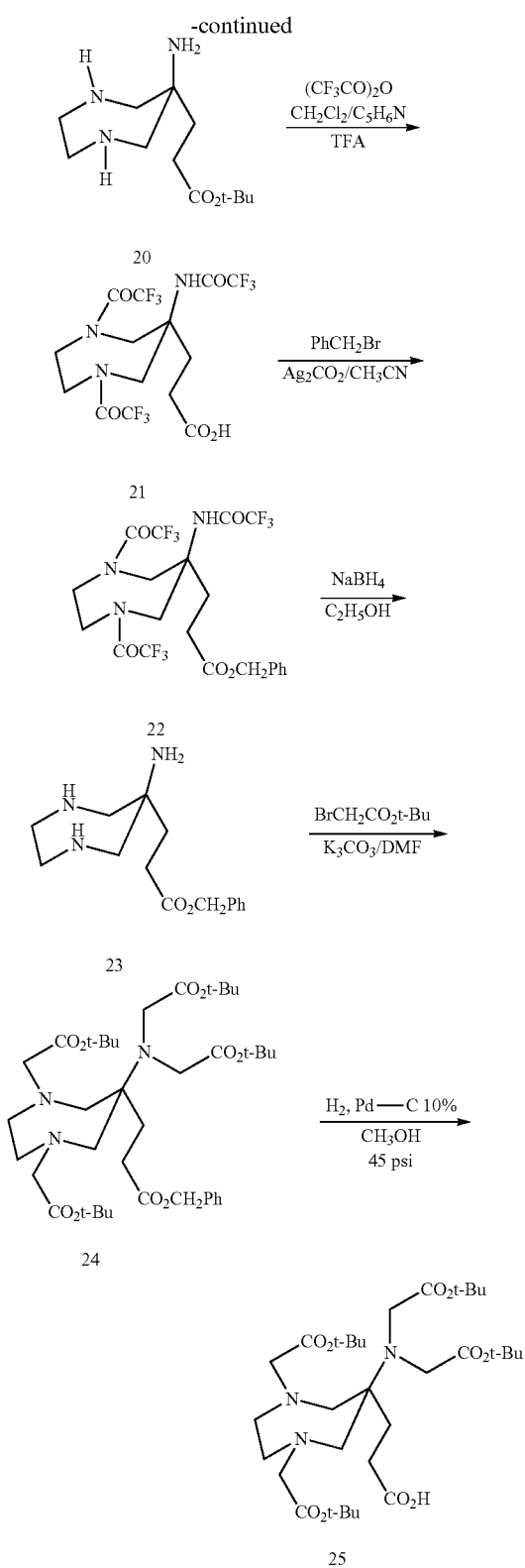

tinued at 60° C. for additional 10 min. Paraformaldehyde (2.5 g, 83 mmol) was added in portions to the reaction mixture and the suspension was stirred at 80° C. for 5 h and at RT overnight. The dark reaction mixture was concentrated and the residue was treated with a solution of sodium bicarbonate and extracted with ethyl acetate (400 mL). The ethyl acetate solution was washed with water (2×200 mL) and dried ($Na_2SO_4$). Evaporation of ethyl acetate gave a dark thick oil. It was purified by silica gel column chromatography using methylene chloride. UV visible fractions were collected and evaporated to give a light yellow oil, which solidified on standing. Yield 8.9 g (86.5%).

MS: 454.3 (M+H)

Compound (20). Pd—C 10%, (2.0 g) was added to a solution of the nitro compound 19 (4.5 g, 10 mmol) in methanol (25 mL) and the mixture was hydrogenated at 50 psi for 24 h. The catalyst was removed by filtration and the methanol was removed on a rotary evaporator. The oil obtained was dried under vacuum for 24 h to give the amine 20. Yield 2.2 g (92%).

MS: 244.2 (M+H)

Compound (21). Pyridine (15.0 mL) was added to a solution of the amine 20 (3.5 g, 14.4 mmol) in methylene chloride (25.0 mL) and the mixture was cooled to −10° C. Trifluoroacetic anhydride (22.7 g, 15.25 mL, 108 mmol) in methylene chloride (25.0 mL) was added dropwise over a period of 30 min. The reaction mixture was stirred at 0° C. for 3 h and at room temperature for 12 h. Solvents were removed and the pasty mass obtained was dissolved in ethyl acetate (200 mL) and the washed with water and dried ($Na_2SO_4$). Evaporation of ethyl acetate gave an yellow oil, which was dried under vacuum to yield a foamy solid. Yield 6.92 g (90%).

Trifluoroacetic acid (15 mL) was added to a solution of the t-butyl ester (5.0 g, 9.4 mmol) in methylene chloride (10 mL) and the solution was stirred for 6 h. Solvents were removed and the resulting brown oil was dissolved in ethyl acetate, washed with water and dried ($Na_2SO_4$). Ethyl acetate solution was concentrated and the residue was dried under vacuum to give 21 as a yellow foamy solid. Yield 4.23 g (95%).

MS: 474.1 (M−H)

Compound (22). Silver carbonate (3.43 g, 12.4 mmol) was added to a solution of the acid 21 (4.2 g, 8.8 mmol) in acetonitrile (15 mL) and the mixture was stirred for 10 min. Benzyl bromide (3.42 g, 2.4 mL, 12.4 mmol) was then added to the reaction mixture and stirring was continued for 5 h. Methylene chloride (25 mL) was added to the reaction mixture and filtered. The filter cake was washed with methylene chloride (15.0 mL). The filtrate was concentrated and the brown oil obtained was purified by column chromatography (silica gel, hexane-ethyl acetate, 7:3). Fractions (Rf 0.45) were collected and evaporated to give a light yellow oil which, was dried under vacuum to give a light yellow solid. Yield 4.2 g (84%).

MS: 588.1 (M+Na)

Compound (23). Sodium borohydride (0.23 g, 6.0 mmol) was added to a cooled slurry of the trifluoroacetamide 22 (0.57 g, 1.0 mmol) in absolute ethanol (5 mL), in two portions. The reaction mixture was stirred at 10° C. for 30 min and room temperature for 30 min. Ethanolic HCl was then added to the reaction mixture and the solvent was removed to give 0.72 g of the crude product. It was used in the next step without further purification, MS: 278.2 (M+H), 300.1 (M+Na)

Compound (24). tert-Butyl bromoacetate (1.17 g, 0.89 mL, 6.0 mmol) was added to a slurry of hydrochloride 23 (0.72 g, 1.0 mmol) and potassium carbonate (0.83 g, 6.0 mmol) in DMF (1 mL) and the mixture was stirred at 40° C. for 24 h. Methylene chloride (5 mL) was added to the reaction mixture and filtered. Solvents were removed under vacuum and the Compound (19). Acetic acid (3 mL) was added to a solution of N,N'-dibenzylethylene diamine (6.0 g, 25 mmol) in ethanol (40 mL) and the mixture was stirred at 60° C. for 10 min. 4-Nitrobutyric acid t-butyl ester (4.73 g, 25 mmol) was then added to the reaction mixture and the stirring was concrude product was dissolved in ethyl acetate, washed with water, and dried (Na$_2$SO$_4$). Evaporation of the ethyl acetate gave an oil which, was purified by silica gel column chromatography (hexane-ethyl acetate, 7:3). Fractions (Rf 0.5) were collected and evaporated to give the benzyl ester 24 as a light yellow oil. Yield 0.12 g (17%).

MS: 734.4 (M+H), 756.4 (M+Na)

Compound (25). Benzyl ester 24 (0.15 g, 0.2 mmol) in methanol (5 mL) was hydrogenated in the presence of Pd—C 10% (150 mg) at 45 psi for 6 h. The catalyst was removed by filtration and the methanolic solution was concentrated to give an oil. It was dried under vacuum to give foamy solid. Yield 0.11 g (83%).

MS: 644.4 (M+H)

The final compound or a derivatized version including, e.g., a targeting moiety, may be de-protected and labeled with, for example, Gd or $^{177}$Lu, using procedures known in the art or disclosed herein.

EXAMPLE 9

Compound Including Cyclohexyl at $R_1$, Carboxylic Acid at $R_2$ for Derivatization

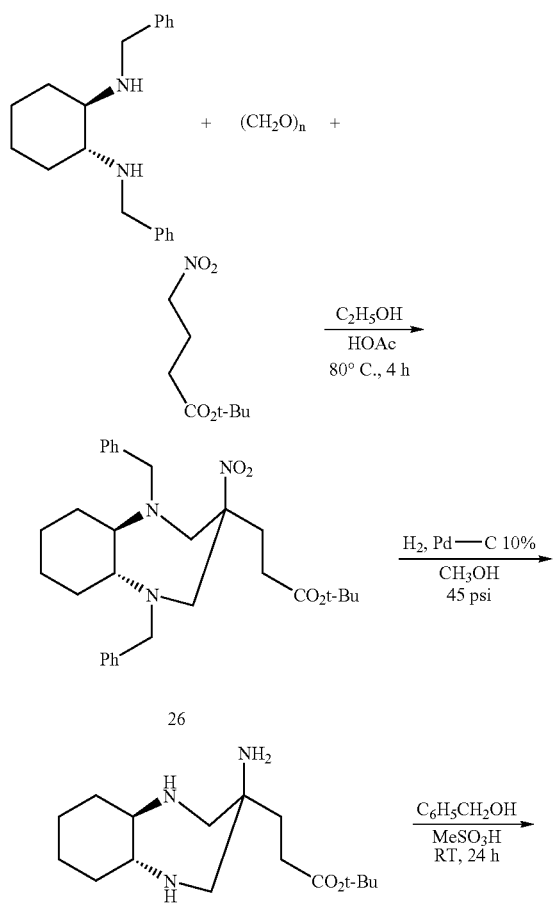

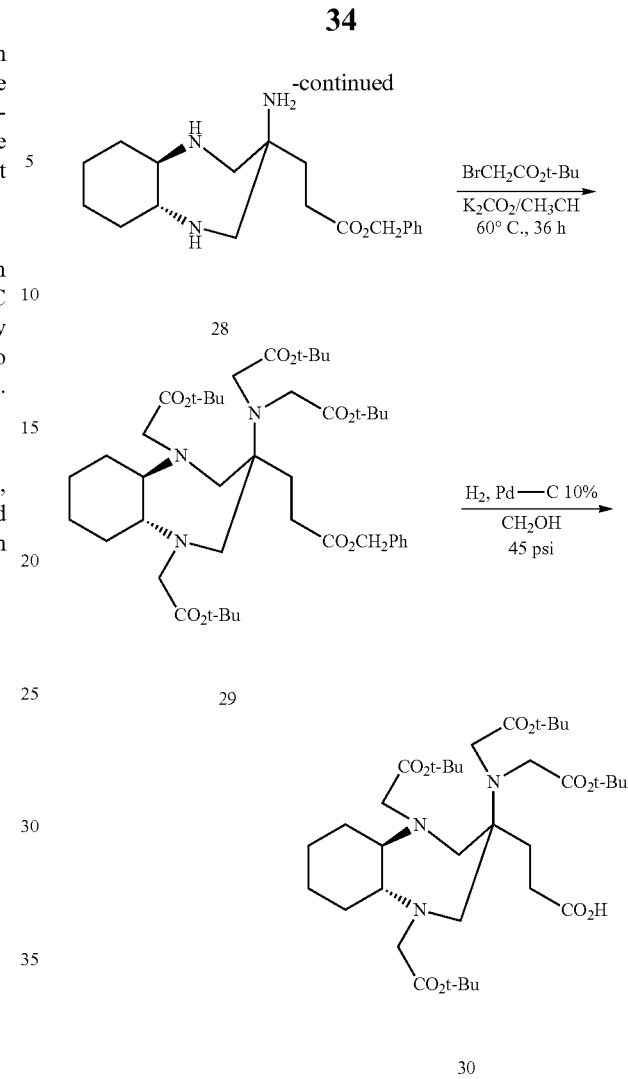

Compound (26). Acetic acid (4.5 mL, 75 mmol) was added to a solution of trans-N,N-dibenzyl-1,2-diaminocyclohexane (10.87 g, 0.037 mmol) in ethanol (50 mL), and stirred at 60° C. for 10 min. 4-Nitrobutyric acid-t-butyl ester (7.1 g, 37.5 mmol) was then added and the stirring was continued for additional 10 min. Paraformaldehyde (3.37 g, 125 mmol) was added in portions over a period of 30 min and stirred at 80° C. for 6 h. The reaction mixture was cooled and the solid formed was filtered and washed with ethanol and dried under vacuum. Yield 9.2 g (49%).

MS: 508 (M+H).

Compound (27). Pd—C 10%, (2.0 g) was added to a warm solution of the nitro compound 26 (5.1 g, 10 mmol) in methanol (50 mL) and the mixture was hydrogenated at 50 psi for 24 h. The catalyst was removed by filtration and the methanol was removed to give 2.92 g (98%) of the amine 27.

MS: 298 (M+H).

Compound (28). Methanesulfonic acid (1.0 mL) was added to a solution of the t-butyl ester 27 (1.0 g, 3.37 mmol) in benzyl alcohol (20 mL)) and the mixture was stirred for 24 h. THF (100 mL) was added to the reaction mixture and the solid formed was filtered and triturated with THF (2×50 mL) and filtered.

The crude benzylester obtained was used in the next step. Yield 1.2 g (57%).

MS: 332.3 (M+H).

Compound (29). tert-Butyl bromoacetate (0.51 g, 0.39 mL, 2.6 mmol) was added to a mixture of 28 (0.15 g, 0.45 mmol)

and potassium carbonate (0.5 g, 3.7 mmol) in DMF (4 mL) and the mixture was stirred for 48 h. Methylene chloride (10 mL) was added to the reaction mixture and the solvents were removed to give an oil. The oil obtained was chromatographed over silica gel using methylene chloride, then methylene chloride-methanol (95:5). Fractions containing the product (Rf 0.4) were collected and evaporated to give an oil. Yield 0.15 g (43%).

MS: 788.6 (M+H), 826.4 (M+K)

Compound (30). Pd—C 10% (250 mg) was added to a solution of the benzyl ester (0.4 g, 0.19 mmol) in methanol (10 mL) and the mixture was hydrogenated at 45 psi for 6 h. The catalyst was removed by filtration and the methanolic solution was concentrated to give an oil which was dried under vacuum to give a foamy solid. Yield 0.32 g (92%).

MS: 698.4 (M+H),

The final compound or a derivatized version including, e.g., a targeting moiety, may be de-protected and labeled with, for example, Gd or $^{177}$Lu, using procedures known in the art or disclosed herein.

EXAMPLE 10

Two $R_2$ Groups Join to Form a Dimer

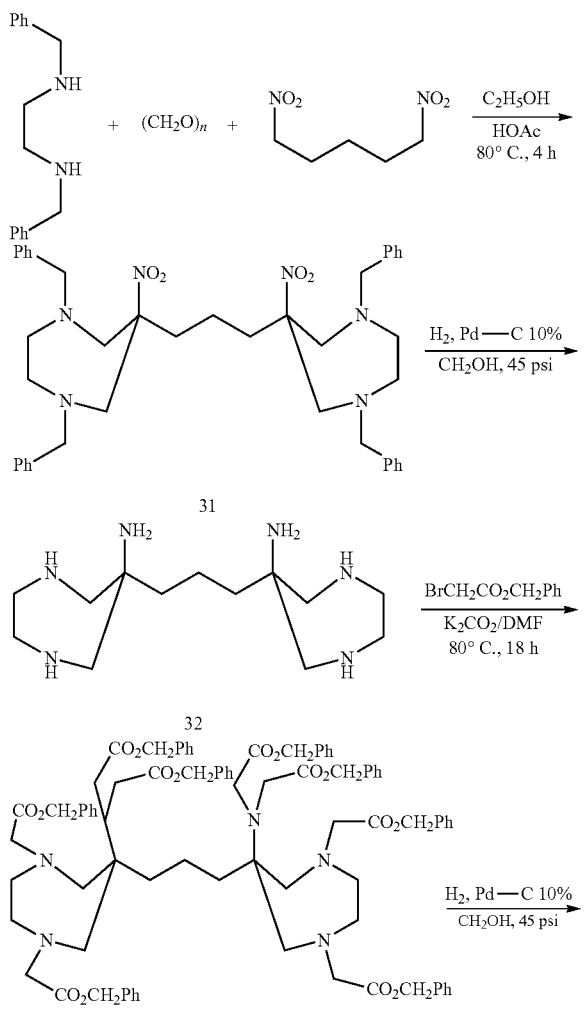

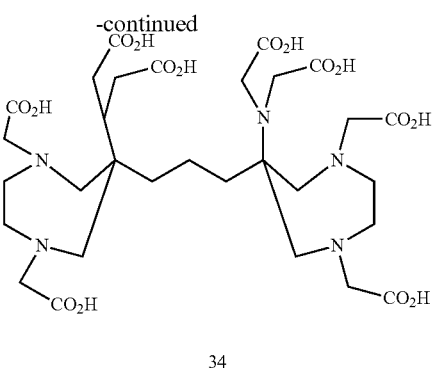

34

Compound (31). Acetic acid (3 mL) was added to a solution of N,N-dibenzylethylene diamine (6.0 g, 25.3 mmol) in ethanol (40 mL) and the solution was stirred at 60° C. for 10 min. A white solid formed which dissolved on heating to 80° C. 1,5-Dinitropentane (2.03 g, 12.5 mmol) was added and the stirring was continued at 60° C. for additional 10 min. Paraformaldehyde (5.0 g, 166 mmol) was added to this solution in small portions over a period of 30 min and the suspension was stirred for 5 h at 80° C. The reaction mixture was cooled and the solid formed was filtered, washed with cold ethanol and dried under vacuum. Yield 6.0 g (70%).

MS: 691.4 (M+H).

Compound (32). Pd—C 10% (750 mg) was added to a hot slurry of the nitro compound 31 (1.0 g, 1.45 mmol) in methanol (50 mL), and the mixture was hydrogenated at 45 psi for 24 h. The catalyst was removed by filtration and methanol was removed on a rotary evaporator to give the amine 32 as a thick oil. Yield 0.38 g (97%).

MS: 271.3 (M+H).

Compound (33). Benzyl 2-bromoacetate (3.76 g, 2.2 mL, 16.6 mmol) was added to a mixture of the amine 32 (0.45 g, 1.66 mmol) and potassium carbonate (2.69 g, 16.6 mmol) in DMF (4 mL) and the mixture was stirred at 70° C. for 18 h. DMF was removed under vacuum and the oil obtained was dissolved in ethyl acetate (150.0 mL), washed with water and dried. (Na$_2$SO$_4$). Evaporation of ethyl acetate gave an oil, which was purified by column chromatography using hexane-ethyl acetate (7:3). Product containing fractions (Rf 0.7) were collected and evaporated to give a thick oil. The thick oil obtained was further purified by preparative HPLC (CH3CN/H2O/0.1% TFA). Fractions containing the pure product were collected and freeze dried to give 33 as a glassy solid. Yield 0.42 g (17.0%).

MS: 1455.7 (M+H), 1477.6 (M+Na)

Compound (34). Pd—C 10% (750 mg) was added to a solution of the benzylester 31 (0.3 g, 0.2 mmol) in methanol (50 mL), and the mixture was hydrogenated at 45 psi for 24 h. The catalyst was removed by filtration and methanol was removed to give the amine 32 as a thick oil. The oil obtained was dissolved in a mixture of acetonitrile and water and freeze dried to give compound 34 as a white solid. Yield 0.11 g (75%).

MS: 733.3 (M−H), 366.2 (M−2H/2)

The final compound, a dimer, may be de-protected and labeled with, for example, Gd or $^{177}$Lu, using procedures known in the art or disclosed herein. To allow attachment of a targeting molecule, optionally the alkyl linker between the two compounds of Formula I can be further substituted with an amino alkyl or carboxy alkyl group that would allow attachment of a targeting moity.

General procedure for the synthesis of peptides. Synthesis of peptides was carried out on a 0.25 mmol scale using ABI 433 A synthesizer with the FastMoc protocol (Applied Biosystems Inc.). In each cycle of this protocol, 1.0 mmol of a dry protected amino acid in a cartridge was dissolved in a solution of 0.9 mmol of HBTU, 2 mmol of DIEA, and 0.9 mmol of HOBt in DMF with additional NMP added. The peptides were made using 0.1 mmol of Fmoc-PAL-PEG-PS resin (resin substitution 0.18 mmol/g). The coupling time in this protocol was 21 min. Fmoc deprotection was carried out with 20% piperidine in NMP. The peptide bound resin was washed, dried and cleaved from the resin (using reagent B: TFA/triisopropylsilane/phenol/H20 8.6 mL, 0.4 mL, 0.5 g, 0.5 mL) for further manipulations or the cleaved peptides were cyclized in DMSO at pH 7.5-8.0 and purified by preparative HPLC using CH3CN/Water containing 0.1% Column: Water's X Terra, 50 mm×250 mm i.d.; C18, Particle size: 10 microns; Eluents: A: Water (0.1% TFA), B: acetonitrile (0.1% TFA); Elution: Initial condition: 10% B, linear gradient 10-70% B over 70 min; Flow rate: 100 mL/min; Detection: UV @ 220 nm.

EXAMPLE 11

Compound of the Invention Including a Fibrin-Binding Peptide

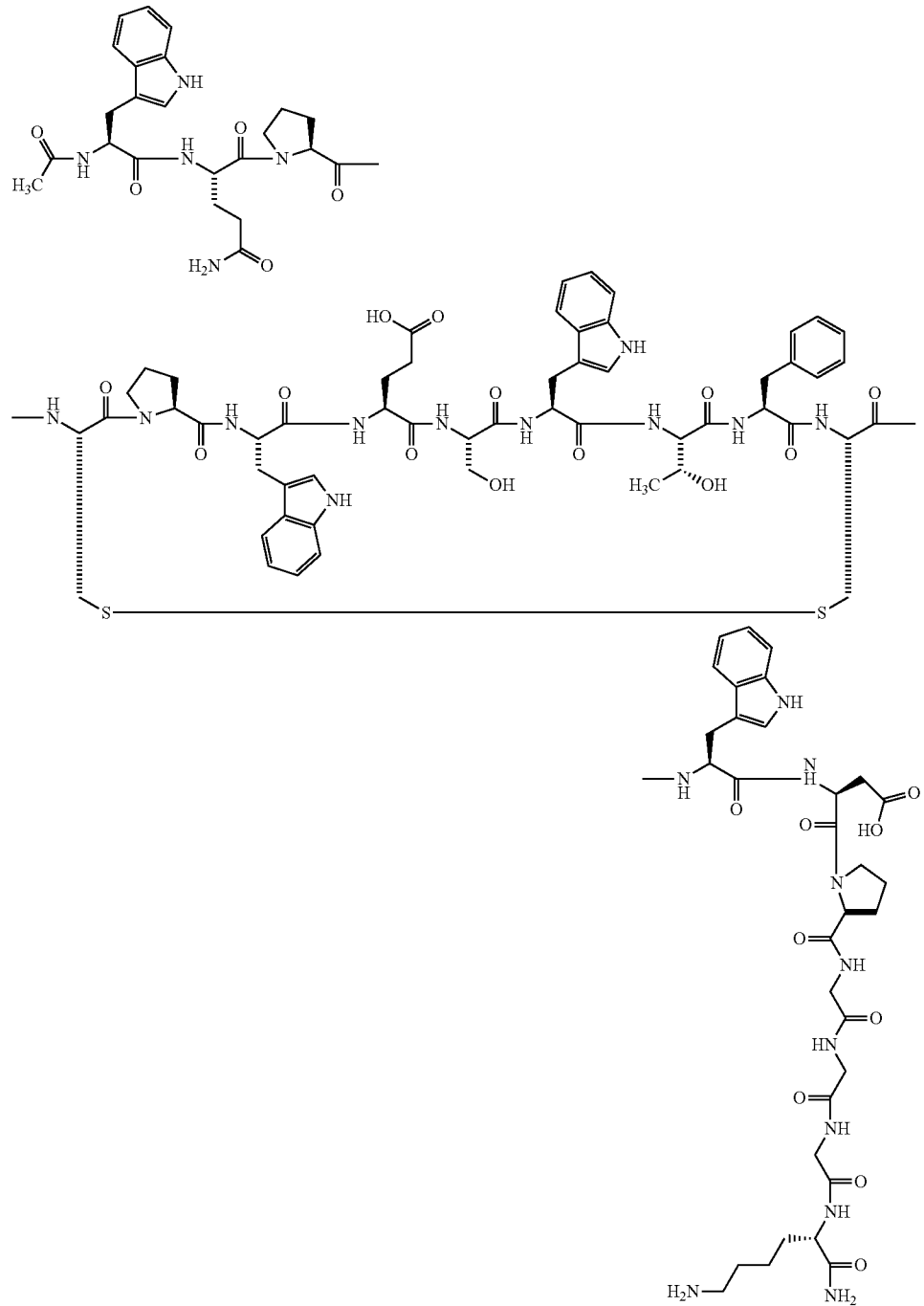

-continued
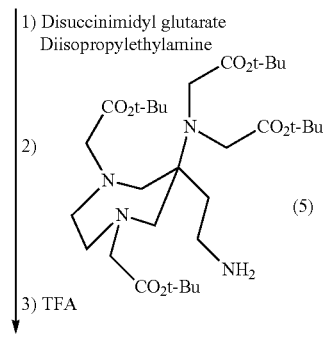
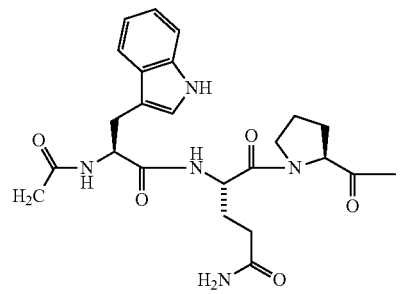
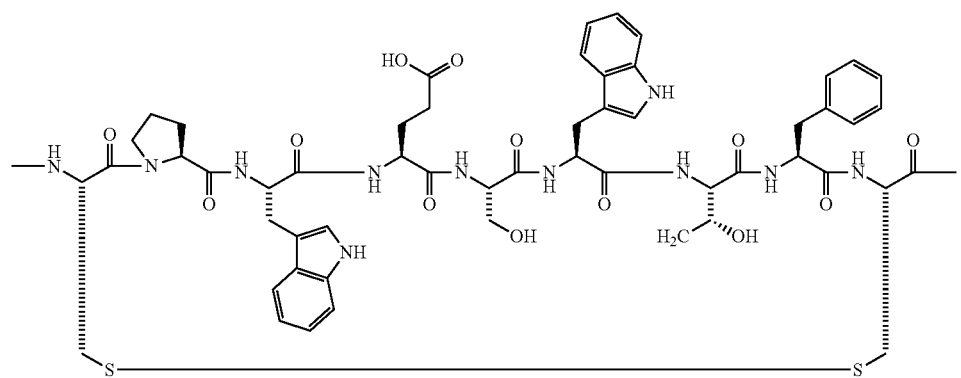

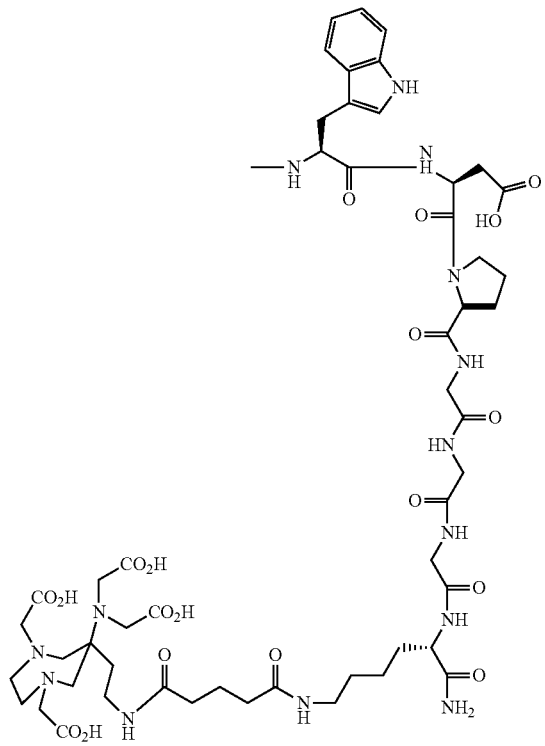

36

Compound (36). A solution of the peptide 35 (69.0 mg, 0.03 mmol) in DMF (0.5 mL) was added to a mixture of disuccinimidyl glutarate (50.0 mg. 0.153 mmol) and diisopropylethylamine (100 μL) and the mixture was stirred for 30.0 rain. DMF was removed and the residue was triturated with ethyl acetate (4×5 mL) and the ethyl acetate solution was discarded. The solid obtained was dissolved in DMF (0.4 mL) and compound 5 (30.5 mg, 0.5 mmol), diisopropylethylamine (100 □L) were added and stirred for 16 h. DMF was removed and the resulting oil was treated with reagent B (5 mL) at room temperature for 8 h. TFA was removed and the pasty solid obtained was triturated with ether to give a light yellow solid. The crude peptide 36 was purified by preparative HPLC using CH3CN/Water containing 0.1%. Fractions containing the pure product were collected and freeze dried to give 28 mg of the product.

MS: 1394.8 (M−2H/2), 929.5 (M−3H/3), 696.9 (M−4H/4).

The final compound may be labeled with, for example, Gd or $^{177}$Lu, using procedures known in the art or disclosed herein.

EXAMPLE 12

Compound of the Invention Including a Fibrin-Binding Peptide Linker

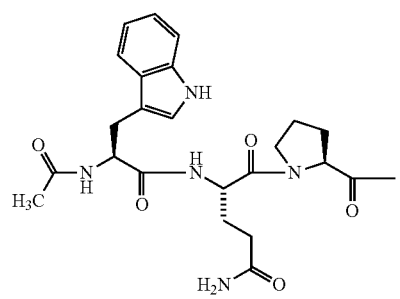

-continued
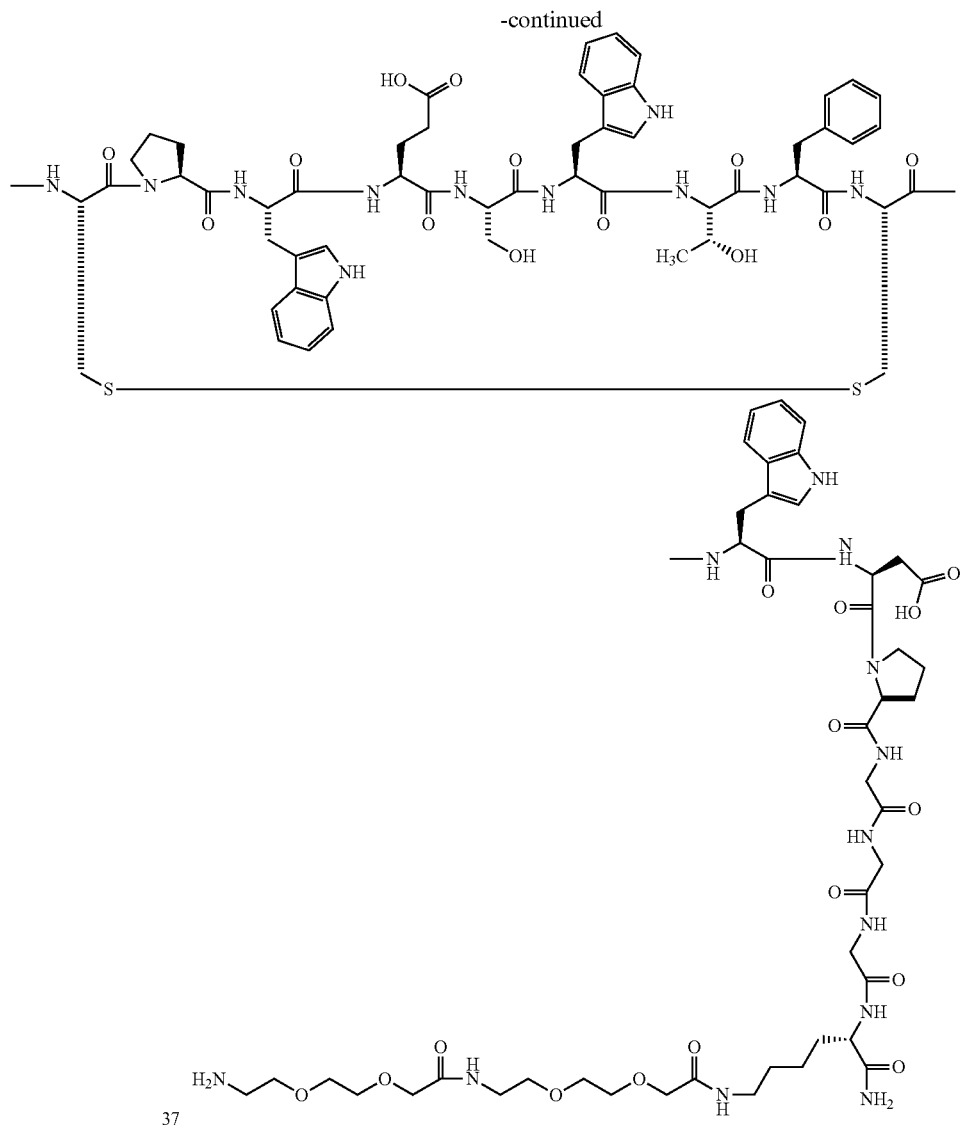
37
1) Disuccinimidyl glutarate
   Diisopropylethylamine
2) (5)
3) TFA
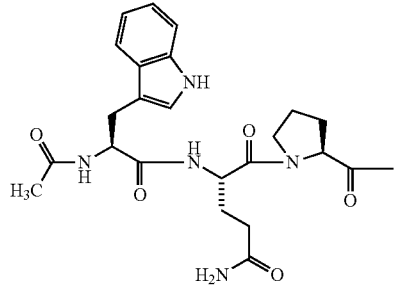

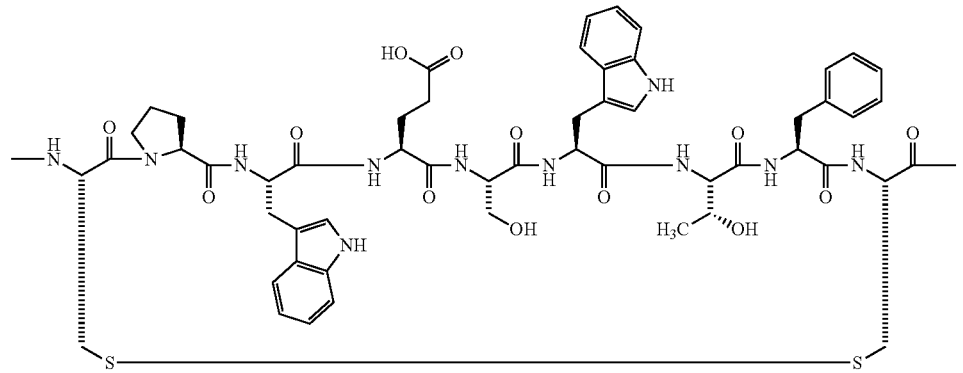

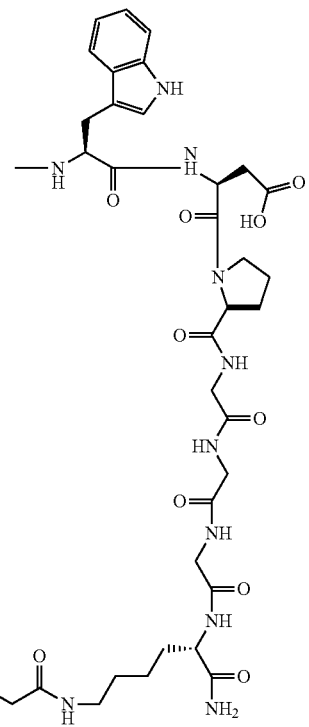

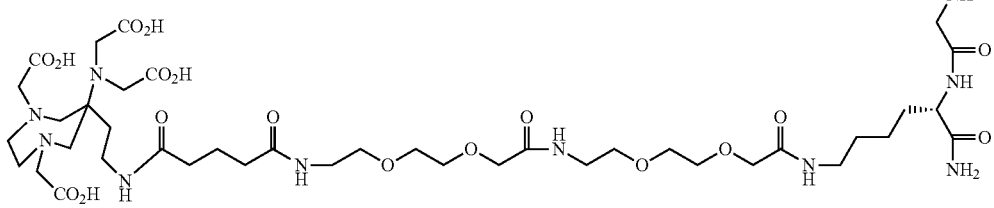

38

Compound (38). A solution of the peptide 37 (110 mg, 0.042 mmol) and diisopropylethylamine (100 µL) in DMF (0.5 mL) was added to a solution disuccinimidyl glutarate (69.0 mg. 0.21 mmol) in DMF (0.4 mL) and the mixture stirred for 1 h. DMF was removed and the residue was triturated with ethyl acetate (4×5 mL) and the ethyl acetate solution was discarded. The solid obtained was dissolved in DMF (0.6 mL), compound 5 (78.0 mg, 0.13 mmol), and diisopropylethylamine (50 µL) were added and stirred for 16 h. DMF was removed and the residue was treated with reagnet B (5 mL) and stirred at room temperature for 8 h. TFA was removed and the pasty solid obtained was triturated with ether to give a solid which was purified by preparative HPLC using CH3CN/Water containing 0.1% TFA. Fractions containing the pure product were collected and freeze dried to give 38 mg of the product.

MS: 1540.7 (M−2H/2), 875.3 (M−3H/3).

The final compound may be labeled with, for example, Gd or $^{177}$Lu, using procedures known in the art or disclosed herein.

EXAMPLE 13
Compound of the Invention Including a Fibrin-Binding Peptide
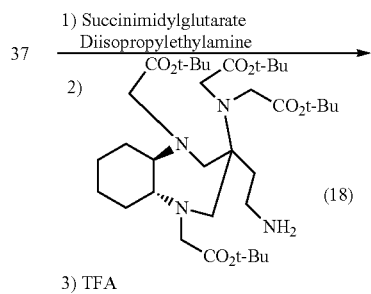
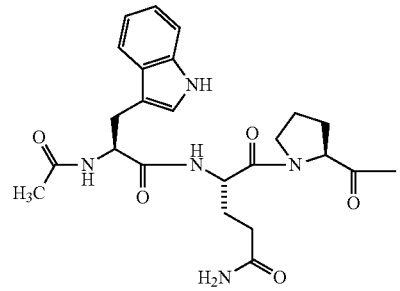
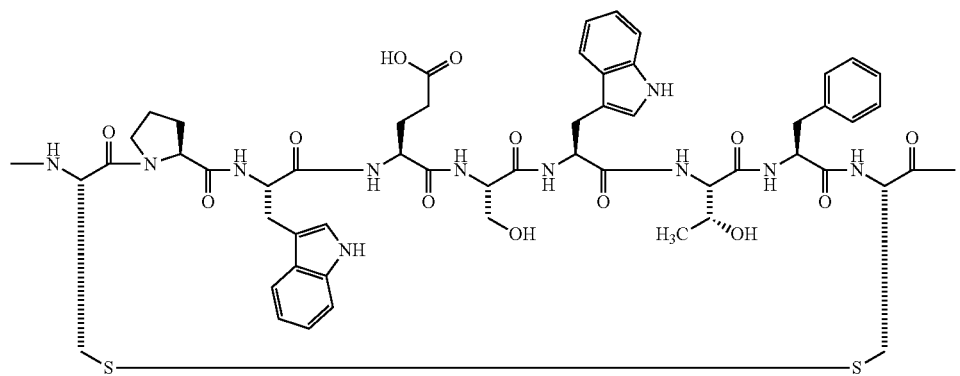

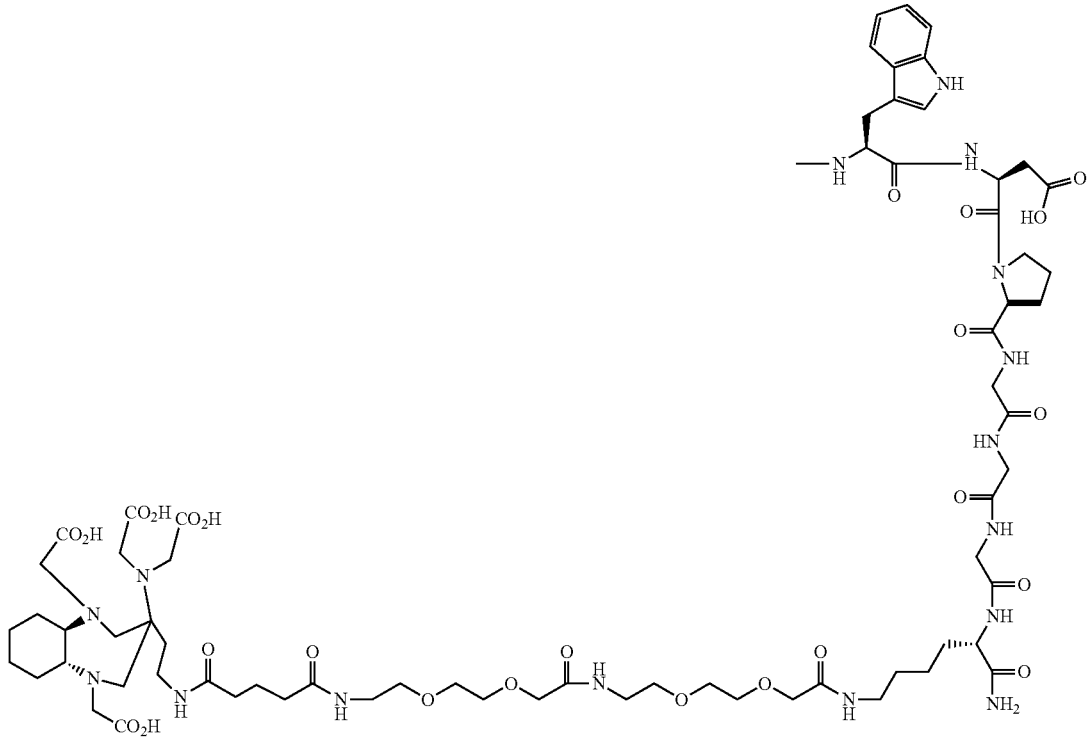

39

Compound (39). A solution of the peptide (90 mg, 0.035 mmol) and diisopropylethylamine (50 μL) in DMF (0.5 mL) was added to a solution of disuccinimidyl glutarate (50.0 mg. 0.15 mmol) in DMF (0.4 mL) and the mixture stirred for 1 h. DMF was removed and the residue was triturated with ethyl acetate (4×5 mL) and the ethyl acetate solution was discarded. The solid obtained was dissolved in DMF (0.6 mL) and compound 18 (100 mg, 0.15 mmol), diisopropylethylamine (100 μL) were added and stirred for 16 h. DMF was removed and the resulting oil was purified by preparative HPLC using CH3CN/Water containing 0.1% TFA. Pure fractions were collected and freeze dried to the tetra t-butylester as white solid. Yield 53 mg (45%). Tetra t-butylester obtained was treated with 2 mL of reagent B and stirred for 8 h. TFA was removed and the pasty solid obtained was triturated with ether to give a solid, which was purified by preparative HPLC using CH3CN/Water containing 0.1% TFA. Fractions containing the pure product were collected and freeze dried to give 35 mg of 39.

MS: 1567.1 (M−2H/2).

The final compound may be labeled with, for example, Gd or $^{177}$Lu, using procedures known in the art or disclosed herein.

EXAMPLE 14

Compound of the Invention Including GRP Targeting Peptide (which Binds the GRP-R)

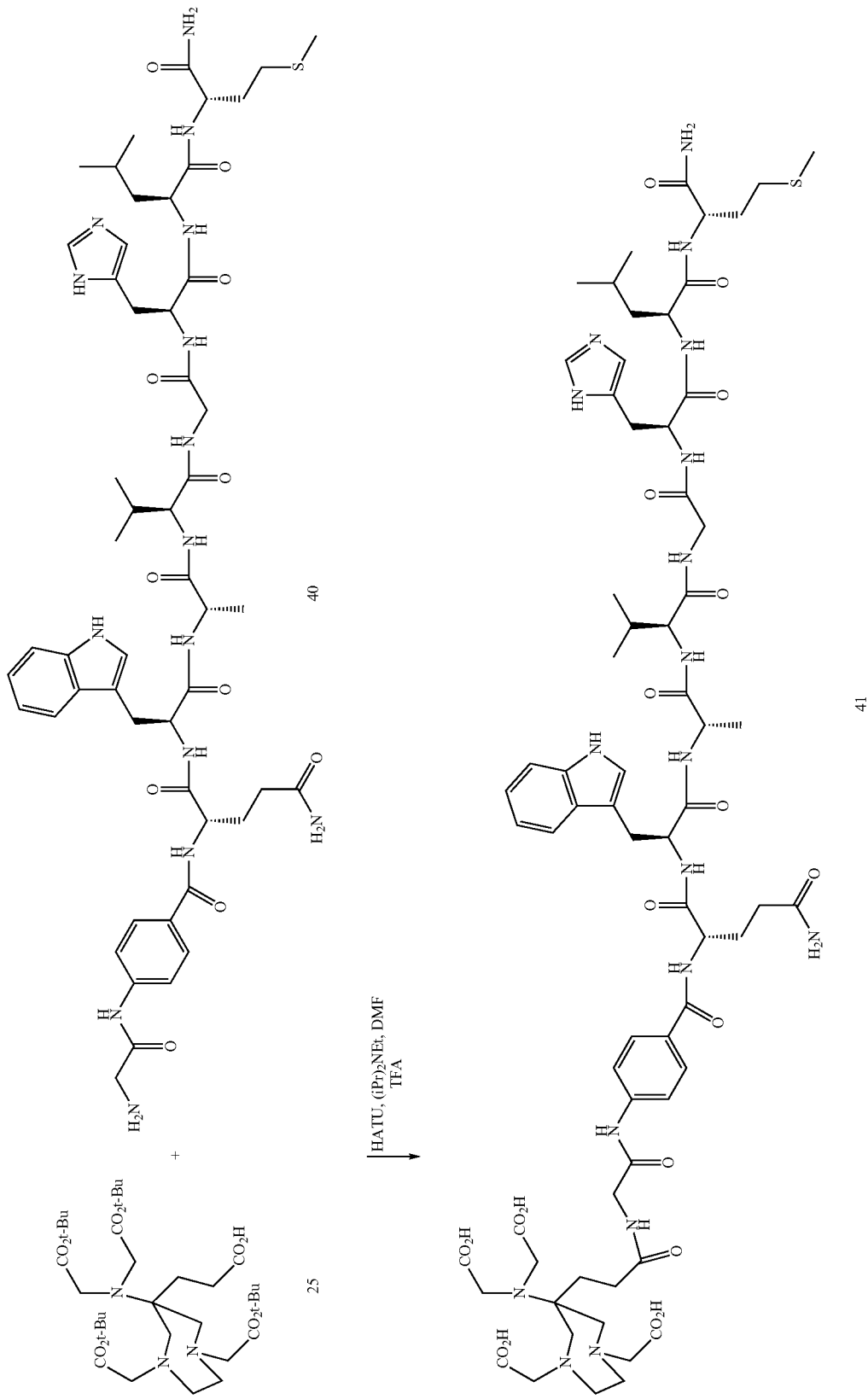

Compound (41). Diisopropylethylamine (150 μL) was added to a cooled solution of the acid 25 (0.19 g, 0.3 mmol) and HATU (0.12 g, 0.32 mmol) in DMF (1 mL) and stirred for 5 min. Purified peptide 40 (0.11 g, 0.1 mmol) was then added to the reaction mixture and stirred for 18 h. DMF was removed and the oil obtained was dissolved in a mixture of DMF/CH3CN and purified by preparative HPLC. Pure fractions containing the tetra-t-butyl ester were collected and freeze dried to give the tetra-t-butyl ester as a white solid. Yield 80 mg (32%). Tetra-t-butyl ester obtained was dissolved in reagent B and stirred for 8 h. TFA was removed and the resulting pasty solid was purified by HPLC using CH3CN/Water/0.1% TFA. Pure fractions were collected and freeze dried to give a white solid. Yield 23 mg (38%)

MS: 1515.7 (M−H), 757.4 (M−2H)/2.

The final compound may be labeled with, for example, Gd or $^{177}$Lu, using procedures known in the art or disclosed herein.

EXAMPLE 15

Compound of the Invention Including GRP Targeting Peptide

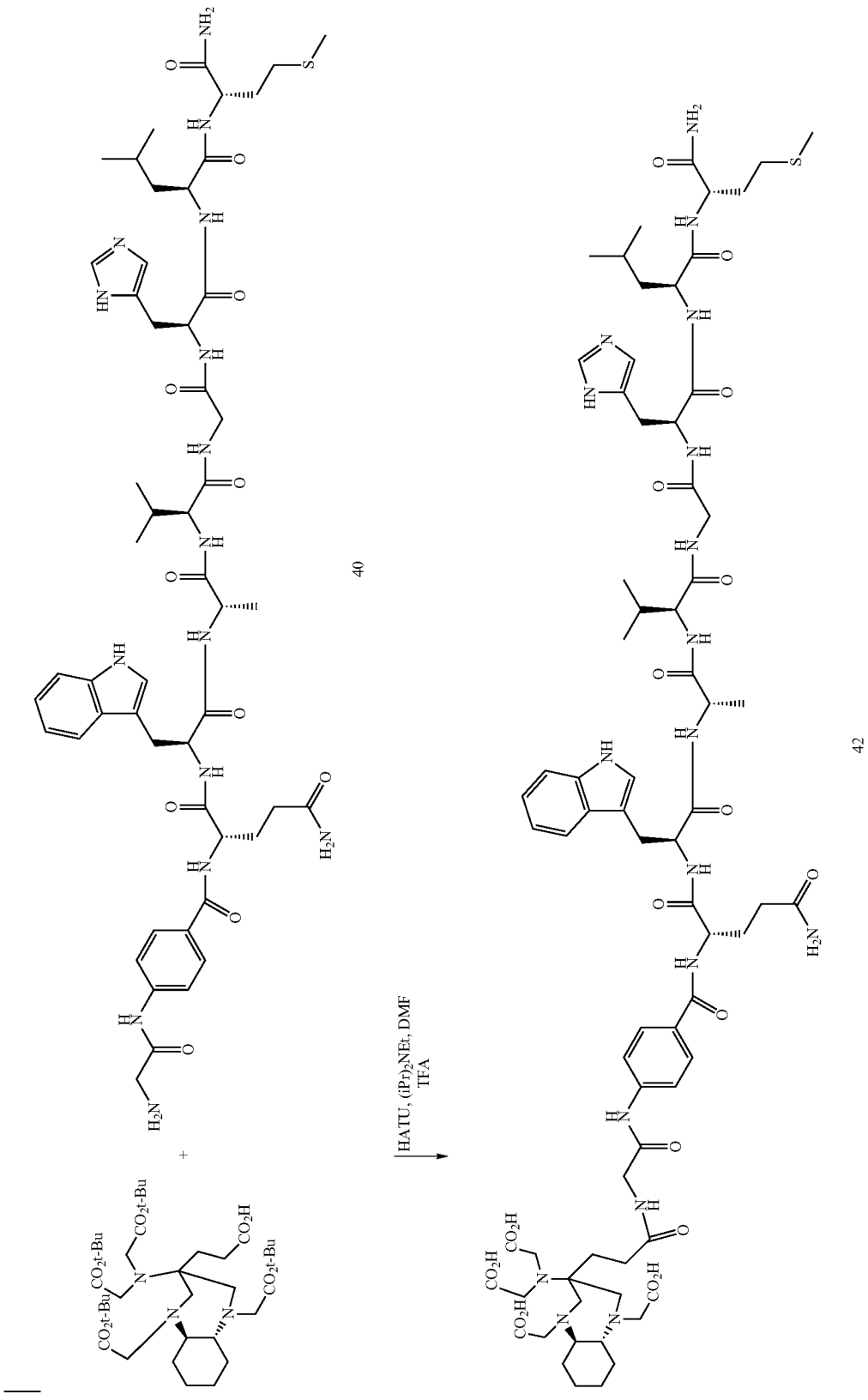

Compound (42). Diisopropylethylamine (150 µL) was added to a cooled mixture of 30 (0.278 g, 0.4 mmol) and HATU (0.152 g, 0.4 mmol) in DMF (1 mL) and stirred for 5 min. Purified peptide 40 (0.12 g, 0.11 mmol) was added to the reaction mixture and stirred for 18 h. DMF was removed and the oil obtained was dissolved in a mixture of DMF/CH3CN and purified by preparative HPLC. Pure fractions containing the tetra-t-butyl ester were collected and freeze dried to give the tetra t-butylester. Yield 62 mg (32%). Tetra t-butyl ester (36.0 mg, 0.02 mmol) was dissolved in reagent B and stirred for 8 h. TFA was removed and the resulting thick oil was purified by HPLC using CH3CN/Water/0.1% TFA. Pure fractions were collected and freeze dried to give 42 as a white solid. Yield 12 mg (38%).

MS: 1569.7 (M−H), 784.4 (M−2H/2), 803.3 (M+K−2H)/2

The final compound may be labeled with, for example, Gd or $^{177}$Lu, using procedures known in the art or disclosed herein.

EXAMPLE 16

Cyclohexyl Ring Appended to Aazta

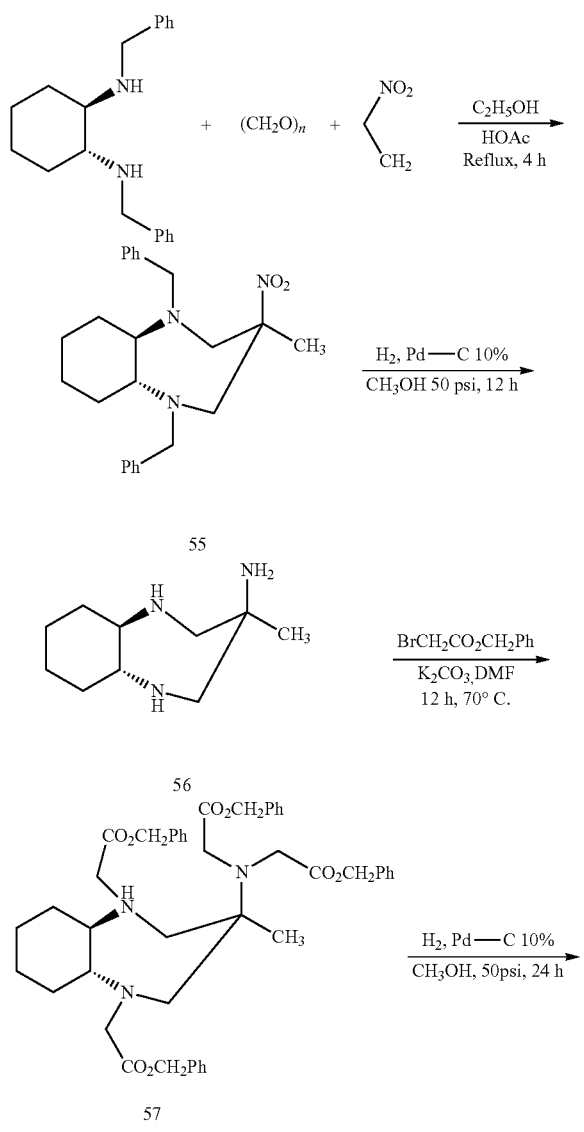

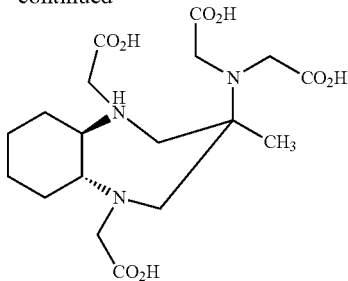

Compound (55). Acetic acid (4.1 mL, 68 mol) was added to a solution of N,N'-dibenzyl-trans-1,2-diaminocyclohexane (10.0 g, 34 mmol) in ethanol (60 mL) and the mixture was stirred at 60° C. for 10 min. Nitroethane (2.5 mL, 33 mol) was then added to the reaction mixture. Paraformaldehyde (3.4 g, 167 mol) was added to the reaction mixture in small portions over a period of 30 min. After 4 h at reflux the reaction mixture was cooled to 0° C. and a light yellow solid began to separate from the reaction mixture. The precipitated solid was filtered and washed with ice-cooled ethanol and dried under vacuum. Yield 8.2 g, 63%.

MS: 394.1 (M+H).

Compound (56). Pd—C 10%, (2.0 g) was added to a solution of the nitro compound 55 (4.0 g, 10 mmol) in methanol (40 mL) and the mixture was hydrogenated at 50 psi for 12 h. The catalyst was removed by filtration and the methanol was evaporated to give the amine as a thick light yellow oil. Yield 1.75 g (96%).

MS: 184.1 (M+H).

Compound (57). Amine 56 (1.83 g, 10 mmol) in DMF (25 mL) was added to a mixture of potassium carbonate (6.9 g, 50 mol) and benzyl-2-bromoacetate (11.45 g, 7.92 mL, 50 mmol) in DMF (30.0 mL) over a period of 4-5 h. The reaction mixture was stirred at 60° C. during the addition and at 70° C. for an additional 12 h. Solids were removed by filtration and the filter cake was washed with DMF (25 mL). The filtrate and the washings were combined and the DMF was removed under vacuum. The residue was taken up in ethyl acetate (400 mL) washed with water (2×200 mL) and dried (Na$_2$SO$_4$). Evaporation of ethyl acetate gave an oil. The crude product was then chromatographed over silica gel twice (hexane:ethyl acetate 7:3) to obtain a product 57. This was repurified over silica gel (hexane:ethyl acetate 7:3). Product containing pure fraction were collected and evaporated to give the benzyl ester as a thick oil. Yield 2.8 g (36%).

MS: 776.3 (M+H)

Compound (58). Pd—C-10% (150 mg) was added to a solution of the tetra benzyl ester 57 (0.39 g, 0.5 mmol) in methanol (25 mL) and the mixture was hydrogenated at 50 psi for 24 h. The catalyst was removed by filtration and the solvent was removed to afford the tetra acid, which was dissolved in acetonitrile and water and freeze dried to give 57 as a white solid. Yield 0.18 g (87%).

MS: 416.2 (M+H) The final compound may be labeled with, for example, Gd or $^{177}$Lu using procedures known in the art or disclosed herein. If attachment of a targeting moiety is desired, the methyl group on the CyAazta core could be substituted with an amino alkyl or carboxy alkyl group, allowing attachment of the targeting moiety.

REFERENCES FOR EXAMPLES 4-16

1) Alston, T. A.; Porter, D. J. T.; Bright, H. J. *J. Enzyme Inhibition.* 1987, 212-222.
2) Eisenwiener, K.-P.; Powell, P.; Macke, H. R. *Bioorg., Med. Chem. Lett.* 2000, 10, 2133-2135.
3) Tamai, T.; Tanaka, M.; Mukaiyama, H.; Hirabayashi, A.; Muranaka, H.; Sato. M.; Akahane, M. U.S. Pat. No. 6,353,025
4) Tye, H.; Eldred, C.; Wills, M. Tetrahedrson Lett. 44, 155-158 (2002)

EXAMPLE 17

An Aazta Derivative Functionalized with an Aromatic Group Useful as Another Method of Linkage and Also Providing a Stronger UV Chromophore

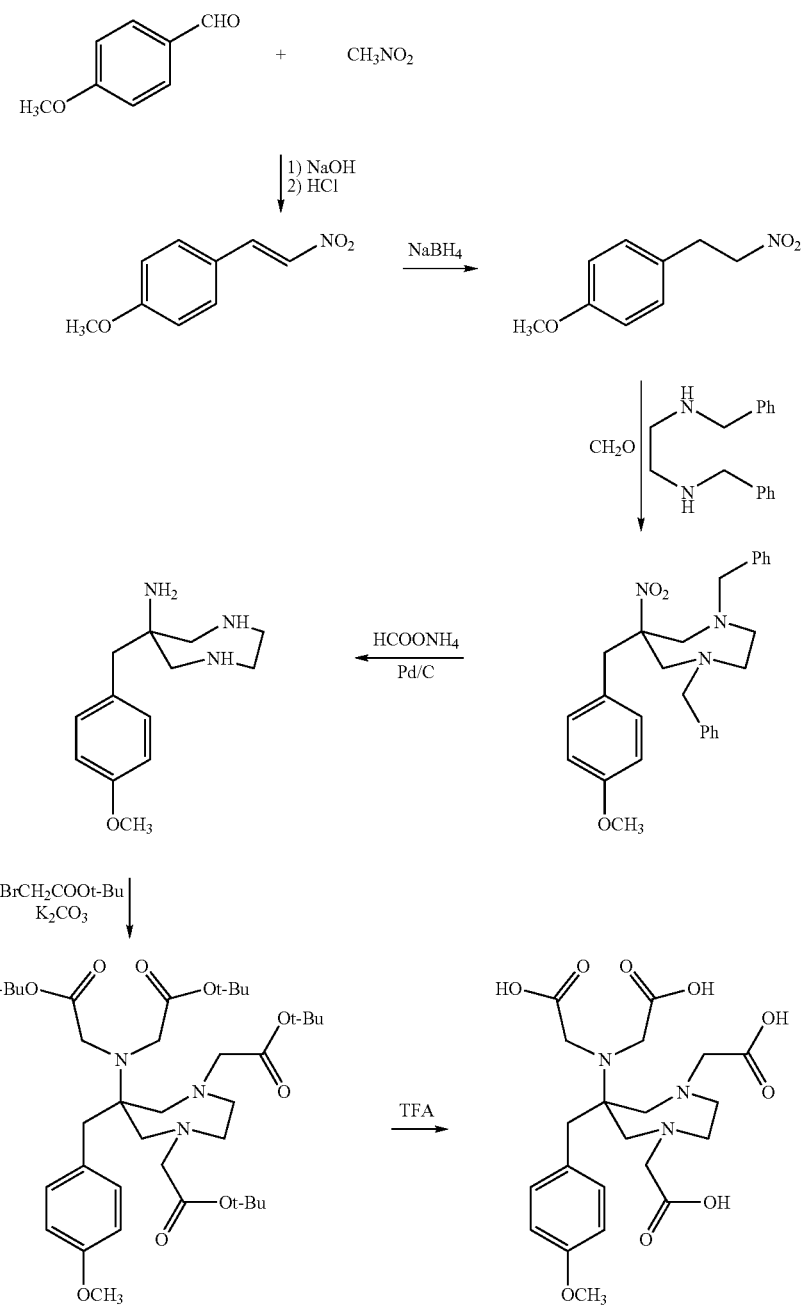

p-MethoxyBenzylAAZTA

4-Methoxy-β-nitrostyrene p-Methoxybenzaldehyde (11.19 g, 82.2 mmol) and nitromethane (5.0 g, 82.2 mmol) were dissolved in methanol (20 mL) in a two-necked flask equipped with a thermometer and a pressure-equalizing dropping funnel. NaOH (4.27 g, 0.107 mol) in ice/water (10 mL) was added dropwise to the solution keeping the temperature below 15° C. A fine slurry formed during addition and additional methanol was added to allow efficient stirring. After the addition the reaction mixture was diluted with ice/water and the resulting clear solution was added dropwise to a solution of $HCl/H_2O$ (40 mL/60 mL); a yellow precipitate formed during the addition. The precipitate was filtered on a buchner funnel and crystallized from methanol obtaining 4-methoxy-β-nitrostirene (10.66 g, 72%). Yellow needles. M.p. 57-58° C. ESI-MS: 180 ($MH^+$); (Calc. for $C_9H_9NO_3$: 179 u.m.a.).

4-Methoxy-2'-nitroethylbenzene

In a 500 mL two-necked flask equipped with a thermometer and a pressure-equalizing dropping funnel, $NaBH_4$ (4.73 g, 59.5 mmol) was suspended in 1,4-dioxane/ethanol (100/30 mL). 4-Methoxy-β-nitrostyrene (10.6 g, 0.125 mol) in 1,4-dioxane (100 mL) was added dropwise to the solution over 45 minutes keeping the temperature below 30° C. A fine slurry formed during the addition. After the addition the reaction mixture was stirred overnight then ice/water (100 mL) was added, and a 50% aq. solution of acetic acid was added to neutralize excess $NaBH_4$; the resulting clear solution was concentrated in vacuo and the residue was dissolved in $CH_2Cl_2/H_2O$. The organic phase was washed with water (2×30 mL) and brine (1×30 mL), dried ($Na_2SO_4$), filtered and concentrated in vacuo obtaining 4 (10.78 g, 94%) as yellow oil. ESI-MS: 182 ($MH^+$); (Calc. for $C_9H_{11}NO_3$: 181 u.m.a.).

1,4-Dibenzyl-6-(4-methoxybenzyl)-6-nitro-1,4-diazepane

In a 500 mL round-bottom flask N'-dibenzylethylenediamine diacetate (20.14 g, 55.9 mmol) and 4-methoxy-2'-nitroethylbenzene (10.12 g, 55.9 mmol) are dissolved in 1:1 toluene/methanol (150 mL). Paraformaldehyde (5.87 g, 0.196 mol) is added portionwise to the solution and the resulting suspension is refluxed. The mixture becomes homogeneous (dissolution of paraformaldehyde) and after 3 h at reflux, the mixture is cooled and evaporated in vacuo. The residue is recrystallized from methanol, obtaining the pure product (18.84 g, 76%) as light yellow solid. M.p. 100-102° C. (MeOH). ESI-MS: 468 ($MNa^+$), 446 ($MH^+$); (Calc. for $C_{27}H_{31}N_3O_3$: 445 u.m.a.).

6-(4-Methoxybenzyl)-1,4-diazepan-6-ylamine (6)

In a 100 mL flask, compound 5 (1.0 g, 2.24 mmol) was dissolved in methanol (10 mL); 10% Pd/C (400 mg, moistened with 0.1 mL water) was added followed by ammonium formate (2.83 g, 44.9 mmol). The mixture was stirred and heated to reflux for 3 h. When the reaction was complete (TLC PET/AcOEt 9/1), the catalyst was removed by filtration on Celite®, and the filtrate evaporated in vacuo. The residue is dissolved in dichloromethane and washed with 5% aq. NaOH. The organic phase was then dried ($Na_2SO_4$), filtered and evaporated in vacuo obtaining the pure triamine (518 mg, 98%) as light yellow oil. ESI-MS: 258 ($MNa^+$), 236 ($MH^+$); (Calc. for $C_{13}H_{21}N_3O$: 235 u.m.a.).

[6-Bis(tert-butoxycarbonylmethylamino)-4-tert-butoxycarbonylmethyl-6-(4-methoxybenzyl)-1,4-diazepan-1-yl]acetic acid tert-butyl ester In a 25 mL round-bottom flask the triamine (500 mg, 2.12 mmol) was dissolved in acetonitrile (10 mL) and $K_2CO_3$ (2.3 g, 17.0 mmol) was added. t-Butyl bromoacetate (2.07 g, 10.6 mmol) was slowly dropped into the stirred heterogeneous mixture, while maintaining the temperature <10° C. (ice bath). After the addition the mixture was heated at 60° C. with stirring until TLC showed complete conversion. The precipitate was filtered and washed with dichloromethane; the filtrate and the washings were combined and evaporated in vacuo to give the crude product. The semisolid residue was purified by silica gel chromatography (petroleum ether/ethyl acetate 9.3/0.7), obtaining the pure product as pale yellow oil (500 mg, 34%). ESI-MS: 714 ($MNa^+$), 692 ($MH^+$); (Calc. for $C_{37}H_{61}N_3O_9$: 691 u.m.a.).

[6-Bis(carboxymethylamino)-4-carboxymethyl-6-(4-methoxybenzyl)-1,4-diazepan-1-yl]acetic acid In a 25 mL round-bottom flask the tetraester (250 mg, 0.361 mmol) was dissolved in trifluoroacetic acid (4 mL) and stirred at room temperature overnight. The solution was then evaporated in vacuo and the residue was dissolved in methanol (1 mL). The product was then precipitated with excess diethyl ether, isolated by centrifugation, washes thoroughly with diethyl ether and dried in vacuo, obtaining the pure ligand (169 mg, 95%) as amorphous white solid. M.p. 186-189° C. (dec.). ESI-MS: 490 ($MNa^+$), 468 ($MH^+$); (Calc. for $C_{21}H_{29}N_3O_9$: 467 u.m.a.).

The final compound may be labeled with, for example, Gd or $^{177}Lu$, using procedures known in the art or disclosed herein.

EXAMPLE 18

An Aazta Derivative Functionalized with an Aromatic Group Useful as Another Method of Linkage and Also Providing a Stronger UV Chromophore

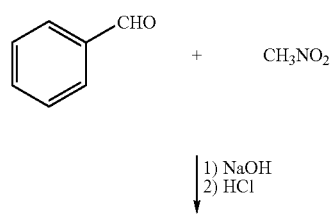

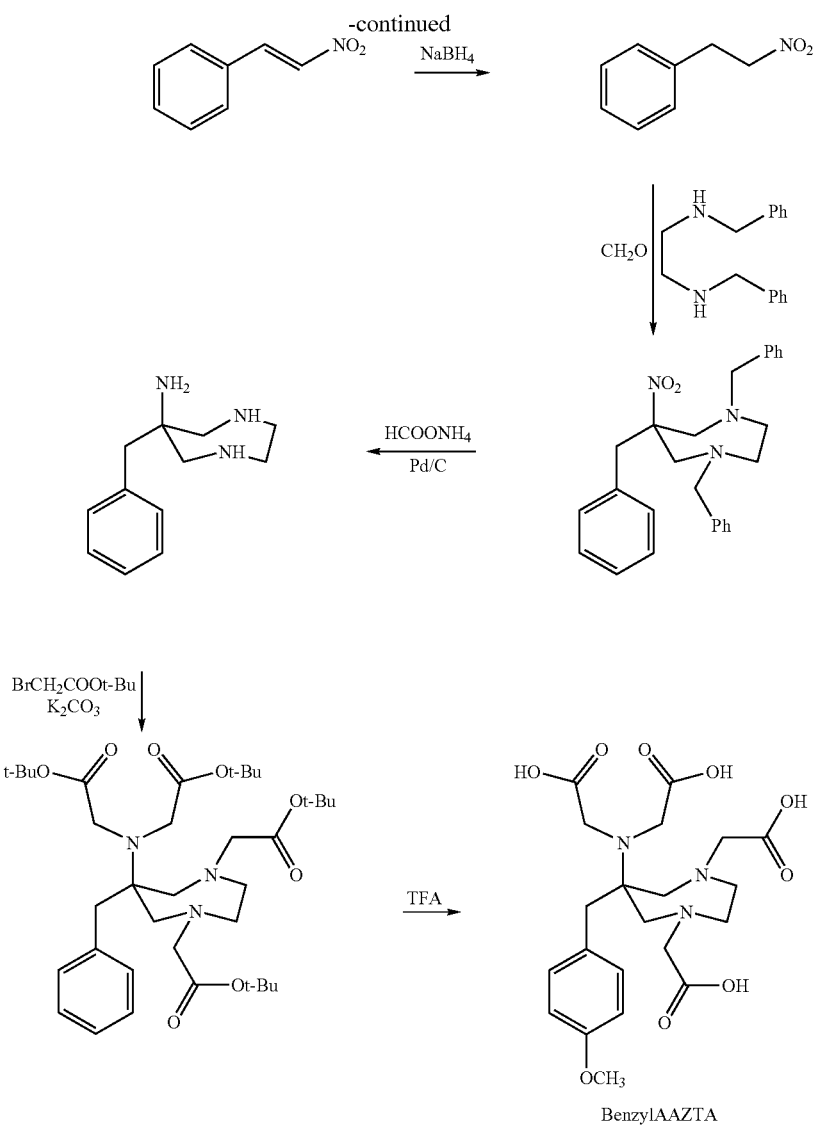

BenzylAAZTA

β-Nitrostyrene (3)

Benzaldehyde (2, 52.35 g, 0.493 mol) and nitromethane (30.11 g, 0.493 mol) were dissolved in methanol (100 mL) in a two-necked flask equipped with a thermometer and a pressure-equalizing dropping funnel. NaOH (25.6 g, 0.641 mol) in ice/water (50 mL) was added dropwise to the solution keeping the temperature below 15° C. A fine slurry formed during the addition and methanol was added to allow stirring. After the addition the slurry was diluted with ice/water and the resulting clear solution was added dropwise to a solution of conc. HCl/H$_2$O (200/300 ml); a yellow precipitate was formed during the addition. The precipitate was filtered on a buchner funnel, washed with water and crystallized from methanol obtaining pure 3 (58.78 g, 80%). Yellow needles. M.p. 57-58° C.

2-Nitroethylbenzene (4)

In a 500 mL two-necked flask equipped with a thermometer and a pressure-equalizing dropping funnel, NaBH4 (5.33 g, 0.140 mol) was suspended in 1,4-dioxane/ethanol (100 mL/30 ml). β-Nitrostyrene (3, 10.0 g, 67.0 mmol) in 1,4-dioxane (100 mL) was added dropwise to the solution over 45 minutes, keeping the temperature below 30° C. A fine slurry formed during the addition. After the addition the reaction mixture was stirred overnight, then ice/water (125 mL) was added, and a 50% solution of acetic acid was added to neutralize excess NaBH4; the clear solution was then concentrated in vacuo and the residue was dissolved in water and extracted twice with CH2Cl12. The organic phase was washed with water (2×30 mL) and brine (1×30 mL), dried (Na$_2$SO$_4$), filtered and evaporated in vacuo obtaining 4 (8.4.0 g, 83%) as yellow oil. ESI-MS: 152 (MH$^+$) (Calc. for C$_8$H$_9$NO$_2$: 151).

1,4-Dibenzyl-6-benzyl-6-nitro-1,4-diazepane (5)

In a 250 mL round-bottom flask N,N'-dibenzylethylenediamine diacetate (19.67 g, 54.6 mmol) and 2-nitroethylbenzene (4, 8.28 g, 54.6 mmol) are dissolved in 1:1 toluene/methanol (100 mL). Paraformaldehyde (5.74 g, 0.191 mol) is added portionwise to the solution and the resulting suspension is refluxed. The mixture becomes homogeneous (dissolution of paraformaldehyde) and after 3 h at reflux, the mixture is cooled and evaporated in vacuo. The residue is recrystallized from methanol, obtaining pure 5 (20.29 g, 89%) as light yellow solid. M.p. 83-85° C. (EtOH), ESI-MS: 438 (MNa$^+$), 416 (MH$^+$); (Calc. for $C_{26}H_{29}N_3O_2$: 415 u.m.a.).

6-Benzyl-1,4-diazepan-6-ylamine (6)

In a 500 ml flask, compound 5 (16.0 g, 38.5 mmol) was dissolved in methanol (100 mL); Pd/C (10%, 3.0 g, moistened with 0.5 ml water) was added at once followed by ammonium formate (24.0 g, 0.385 mol). The mixture was stirred and heated to reflux for 3 h. When the reaction is complete (TLC PET/AcOEt 9/1), the catalyst was removed by filtration on Celite®, and the filtrate evaporated in vacuo. The residue is redissolved in dichloromethane and washed with 5% aq. NaOH. The organic phase was then dried ($Na_2SO_4$) obtaining 6 (5.98 g, 76%) as light yellow oil. M.p.: ESI-MS: 206 (MH$^+$); (Calc. for $C_{12}H_{19}N_3$: 205 u.m.a.).

[6-Bis(tert-butoxycarbonylmethylamino)-4-tert-butoxycarbonylmethyl-6-benzyl-1,4-diazepan-1-yl]acetic acid tert-butyl ester (7)

In a 100 ml round-bottom flask the amine 6 (1.80 g, 8.77 mmol) was dissolved in acetonitrile (25 mL) and $K_2CO_3$ (9.69 g, 70.1 mmol) was added. t-Butyl bromoacetate (8.55 g, 43.8 mmol) was slowly dropped into the stirred heterogeneous mixture, while maintaining the temperature <10° C. (ice bath). After the addition the mixture was heated at 60° C. with stirring until TLC showed complete conversion. The precipitate was filtered and washed with dichloromethane; the filtrate and the washings were combined and evaporated in vacuo to give the crude product. The semisolid residue was purified by silica gel chromatography (petroleum ether/ethyl acetate 9.3/0.7), obtaining pure 7 as pale yellow oil (1.91 g, 33%). ESI-MS: 662 (MH$^+$); (Calc. for $C_{36}H_{59}N3O8$: 661 u.m.a.).

[6-Bis(carboxymethylamino)-4-carboxymethyl-6-benzyl-1,4-diazepan-1-yl]acetic acid (1)

In a 50 ml round-bottom flask the ester 7 (1.85 g, 2.8 mmol) was dissolved in trifluoroacetic acid (10 mL) and stirred at room temperature overnight. The solution was then evaporated in vacuo and the residue was dissolved in methanol (2 mL). The product was precipitated with excess diethyl ether, isolated by centrifugation, washed thoroughly with diethyl ether and dried in vacuo, obtaining pure 1 (1.045 g, 86%) as amorphous white solid. M.p. 105-107° C. ESI-MS: 460 (MNa$^+$), 438 (MH$^+$); (Calc. for $C_{20}H_{27}N_3O_8$: 437 u.m.a.).

The final compound may be labeled with, for example, Gd or $^{177}$Lu, using procedures known in the art or disclosed herein.

EXAMPLE 19

Compound of the Invention in which R2 is a Carboxy Substituted Alkyl, which can be Used for Derivatization with, E.G., a Targeting Moiety

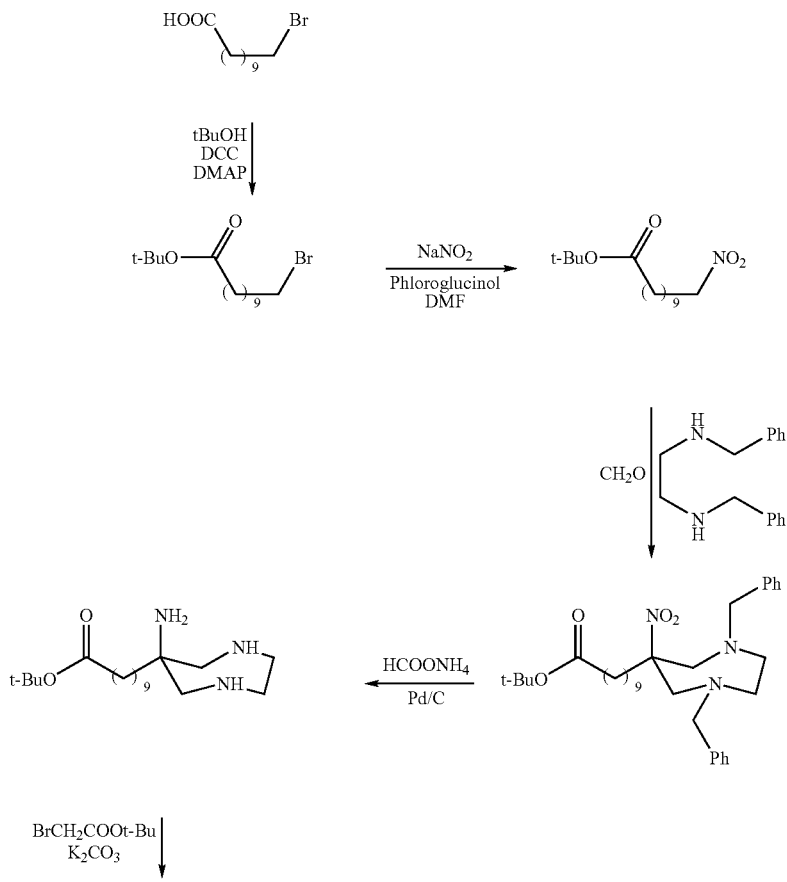

-continued

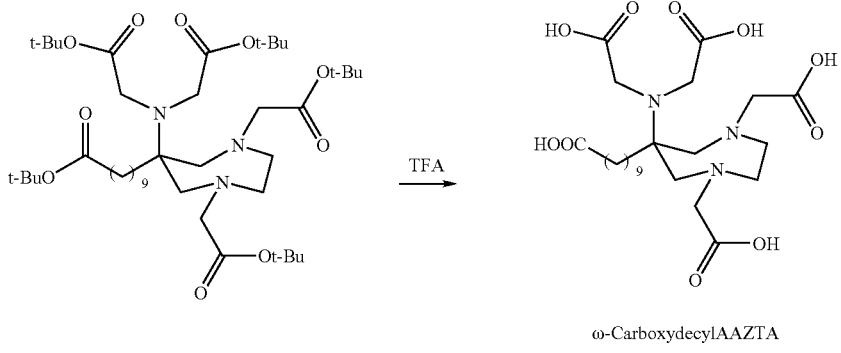

ω-CarboxydecylAAZTA

11-Bromoundecanoic acid tert-butyl ester

DCC (8.90 g, 43.4 mmol) was added to a solution of 11-bromoundecanoic acid (10.0 g, 37.7 mmol), 2-methyl-2-propanol (8.38 g, 0.113 mol) and DMAP (0.50 g, 3.77 mmol) in CH2Cl2 (60 mL). The reaction mixture was stirred for 2 days at room temperature, and the precipitated dicyclohexylurea was filtered off and washed with CH2Cl2. The filtrate and the combined washings were combined, washed with water (2×50 mL), HCl 1M (2×50 mL), NaHCO3 5% (2×50 mL) and brine (2×50 ml). The organic phase was dried (Na2SO4) and concentrated in vacuo. The crude product was purified by silica-gel column chromatography (PET/Ether 98/2) obtaining a colourless oil 3 (6.37 g, 60%). ESI-MS: 323-321 (MH$^+$); (Calc. for $C_{15}H_{29}BrO_2$: 320 u.m.a.).

11-Nitroundecanoic acid tert-butyl ester

In a 100 ml two-neck round bottom flask 11-bromoundecanoic acid t-butyl ester (6.10 g, 19.0 mmol) was dropped into a stirred solution of NaNO2 (2.60 g, 38.0 mmol) and phloroglucinol (3.10 g, 19.0 mmol) in DMF (10 ml). The reaction mixture was warmed at 50° C. and stirred for 24 h, then poured into a mixture of 40 mL of ice/water and 40 mL of PET. After separation, the aqueous phase was further extracted with PET (3×30 mL), dried (Na2SO4) and concentrated in vacuo. The crude product was purified by silica-gel column chromatography (PET/diethyl ether 95/5) obtaining a light yellow solid (2.29 g, 42%). M.p. 39-42° C. ESI-MS: 288 (MH$^+$); (Calc. for $C_{15}H_{29}NO_4$: 287 u.m.a.).

1,4-Dibenzyl-6-(10-tert-butoxycarbonyldecyl)-6-nitro-1,4-diazepane

In a 250 mL round-bottom flask N,N'-dibenzylethylenediamine diacetate (2.76 g, 7.65 mmol) and 11-nitroundecanoic acid tert-butyl ester (2.20 g, 7.65 mmol) were dissolved in 1:1 toluene/ethanol (100 mL). Paraformaldehyde (800 mg, 26.8 mmol) was added portionwise to the solution and the resulting suspension was refluxed. The mixture became homogeneous (dissolution of paraformaldehyde) and after 3 h at reflux, the mixture was cooled and evaporated in vacuo. The residue was purified by column chromatography (PET/diethyl ether 95/5) obtaining a colourless oil (2.90 g, 69%). ESI-MS: 552 (MH$^+$); (Calc. for $C_{33}H_{49}N_3O_4$: 551 u.m.a.).

6-(10-tert-butoxycarbonyldecyl)-1,4-diazepan-6-ylamine

In a 50 ml flask, 1,4-dibenzyl-6-(10-tert-butoxycarbonyldecyl)-6-nitro-1,4-diazepane (500 mg, 0.906 mmol) was dissolved in methanol (20 mL). Pd/C 10% (200 mg, moistened with 0.2 mL water) was added followed by ammonium formate (1.14 g, 18.1 mmol). The mixture was stirred and heated to reflux until complete disappearance of starting materials. The catalyst was then removed by filtration, and the filtrate evaporated in vacuo. The residue is redissolved in dichloromethane and washed with water (2×10 mL). The organic phase was dried (Na2SO4), filtered and evaporated in vacuo to obtain the desired triaminoester (308 mg, 99.5%) as colourless oil. ESI-MS: 364 (MNa$^+$), 342 (MH$^+$); (Calc. for $C_{19}H_{39}N_3O_2$: 341 u.m.a.).

[6-Bis(tert-butoxycarbonylmethylamino)-4-tert-butoxycarbonylmethyl-6-(10-tert-butyl decanoate)-1,4-diazepan-1-yl]acetic acid tert-butyl ester In a 100 mL round-bottom flask the triaminoester (1.16 g, 3.4 mmol) was dissolved in acetonitrile (20 mL) and K2CO3 (3.76 g, 27.2 mmol) was added. t-Butyl bromoacetate (3.31 g, 17.0 mmol) was slowly dropped into the stirred heterogeneous mixture, while maintaining the temperature <10° C. (ice bath). After the addition the mixture was heated at 60° C. with stirring until TLC showed complete conversion. The precipitate was filtered off and washed with dichloromethane; the filtrate and the washings were combined and evaporated in vacuo to give the crude product. The semisolid residue was purified by silica gel chromatography (petroleum ether/ether 8.5/1.5), obtaining the pure pentaester as pale yellow oil (2.71 g, 37%). ESI-MS: 820 (MNa$^+$), 798 (MH$^+$), 742 (MH$^+$-tBu); (Calc. for $C_{43}H_{79}N_3O_{10}$: 797 u.m.a.).

[6-Bis(carboxymethylamino)-4-carboxymethyl-6-(10-carboxydecyl)-1,4-diazepan-1-yl]acetic acid In a 50 mL round-bottom flask the pentaester (1.00 g, 1.25 mmol) was dissolved in trifluoroacetic acid (15 mL) and stirred at room temperature overnight. The solution was then evaporated in vacuo and the residue was dissolved in methanol (2 mL). The product was precipitated with excess diethyl ether, isolated by centrifugation, washed thoroughly with diethyl ether and dried in vacuo, obtaining pure 1 (641 mg, 99%) as amorphous white solid. M.p. 187-190° C. (dec). ESI-MS: 540 (MNa$^+$), 518 (MH$^+$); (Calc. for $C_{23}H_{39}N_3O_{10}$: 517 u.m.a.).

The final compound or a derivatized version including, e.g., a targeting moiety, may be de-protected and labeled with, for example, Gd or $^{177}$Lu, using procedures known in the art or disclosed herein.

EXAMPLE 20

Compound of the Invention in which $R_2$ is a $C_{17}$ Alkyl

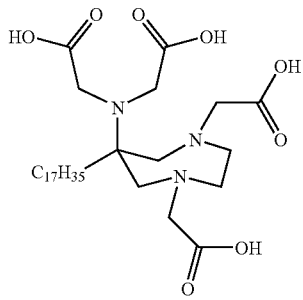

64

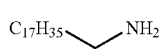

59 → 60

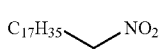

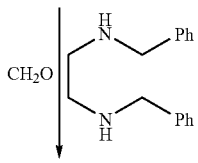

62

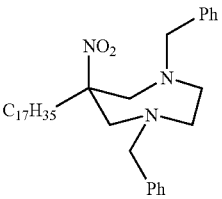

61

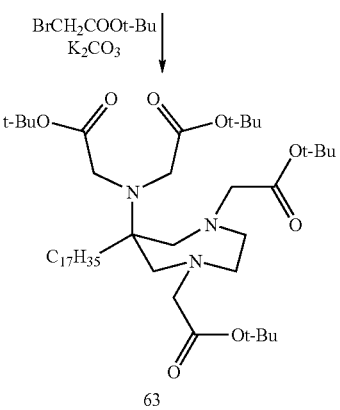

63 → 64

1-Nitrooctadecane m-Chloroperoxybenzoic acid (12.84 g, 74.4 mol, 85% pure) was dissolved in 1,2-dichloroethane (200 ml) in a two-necked flask equipped with a condenser and a pressure-equalizing dropping funnel. Octadecylamine (2, 5.0 g, 18.6 mmol) in 1,2-dichloroethane (100 mL) was added dropwise to the refluxing solution. Reflux was continued for 30 minutes after the addition; then, the reaction mixture was cooled, filtered, washed with 10% aqueous $Na_2CO_3$ (3×100 ml), and dried ($Na_2SO_4$). Removal of the solvent under reduced pressure gave 1-nitrooctadecane 3 (3.9 g 71%). Colorless solid. M.p.

47-50° C. ESI-MS: 300 (MH$^+$); (Calc. for $C_{18}H_{37}NO_2$: 299 u.m.a.).

1,4-Dibenzyl-6-heptadecyl-6-nitro-1,4-diazepane

In a 500 mL round-bottom flask N,N'-dibenzylethylenediamine diacetate (4.78 g, 13 mmol) and 1-nitrooctadecane (3, 3.97 g, 13 mmol) are dissolved in 1:1 toluene/methanol (100 mL). Paraformaldehyde (1.39 g, 46.5 mmol) is added portionwise to the solution and the resulting suspension is refluxed. The mixture becomes homogeneous (dissolution of paraformaldehyde) and after 3 h at reflux, the mixture is cooled and evaporated in vacuo. The residue is recrystallized from ethanol, obtaining pure 4 (4.38 g, 61%) as colourless solid. M.p. 70-72° C. (EtOH), ESI-MS: 586 (MNa$^+$), 564 (MH$^+$); (Calc. for $C_{36}H_{57}N_3O_2$: 563 u.m.a.).

6-Heptadecyl-1,4-diazepan-6-ylamine

In a 250 ml flask, compound 4 (4.3 g, 7.6 mmol) was dissolved in methanol (100 ml). 10% Pd/C (1.0 g, moistened with 0.5 ml water) was added followed by ammonium formate (4.8 g, 76 mmol). The mixture was stirred and heated to reflux for 3 h. The catalyst was then removed by filtration, and the filtrate evaporated in vacuo. The residue is redissolved in dichloromethane and washed with 5% aq. NaOH. The organic phase was then dried (Na$_2$SO$_4$) obtaining 5 (2.6 g, 91%) as colorless wax. M.p. 66-69° C. ESI-MS: 376 (MNa$^+$), 354 (MH$^+$); (Calc. for $C_{22}H_{47}N_3$: 353 u.m.a.).

[6-Bis(tert-butoxycarbonylmethylamino)-4-tert-butoxycarbonylmethyl-6-heptadecyl-1,4-diazepan-1-yl] acetic acid tert-butyl ester In a 50 ml round-bottom flask the amine 5 (1.65 g 4.7 mmol) was dissolved in acetonitrile (15 ml) and K2CO3 (5.16 g, 37 mmol) was added. t-Butyl bromoacetate (4.55 g, 23.4 mmol) was slowly dropped into the stirred heterogeneous mixture, while maintaining the temperature <10° C. (ice bath). After the addition the mixture was heated at 60° C. with stirring until TLC showed complete conversion. The precipitate was filtered and washed with dichloromethane; the filtrate and the washings were combined and evaporated in vacuo to give the crude product. The semisolid residue was purified by silica gel chromatography (petroleum ether/ethyl acetate 9.3/0.7), obtaining pure 6 as pale yellow oil (1.35 g, 36%). ESI-MS: 832 (MNa$^+$), 810 (MH$^+$); (Calc. for $C_{46}H_{87}N_3O_8$: 809 u.m.a.).

[6-Bis(carboxymethylamino)-4-carboxymethyl-6-heptadecyl-1,4-diazepan-1-yl]acetic acid (1)

In a 50 ml round-bottom flask the ester 6 (1.354 g 1.7 mmol) was dissolved in trifluoroacetic acid (20 ml) and stirred at room temperature overnight. The solution was then evaporated in vacuo and the residue was redissolved in methanol (2 ml). The product was precipitated with excess diethyl ether, isolated by centrifugation, washed thoroughly with diethyl ether and dried in vacuo, obtaining pure 1 (795 mg, 81%) as amorphous white solid. M.p. 185-187° C. (dec.). ESI-MS: 608 (MNa$^+$), 586 (MH$^+$); (Calc. for $C_{30}H_{55}N_3O_8$: 585 u.m.a.).

The final compound may be labeled with, for example, Gd or $^{177}$Lu, using procedures known in the art or disclosed herein.

Labelling Data

Radiolabeling and HPLC Analysis of 177Lu-Complexes of Compound 36 (Example 11), Compound 41 (Example 14), Compound 42 (Example 15) and Compound 58 (Example 16)

Radiolabeling Procedure:

Typically, a 1 mg/mL solution of ligand was prepared in 0.2 M sodium acetate buffer (pH 4.8). An aliquot of this solution (2 to 5 □l) and 6 to 10 mCi of $^{177}$LuCl$_3$ (in 0.05 N HCl, specific activity 2.8-4.09 Ci/μmol) were added to 100 to 200 μL of 0.2 M, pH 4.8 NaOAc buffer to achieve a ligand to Lu molar ratio of 2:1. After incubation at room temperature for 5 min, 10 μL of 10 mM Na$_2$EDTA.2H$_2$O was added to terminate the reaction and scavenge any remaining free $^{177}$Lu in the solution. A 9:1 (v/v) mixture of Bacteriostatic 0.9% Sodium Chloride Injection USP/ASCOR L500® Ascorbic Acid Injection USP (0.2 mL) was then added to inhibit radiolysis of the resulting radiocomplex. The radiochemical purity (RCP) was determined by HPLC. Complete coordination of Lu-177 was observed within 5 min of incubation at room temperature for all the tested ligands.

Radiolabeled Complex Prepared for In Vivo Biodistribution Studies:

For biodistribution studies, the radiolabeled compounds were prepared as described above except that a 1:1 molar ratio of ligand to Lutetium was used to guarantee complete chelation of all starting ligand. The HPLC peak containing the resulting $^{177}$Lu complex was collected in 1 mL of 9:1 Bacteriostatic saline/ASCOR L500® solution containing 0.1% HSA, and the organic solvents were removed using a speed-vacuum device. The remaining solution was further diluted to the required radioconcentration using Bacteriostatic saline/ASCOR L500® Ascorbic Acid Injection USP mixed in a 9 to 1 [v/v]) ratio. The radiochemical purity of all samples was ≧95%.

HPLC analysis: All HPLC studies were performed at a flow rate of 1.5 mL/min using a column temperature of 37° C.

1. $^{177}$Lu-Compound 36 (Example 11)

HPLC column: Rigel C8 Astrosil, 5 μm, 150 mm×4.6 mm (Stellar Phase, Inc., Langhorne, Pa.).

Mobile phase: The following gradient was used, where A=water; B=water containing 30 mM (NH$_4$)$_2$SO$_4$; C=acetonitrile.

|        | A (%) | B (%) | C (%) |
|--------|-------|-------|-------|
| 0 min  | 16    | 60    | 24    |
| 20 min | 12    | 60    | 28    |
| 25 min | 12    | 60    | 28    |
| 30 min | 16    | 60    | 24    |
| 40 min | 16    | 60    | 24    |

Retention time: $^{177}$Lu-Compound 36 (Example 11)=13.6 min.

2. $^{177}$Lu-Compound 41 (Example 14)

HPLC column: Zorbax Bonus-RP, 5 μm, 80 Å pore size, 250 mm×4.6 mm (Agilent).

Mobile phase: The following gradient was used, where A=water; B=water containing 30 mM (NH4)2SO4; C=methanol; D=acetonitrile

|         | A (%) | B (%) | C (%) | D (%) |
|---------|-------|-------|-------|-------|
| 0–2 min | 70    | 30    | 0     | 0     |
| 15 min  | 36    | 30    | 16    | 16    |
| 30 min  | 30    | 30    | 20    | 20    |
| 35–40 min | 0   | 30    | 35    | 35    |
| 45 min  | 70    | 30    | 0     | 0     |
| 55 min  | 70    | 30    | 0     | 0     |

Retention time: $^{177}$Lu-Compound 41 (Example 14)=25.5 min.

3. $^{177}$Lu-Compound 42 (Example 15)

HPLC column: Zorbax Bonus-RP, 5 µm, 80 Å pore, 250 mm×4.6 mm (Agilent).

Mobile phase: The following gradient was used, where A=water; B=water containing 30 mM $(NH_4)_2SO_4$; C=methanol; D=acetonitrile.

|         | A (%) | B (%) | C (%) | D (%) |
|---------|-------|-------|-------|-------|
| 0–2 min | 70    | 30    | 0     | 0     |
| 15 min  | 32    | 30    | 19    | 19    |
| 30 min  | 28    | 30    | 21    | 21    |
| 35–40 min | 0   | 30    | 35    | 35    |
| 45 min  | 70    | 30    | 0     | 0     |
| 55 min  | 70    | 30    | 0     | 0     |

Retention time: $^{177}$Lu-Compound 42 (Example 15)=23.1 min.

4. $^{177}$Lu-Compound 58 (Example 16)

HPLC column: Zorbax Bonus-RP, 5 µm, 80 Å pore, 250 mm×4.6 mm (Agilent).

Mobile phase: A=water; B=water containing 30 mM $(NH_4)_2SO_4$.

Gradient: Isocratic with 40% A/60% B

Retention time: $^{177}$Lu-Compound 58 (Example 16)=9.3 min.

EXAMPLE 21

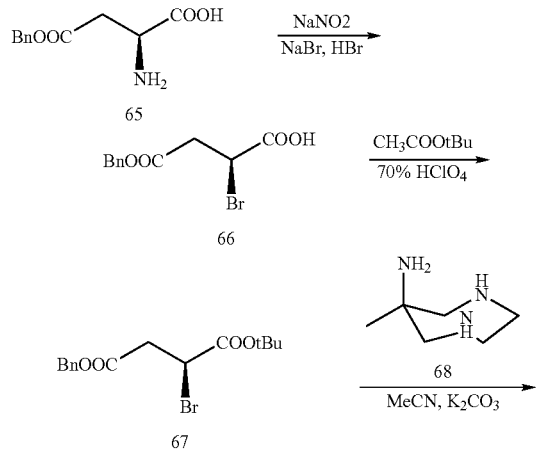

Scheme 1
An Aazta derivative functionalized at both R1, which allow attachment of two targeting groups from the carboxyl groups.

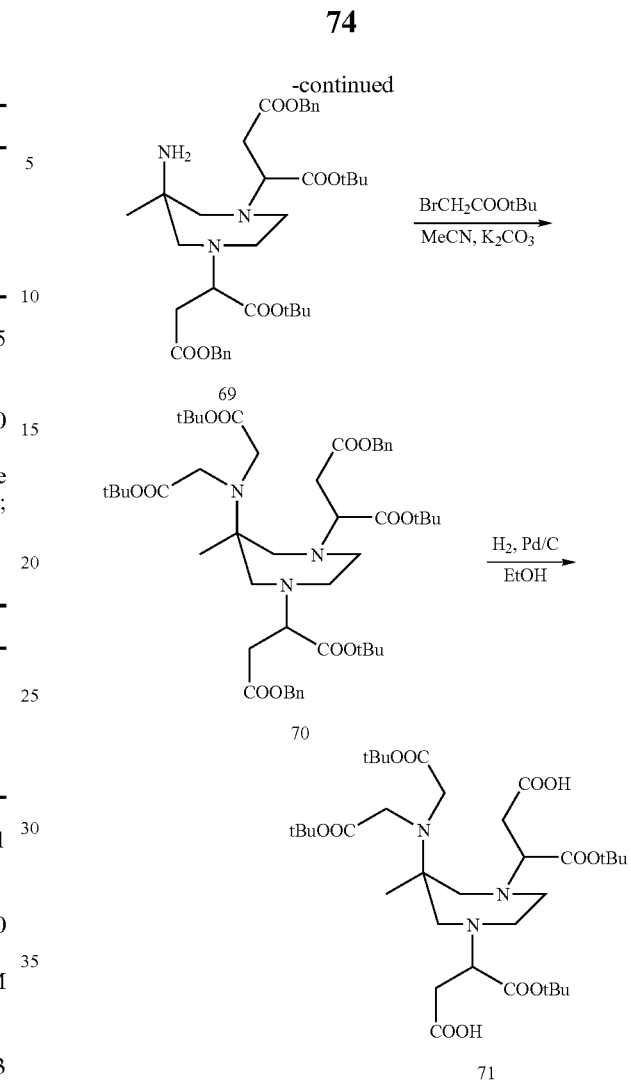

Compound 66 (Scheme 1)

A solution of $NaNO_2$ (5.88 g; 85.2 mmol) in water (60 mL) was added dropwise in 30 min to a mixture of L-aspartic acid β benzyl ester 65 (commercial product) (10.0 g; 44.8 mmol) and NaBr (17.1 g; 165.8 mmol) in 1 N HBr (200 mL) cooled to 0° C. After 3 h at 0° C. conc. $H_2SO_4$ (4.4 mL) was added and the solution extracted with $Et_2O$ (3×200 mL). The combined organic phases were washed with brine (2×200 mL), dried ($Na_2SO_4$) and evaporated under reduced pressure. The crude product was purified by flash chromatography to give 66 (9.3 g) as a colourless oil. Yield 73%.

Compound 67 (Scheme 1)

A solution of compound 66 (9.3 g; 27.1 mmol) in t-butyl acetate (100 mL) and 70% $HClO_4$ (0.08 mL) was stirred at room temperature for 12 h. Water (300 mL) was added and the solution was extracted with EtOAc (3×100 mL). The combined organic phases were washed with 5% aq. $Na_2CO_3$ (200 mL), water (200 mL) and then dried ($Na_2SO_4$) and evaporated under reduced pressure. The crude product was purified by flash chromatography to give 67 (8.4 g) as a colourless oil. Yield 90%.

Compound 69 (Scheme 1)

A mixture of 67 (5.98 g; 17.4 mmol), 6-amino-6-methyl-perhydro-1,4-diazepine 68 (Aime, S. et al. Inorg. Chem. 2004, 43, 7588) (0.5 g; 3.9 mmol) and $K_2CO_3$ (2.4 g; 17.4 mmol) in MeCN (50 mL) was stirred for 24 h. The solution was evaporated under reduced pressure and then water (100 mL) and CHCl₃ (100 mL) were added. The organic phase was dried (Na₂SO₄) and evaporated. The crude product was purified by flash chromatography to give 69 (1.3 g) as a pale yellow oil. Yield 37%.

Compound 70 (Scheme 1)

t-Butyl bromoacetate (0.32 mL; 2.18 mmol) was added to a stirred solution of 69 (0.80 g; 0.87 mmol), K₂CO₃ (0.46 g; 3.32 mmol) and Na₂SO₄ (0.22 g) in MeCN (8 mL) cooled at 0° C. After 30 min at room temperature the solution was refluxed for 5 h and 30 min. After 14 h at room temperature, the solution was evaporated and treated with 8:2 petroleum ether/EtOAc (20 mL). The precipitate was discharged and the liquid phase evaporated to give a crude (0.90 g) that was purified by flash chromatography to give 70 (0.66 g) as a yellow oil. Yield 86%.

Compound 71 (Scheme 1)

5% Pd/C (0.18 g) was added to a solution of compound 70 (0.60 g; 0.68 mmol) in abs. EtOH (50 mL). The reaction mixture was stirred under a hydrogen atmosphere for 1 h. The mixture was filtered through a Millipore® apparatus (FH 0.5 µm) and evaporated to give 71 (0.41 g) as a white solid. Yield 89%.

The final compound or a derivatized version including, e.g. one or more targeting moieties, may be labeled with, for example, Gd or ¹⁷⁷Lu, using procedures known in the art or disclosed herein.

EXAMPLE 22

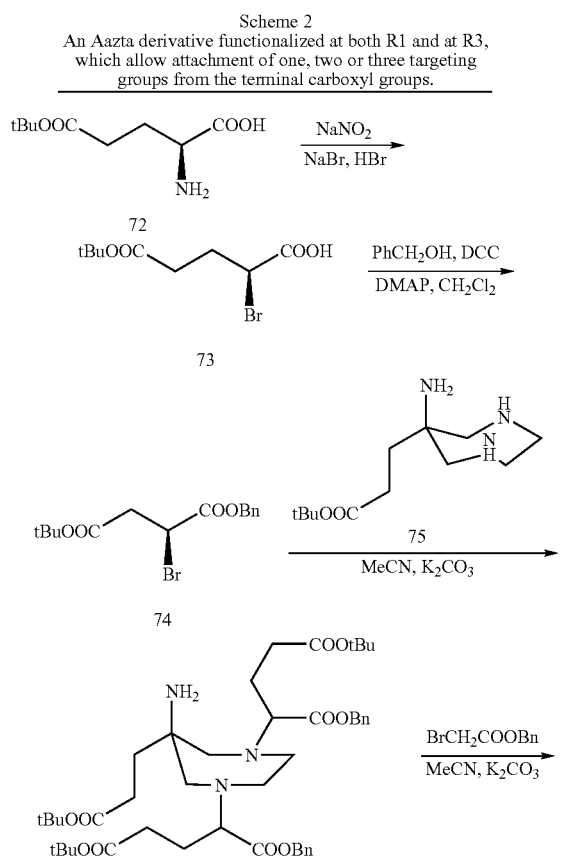

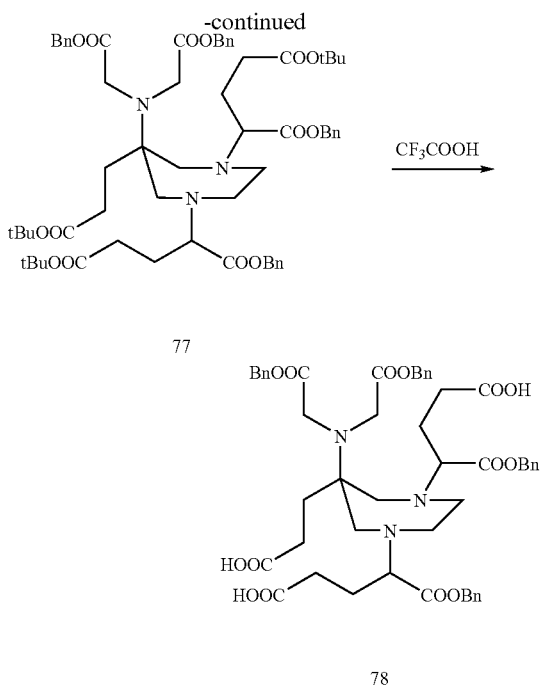

Compound 72 (Scheme 2)

A solution of NaNO₂ (1.35 g; 19.6 mmol) in water (15 mL) was added dropwise over 30 min to a mixture of L-glutamic acid 5-tbutyl ester 72 (commercial product) (2.0 g; 9.8 mmol) and KBr (4.31 g; 36.0 mmol) in 1 N HBr (45 mL) cooled to 0° C. After 3 h at 0° C. the solution was extracted with EtOAc (3×100 mL). The combined organic phases were washed with brine (80 mL), dried (Na₂SO₄) and evaporated under reduced pressure. The crude product was purified by column chromatography to give (0.53 g) 73 as a colourless oil. Yield 20%.

Compound 74 (Scheme 2)

A solution of compound 73 (1.38 g; 5.2 mmol), benzyl alcohol (0.58 mL; 5.7 mmol), N,N'-dicyclohexylcarbodiimide (DCC) (1.18 g; 5.7 mmol) and 4-dimethylaminopyridine (DMAP) (0.06 g; 0.52 mmol) in CH₂Cl₂ (25 mL) and was stirred at room temperature for 3 h. The precipitated dicyclohexylurea was filtered off and the filtrate was washed with 5% aq. AcOH (20 mL) and water (3×20 mL), dried (Na₂SO₄) and evaporated under reduced pressure. The crude product was purified by column chromatography to give 74 (1.31 g) as a colourless oil. Yield 71%.

Compound 76 (Scheme 2)

A solution of 74 (1.30 g; 3.65 mmol) in MeCN (2 mL) was added dropwise over 5 min. to a mixture of 6-amino-hexahydro-1H-1,4-diazepine-6-propanoic acid 1,1-dimethylethyl ester 75 (Aime, S. et al. Inorg. Chem. 2004, 43, 7588) (0.40 g; 1.66 mmol) and K₂CO₃ (0.57 g; 4.15 mmol) in MeCN (13 mL) cooled at 0° C. The reaction mixture was allowed to warm to rt and stirred for 29 h. Salts were filtered off and the filtrate evaporated under reduced pressure. The crude product was purified by column chromatography to give 76 (0.91 g) as a yellow oil. Yield 69%.

Compound 77 (Scheme 2)

Benzyl bromoacetate (0.41 mL; 2.60 mmol) was added to a mixture of 76 (0.83 g; 1.05 mmol), K₂CO₃ (0.41 g; 2.80 mmol) and Na₂SO₄ (0.22 g) in MeCN (5 mL) cooled to 0° C. After the addition, the reaction mixture was allowed to warm to room temperature, refluxed for 6 h. Further amounts of benzyl bromoacetate (0.05 g; 0.30 mmol) and K₂CO₃ (0.04 g; 0.28 mmol) were added to the mixture that was refluxed for more 8 h. The mixture was filtered, evaporated and the residue taken up with CH$_2$Cl$_2$ (10 mL). The organic phase was washed with water (2×10 mL), dried (Na$_2$SO$_4$) and evaporated under reduced pressure. The crude was purified by column chromatography to give 77 (0.22 g) as a yellow oil. Yield 19%.

Compound 78 (Scheme 2)

A solution of compound 77 (0.22 g; 0.20 mmol) in CF$_3$COOH (2.5 mL) was stirred at room temperature for 60 h. The mixture was then evaporated, the residue taken up with CH$_2$Cl$_2$ (10 mL) and the solution evaporated under reduced pressure. The operation was repeated two more times to afford a crude that was purified by column chromatography to give 78 (0.12 g) as a pale yellow oil. Yield 65%.

The final compound or a derivatized version including, e.g. one or more targeting moieties, may be labeled with, for example, Gd or $^{177}$Lu, using procedures known in the art or disclosed herein.

EXAMPLE 23

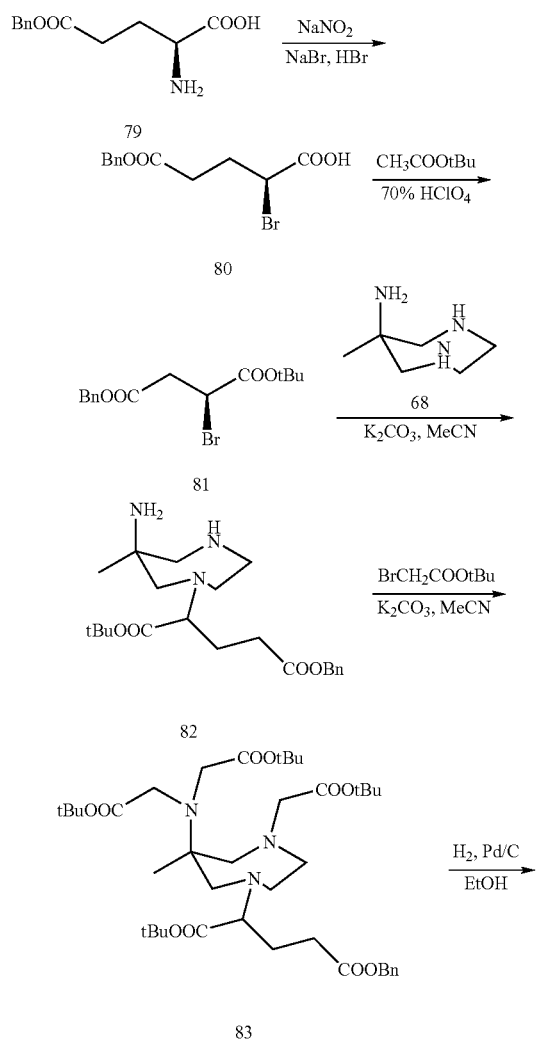

Scheme 3
An Aazta derivative functionalized at one R1, which allow attachment of a targeting group from the terminal carboxyl group

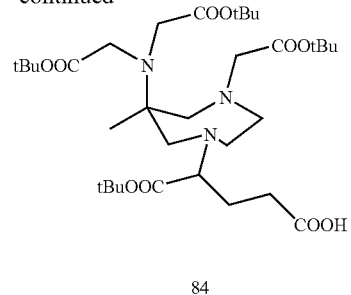

84

Compound 80 (Scheme 3)

A solution of L-glutamic acid γ benzyl ester 79 (commercial product) (20 g, 84.3 mmol) in 1M HBr (400 mL) was cooled to −7° C. under mechanical stirring, then NaBr (32.1 g, 311.9 mmol) was added. A solution of NaNO$_2$ (11.05 g, 160.2 mmol) in water (40 mL) was dropped into the reaction solution in 35 min. After 1 h, conc.H$_2$SO$_4$ (10 mL) was added and the mixture was extracted with Et$_2$O (4×200 mL); the combined organic phases were washed with brine (2×150 mL), dried (Na$_2$SO$_4$) and evaporated at reduced pressure. The crude was purified by column chromatography to give the desired product 80 (13.79 g). Yield: 54%.

Compound 81 (Scheme 3)

Compound 79 (13.46 g, 44.7 mmol) was dissolved in tert-butylacetate (79 mL), then 70% HClO$_4$ was added (193 μL) and the solution stirred at room temperature. Water (180 mL) was added after 24 h and the organic phase was separated, washed with water (130 mL), 5% aq. NaHCO$_3$ (130 mL) and water again (130 mL), dried (Na$_2$SO$_4$) and evaporated at reduced pressure. The crude was purified by column chromatography to give the product 81 (10.75 g). Yield: 67%.

Compound 82 (Scheme 3)

A solution of bromoderivative 81 (5.5 g; 15.4 mmol) in MeCN (30 mL) was dropped in 35 min into a suspension of 6-amino-6-methyl-perhydro-1,4-diazepine 68 (Aime, S. et al. Inorg. Chem. 2004, 43, 7588) (6.62 g; 51.3 mmol) and K$_2$CO$_3$ (2.13 g; 15.4 mmol) in MeCN (130 mL) cooled with an ice bath. After this time, the cooling bath was removed and the reaction mixture was stirred at room temperature. After 4 h the mixture was filtered and the solvent evaporated at reduced pressure. The crude was dissolved in EtOAc (150 mL) and washed with water (3×100 mL). The organic phase was washed with diluted HBr, the aqueous phase was brought to pH 9 with 25% NH$_4$OH, then extracted with EtOAc (4×70 mL). The combined organic phases were washed with water (100 mL), dried over Na$_2$SO$_4$ and evaporated to give the product 82 (4.8 g). Yield: 77%.

Compound 83 (Scheme 3)

t-Butyl bromoacetate (7.86 g, 40.3 mmol) was added to a suspension of compound 82 (4.65 g, 11.5 mmol), K$_2$CO$_3$ (6.36 g, 46 mmol) and Na$_2$SO$_4$ (1.5 g, 10.6 mmol) in MeCN (80 mL) and the mixture was heated at reflux. After 16 h the mixture was filtered and evaporated at reduced pressure. The crude was purified by flash chromatography to give the desired product 83 (7.24 g). Yield: 84%.

Compound 84 (Scheme 3)

Compound 83 (572 mg, 0.77 mmol) was dissolved in EtOH (50 mL) and hydrogenated on 10% Pd/C (100 mg) at atmospheric pressure. The mixture was filtered through a Millipore® apparatus (FH 0.5 μm) and evaporated at reduced pressure to give product 84 (430 mg). Yield: 85%.

The final compound or a derivatized version including, e.g. a targeting moiety, may be de-protected and labeled with, for example, Gd or $^{177}$Lu, using procedures known in the art or disclosed herein.

EXAMPLE 24

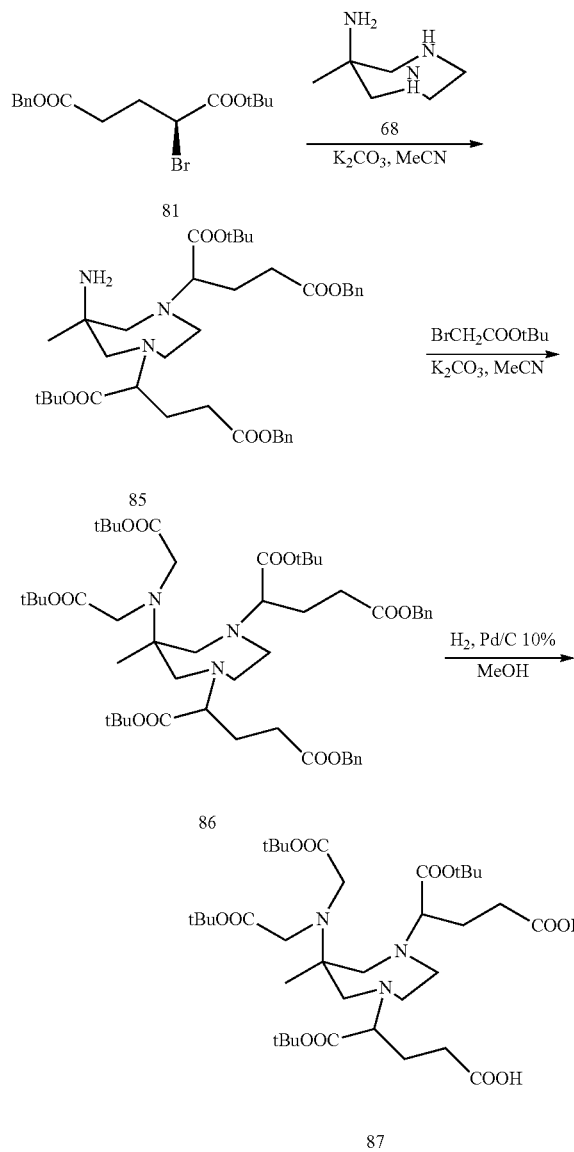

Compound 85 (Scheme 4)

A mixture of 81 (see EXAMPLE 3) (1.7 g; 4.8 mmol), 6-amino-6-methyl-perhydro-1,4-diazepine 68 (Aime, S. et al. *Inorg. Chem.* 2004, 43, 7588) (0.25 g; 1.9 mmol) and K$_2$CO$_3$ (0.67 g; 4.8 mmol) in MeCN (10 mL) was stirred for 72 h. The suspension was filtered and evaporated under reduced pressure. The residue was dissolved in CH$_2$Cl$_2$ (30 mL), then washed with water (2×20 mL) and brine (2×20 mL). After separation the organic phase was dried (Na$_2$SO$_4$) and evaporated. The crude product was purified by flash chromatography to give 85 (1.1 g) as a yellow oil. Yield 85%.

Compound 86 (Scheme 4)

t-Butyl bromoacetate (0.41 mL; 2.79 mmol) was added to a stirred solution of 85 (0.76 g; 1.11 mmol), K$_2$CO$_3$ (0.54 g; 3.90 mmol) and Na$_2$SO$_4$ (0.3 g) in MeCN (20 mL) cooled to 0° C. After the addition, the suspension was refluxed under nitrogen for 15 h then stirred at 60° C. for another 15 h. More t-butyl bromoacetate (0.41 mL; 2.79 mmol) was added and the reaction mixture was stirred at reflux for 8 h then at 60° C. for 15 h. The suspension was cooled to room temperature, filtered and the solvent evaporated. The residue was dissolved in CH$_2$Cl$_2$ (20 mL) and washed with H$_2$O (2×10 mL) and 5% aq. NaHCO$_3$ (2×10 mL). The organic phase was dried (Na$_2$SO$_4$), filtered and evaporated. The crude orange oil was purified by flash chromatography to give 86 (0.65 g) as a yellow oil. Yield 64%.

Compound 86 (Scheme 4)

10% Pd/C (100 mg) was added to a solution of compound 86 (0.5 g; 0.55 mmol) in MeOH (20 mL). The reaction mixture was stirred under hydrogen atmosphere for 5 h. The mixture was filtered through a Millipore® apparatus (FH 0.5 μm) and evaporated to give 87 (0.4 g) as a yellow solid. Yield 99%.

The final compound or a derivatized version including, e.g. one or more targeting moieties, may be de-protected and labeled with, for example, Gd or $^{177}$Lu, using procedures known in the art or disclosed herein.

EXAMPLE 25

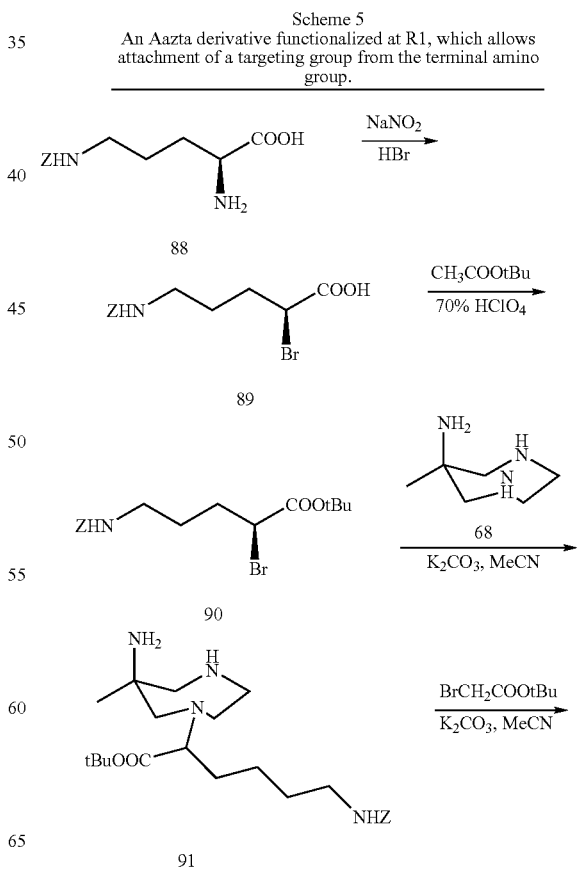

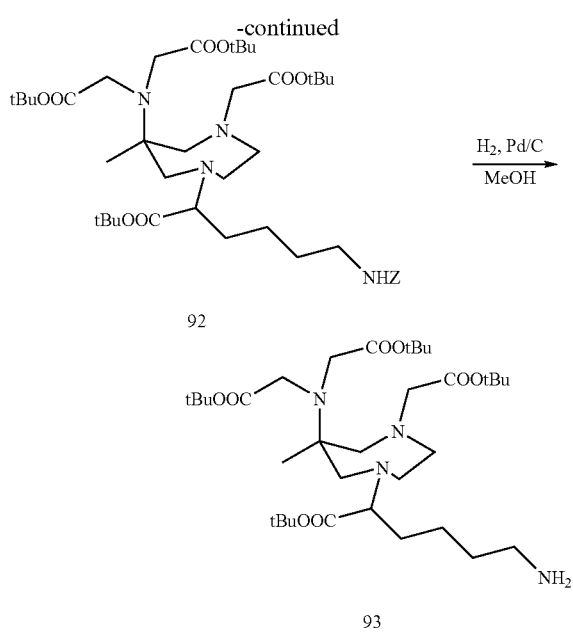

Compound 89 (Scheme 5)

$N^\epsilon$-carbobenzyloxy-L-lysine 88 (commercial product) (15 g; 0.052 mol) was dissolved in 6M HBr (45 mL) at 0° C. $NaNO_2$ (3.97 g; 0.057 mol) was added in little portions over 30 min. The reaction solution was stirred at room temperature for 2 h, then extracted with ethyl acetate (3×100 mL). The organic phase was dried ($Na_2SO_4$), filtered and evaporated under vacuum. The crude was purified by column chromatography to give the compound 89 (14.06 g) as an orange oil. Yield 79%.

Compound 90 (Scheme 5)

70% aq. $HClO_4$ (1.5 mL) was added dropwise to a solution of the compound 89 (13 g; 0.0377 mol) in tert-butylacetate (160 mL). The reaction mixture was stirred at room temperature for 24 h. Then was washed with water (2×200 mL) and with 5% aq. $NaHCO_3$ (2×150 mL). The organic phase was dried ($Na_2SO_4$), filtered and evaporated under vacuum. The crude was purified by column chromatography and the product 90 (9.66 g) was obtain as a yellow oil. Yield 64%.

Compound 91 (Scheme 5)

A solution of compound 90 (4.6 g; 0.115 mol) in MeCN (25 mL) was added dropwise in 30 min to a mixture of 6-amino-6-methyl-perhydro-1,4-diazepine 68 (Aime, S. et al. *Inorg. Chem.* 2004, 43, 7588) (5 g; 0.039 mol) and $K_2CO_3$ (1.59 g; 0.0115 mol) in MeCN (2.5 mL) at 0° C. The mixture was stirred at room temperature for 4 h then evaporated under vacuum. The crude was dissolved in EtOAc (25 mL) and washed with water (3×25 mL). The organic phaser was dried ($Na_2SO_4$), filtered and evaporated under vacuum. The crude was dissolved in EtOAc (25 mL) and washed with aq. HBr. The aqueous phases were collected, the pH was brought to 9 by addition of aq. $NH_4OH$ and extracted with ethyl acetate (3×100 mL). The organic phases were dried ($Na_2SO_4$) filtered and evaporated to give product 91 (3.3 g). Yield 64%.

Compound 92 (Scheme 5)

A solution of t-butyl bromoacetate (3.8 mL) in MeCN (20 mL) was added dropwise to a stirred suspension of compound 91 (3.28 g; 7.3 mmol), $K_2CO_3$ (3.6 g) and $Na_2SO_4$ (0.5 g) in MeCN (30 mL) at 0° C. At the end of the addition the mixture was heated at reflux for 14 h. Then was filtered and evaporated under vacuum. The crude was dissolved in $CH_2Cl_2$ (50 mL), washed with water (50 mL) and 5% aq. $NaHCO_3$ (2×50 mL); the organic layer was dried ($Na_2SO_4$), filtered and evaporated under vacuum. The crude was purified by column chromatography and the product 92 (3.32 g) was obtain like a yellow oil. Yield 58%.

Compound 93 (Scheme 5)

10% Pd/C (400 mg) was added to a solution of compound 92 (3.32 g; 42 mmol)) in MeOH (20 mL). The reaction mixture was stirred under hydrogen atmosphere for 2 h. The mixture was filtered through aMillipore® apparatus (FH 0.5 μm) and evaporated to give compound 93 (2.42 g) as a yellow oil. Yield 90%.

The final compound or a derivatized version including, e.g. one or more targeting moieties, may be de-protected and labeled with, for example, Gd or $^{177}Lu$, using procedures known in the art or disclosed herein.

EXAMPLE 26

Biodistribution and Tumor Targeting Studies Using Compound 41 of Example 14 and Compound 42 of Example 15, which Target GRP Receptors The tumor targeting capacity, biodistribution and kinetics of two compounds of the invention including a targeting moiety which targets GRP receptors ($^{177}Lu$-Compound 41 of Example 14 and $^{177}Lu$-Compound 42 of Example 15) and one compound of the invention which does not include a targeting moiety (Compound 94) were evaluated in the human PC-3 nude mouse model, (PC-3 tumor cells express GRP receptors). The compounds of the invention were also compared to $^{177}Lu$-AMBA, a compound which contains the same targeting moiety as Compounds 41 and 42 and which has demonstrated efficacy for delivering radioactivity to PC-3 tumours for radiotherapeutic purposes.

10-50 μCi of the HPLC purified compounds were administered to each mouse by i.v. tail vein injection, n=4 per group. At 1 h, 1 and 7 days post injection, the mice were terminated and the organs and tissues were harvested. Radioactivity was assayed in a gamma counter. The data was expressed as percentage of the total administered radioactivity (% ID) for the urine combined with the bladder, as well as for the blood pool; and percentage of the total administered radioactivity per gram (% ID/g) for all the other tested organs

| Cmpd | Tumor 1 h % ID/g | Tumor 24 h % ID/g | Tumor 7 d % ID/g | Blood 1 h % ID | Blood 24 h % ID | Blood 7 d % ID | Urine/ Blad 1 h % ID | Femur 7 d % ID/g | Carcass 7 d % ID/g |
|---|---|---|---|---|---|---|---|---|---|
| Compound 94 | 0.47 ± .21 | 0.03 ± 0.01 | 0.01 ± 0.00* | 0.39 ± 0.29 | 0.01 ± 0.01 | 0.00 ± 0.00* | 53.9 ± 30.6 | 0.19 ± 0.04* | 0.38 ± 0.02* |
| Compound 41 | 4.49 ± 1.72 | 1.89 ± 0.55 | 0.49 ± 0.13 | 0.39 ± 0.07 | 0.01 ± 0.00 | 0.00 ± 0.00 | 56.6 ± 12.3 | 0.14 ± 0.02 | 0.50 ± 0.01 |

-continued

| Cmpd | Tumor 1 h % ID/g | Tumor 24 h % ID/g | Tumor 7 d % ID/g | Blood 1 h % ID | Blood 24 h % ID | Blood 7 d % ID | Urine/ Blad 1 h % ID | Femur 7 d % ID/g | Carcass 7 d % ID/g |
|---|---|---|---|---|---|---|---|---|---|
| Compound 42 | 1.82 ± 0.06 | 0.76 ± 0.35 | 0.12 ± 0.04 | 1.82 ± 0.06 | 0.00 ± 0.00 | 0.00 ± 0.00 | 51.9 ± 19.7 | ND | 0.07 ± 0.01 |
| AMBA | 5.86 ± 1.91 | 1.82 ± 0.06 | 0.34 ± 0.16 | 1.23 ± 0.58 | 0.02 ± 0.00 | 0.00 ± 0.00 | 43.4 ± 4.3 | 0.06 ± 0.03 | 0.17 ± 0.01 |

*72 h timepoint,
ND—not done

The data show that the Lu-177 administered as a complex of the underivatised cyclohexylaazta (Compound 94), which does not include a GRP receptor targteing moiety, is rapidly cleared from the body with little residual localization in any organs or tissue. When the complex is derivatized with the GRP targeting peptide (as in Compounds 41 and 42) the radioactivity shows localization in the tumour. The data are similar to those of $^{177}$Lu-AMBA, a compound with demonstrated efficacy for delivering radioactivity to PC-3 tumours for radiotherapeutic purposes. The tumour localization and lack of retention of radioactivity in the other tissue of the body show the utility of these two chelators as a means of radiolabelling targeting agents such as peptides for in vivo use.

The structures of AMBA is immediately below. The structure of Compound 94 follows:

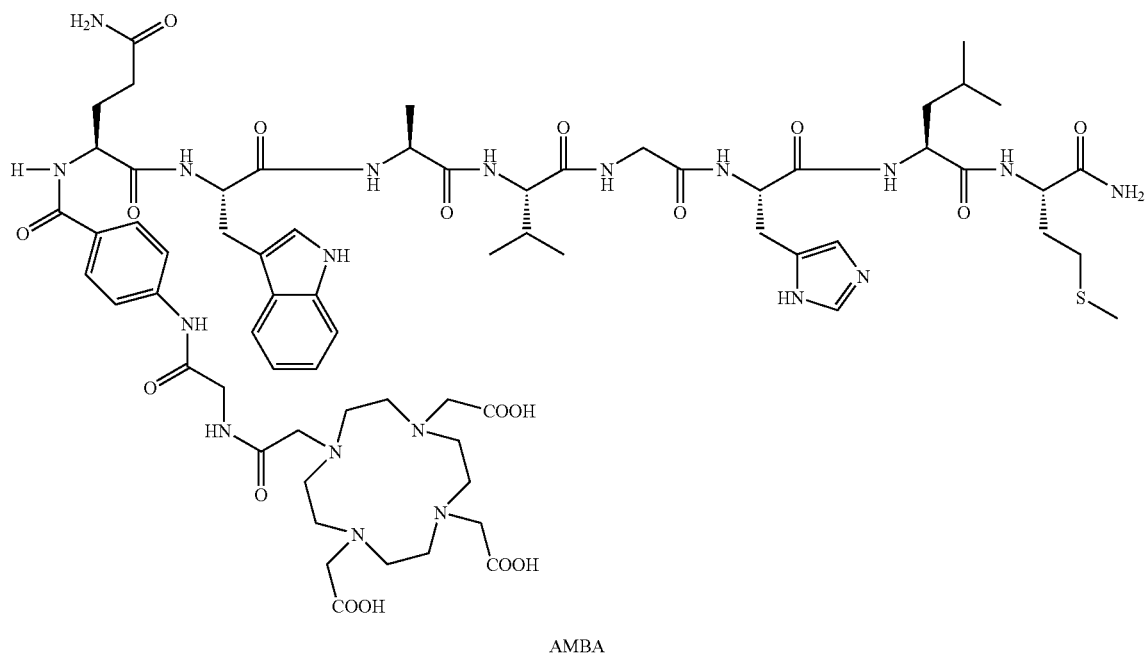

AMBA

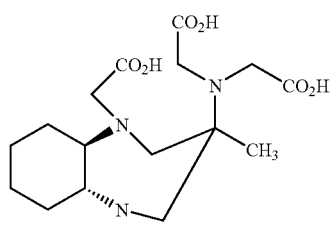

Compound 94

The invention claimed is:
1. A compound of general formula (I):

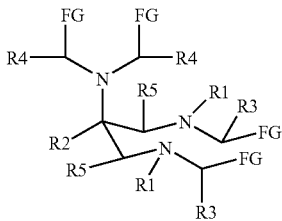

in which:
R$_1$ is hydrogen, C$_1$-C$_{20}$ alkyl, C$_3$-C$_{10}$ cycloalkyl, C$_4$-C$_{20}$ cycloalkylalkyl, aryl, arylalkyl or the two R$_1$ groups, taken together, form a straight or cyclic C$_2$-C$_{10}$ alkylene group or an ortho-disubstituted arylene;
R$_2$ is hydrogen, carboxy, or an optionally substituted group selected from C$_1$-C$_{20}$ alkyl, C$_3$-C$_{10}$ cycloalkyl, C$_4$-C$_{20}$ cycloalkylalkyl, aryl, arylalkyl, a group bearing an acidic moiety, and a group bearing an amino moiety, each of which may be further optionally substituted with functional groups selected from the group consisting of carboxyl, amino, aldehydes, haloalkyl, maleimidoalkyl, hydroxyl and sulfhydryl groups which allow conjugation with a suitable molecule able to interact with physiological systems;
R$_3$, R$_4$ and R$_5$, which are the same or different, are hydrogen, carboxy, or an optionally substituted group selected from C$_1$-C$_{20}$ alkyl, C$_3$-C$_{10}$ cycloalkyl, C$_4$-C$_{20}$ cycloalkylalkyl, aryl, arylalkyl, a group bearing an acidic moiety and a group bearing an amino moiety, each of which may be further optionally substituted with functional groups selected from the group consisting of carboxyl, amino, aldehydes, haloalkyl, maleimidoalkyl, hydroxyl and sulfhydryl groups which allow conjugation with a suitable molecule able to interact with physiological systems;
FG, which are the same or different, are carboxy, —PO$_3$H$_2$ or —RP(O)OH groups, wherein R is hydrogen, or an optionally substituted group selected from C$_1$-C$_{20}$ alkyl, C$_3$-C$_{10}$ cycloalkyl, C$_4$-C$_{20}$ cycloalkylalkyl, aryl, arylalkyl, a group bearing an acidic moiety and a group bearing an amino moiety, each of which may be further optionally substituted with functional groups selected from the group consisting of carboxyl, amino, aldehydes, haloalkyl, maleimidoalkyl, hydroxyl and sulfhydryl groups which allow conjugation with a suitable molecule able to interact with physiological systems;
as well as the salts thereof with physiologically compatible bases or acids.

2. The compound of claim 1 complexed with a metal selected from the group consisting of the metal elements having atomic number ranging between 20 and 31, 39, 42, 43, 44, 49, and between 57 and 83, chosen among Fe($^{2+}$), Fe($^{3+}$), Cu($^{2+}$), Cr(3+), Gd($^{3+}$), Eu($^{3+}$), Dy($^{3+}$), La($^{3+}$), Yb($^{3+}$), Mn($^{2+}$), Mn($^{3+}$), Co($^{2+}$), Ni($^{2+}$), Pr($^{3+}$), Nd($^{3+}$), Sm($^{3+}$), Gd($^{3+}$), Tb($^{3+}$), Ho($^{3+}$) and Er($^{3+}$) and radioisotopes chosen among $^{203}$Pb, $^{67}$Ga, $^{68}$Ga, $^{72}$As, $^{111}$In, $^{113}$In, $^{90}$Y, $^{97}$Ru, $^{62}$Cu, $^{64}$Cu, $^{52}$Fe, $^{52m}$Mn, $^{140}$La, $^{175}$Yb, $^{153}$Sm, $^{166}$Ho, $^{149}$Pm, $^{177}$Lu, $^{142}$Pr, $^{159}$Gd, $^{212}$Bi, $^{47}$Sc, $^{149}$Pm, $^{67}$Cu, $^{111}$Ag, $^{199}$Au, $^{161}$Tb, $^{51}$Cr, $^{167}$Tm, $^{141}$Ce, $^{168}$Yb, $^{88}$Y, $^{165}$Dy, $^{166}$Dy, $^{97}$Ru, $^{103}$Ru, $^{186}$Re, $^{99m}$Tc, $^{211}$Bi, $^{213}$Bi, $^{214}$Bi, $^{105}$Rh, $^{109}$Pd, $^{177m}$Sn, $^{177}$Sn and $^{199}$Au.

3. The compound of claim 1, wherein FG is a carboxy group.

4. The compound of claim 1, wherein R$_2$ is alkyl, aryl or arylalkyl, optionally substituted with optionally protected carboxy or amino groups.

5. The compound of claim 1, wherein R$_3$ is hydrogen, R$_4$ is hydrogen or methyl, and R$_5$ is hydrogen.

6. The compound of claim 1, wherein the two R$_1$ groups form together an alkylene or a cyclic alkylene.

7. The compound of claim 5, wherein the two R$_1$ groups form together an ethylene group.

8. The compound of claim 1 wherein, within the meanings of any one of R$_2$, R$_3$, R$_4$, R$_5$ or R$_1$, the group bearing an acidic moiety is an optionally substituted group bearing a carboxylic moiety.

9. The compound of claim 1, wherein any functional group which allows conjugation with a suitable molecule able to interact with physiological systems is selected from carboxyl and amino groups.

10. An MRI contrast agent comprising the compounds of claim 1 complexed with a paramagnetic metal.

11. The compound of claim 2 complexed with a paramagnetic metal selected from the group consisting of Gd($^{3+}$), Eu($^{3+}$), Dy($^{3+}$), La($^{3+}$), Yb($^{3+}$) and Mn($^{2+}$).

12. The compound of claim 1 complexed with Gadolinium.

13. The compound of claim 1 complexed with a radioisotope.

14. A therapeutic or diagnostic composition comprising the compound of claim 2 in admixture with a suitable carrier.

15. A compound of formula (IX)

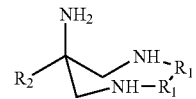

wherein the two R$_1$ groups form a straight or cyclic C$_2$-C$_{10}$ alkylene group or an ortho-disubstituted arylene.

16. The compound of claim 15, wherein the two R$_1$ groups are ethylene or propylene.

17. A method of imaging a patient comprising the steps of administering to such patient an effective amount of a diagnostic imaging agent comprising a compound of claim 1 in a diagnostically acceptable carrier, and imaging said patient.

18. The method of claim 17 wherein the imaging is MRI and the compound of formula (I) is complexed with a paramagnetic ion selected from the group consisting of Fe($^{2+}$), Fe($^{3+}$), Cu($^{2+}$), Cr(3+), Gd($^{3+}$), Eu($^{3+}$), Dy($^{3+}$), La($^{3+}$), Yb($^{3+}$) and Mn($^{2+}$).

19. The method of claim 17 wherein the imaging is radioimaging and the compound of formula (I) is complexed with a radioisotope useful for diagnosis.

20. A method of treating a patient comprising the steps of administering to such patient an effective amount of a therapeutic agent comprising a compound of claim 1 in physiologically acceptable carrier.

21. The method of claim 20 wherein the therapeutic is a radiotherapeutic and the compound is complexed with a therapeutic radioisotope.

22. A compound of formula (5):

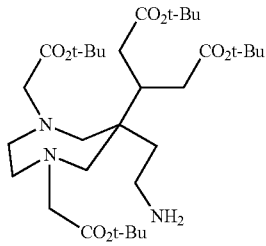

optionally de-protected, complexed with a metal and/or attached to a targeting moiety.

23. A method of making the compound of formula (5) of claim 22 which comprises the following reaction:

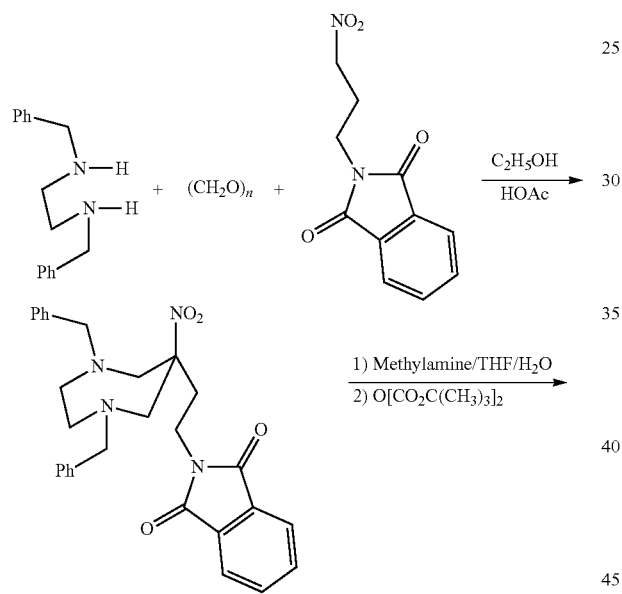

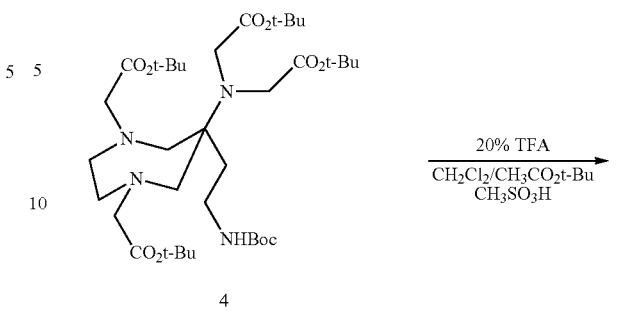

24. A compound of formula (25):

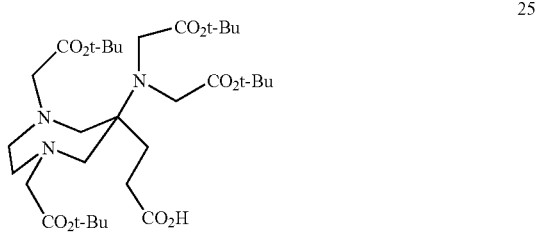

optionally de-protected, complexed with a metal and/or attached to a targeting moiety.

25. A method of making the compound (25) of claim 24 which comprises the following reaction:

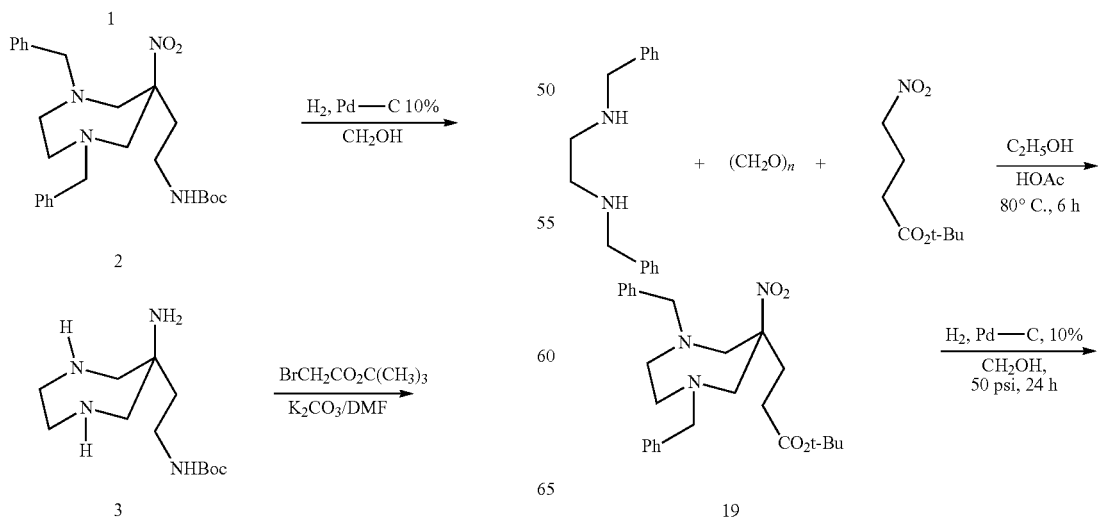

-continued
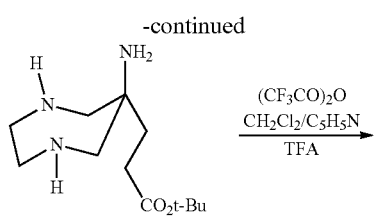
20
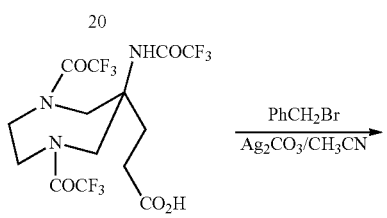
21
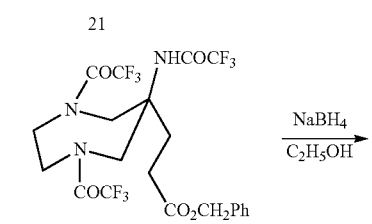
22
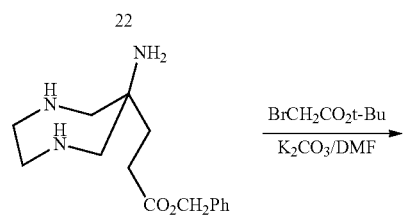
23
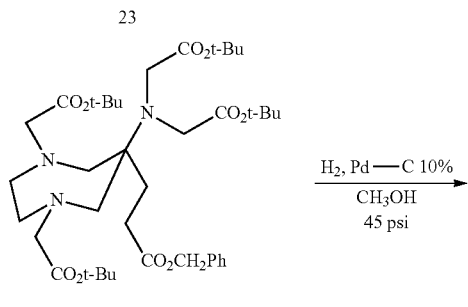
24
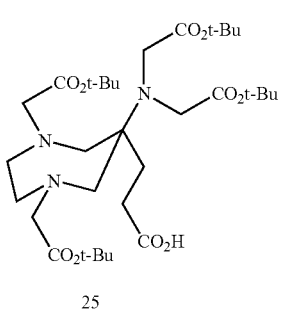
25
optionally de-protected, complexed with a metal and/or attached to a targeting moiety.
26. A compound of formula (30):
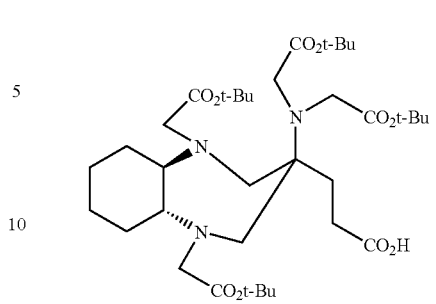
30
optionally de-protected, complexed with a metal and/or attached to a targeting moiety.
27. A method of making the compound (30) of claim 26 which comprises the following reaction:
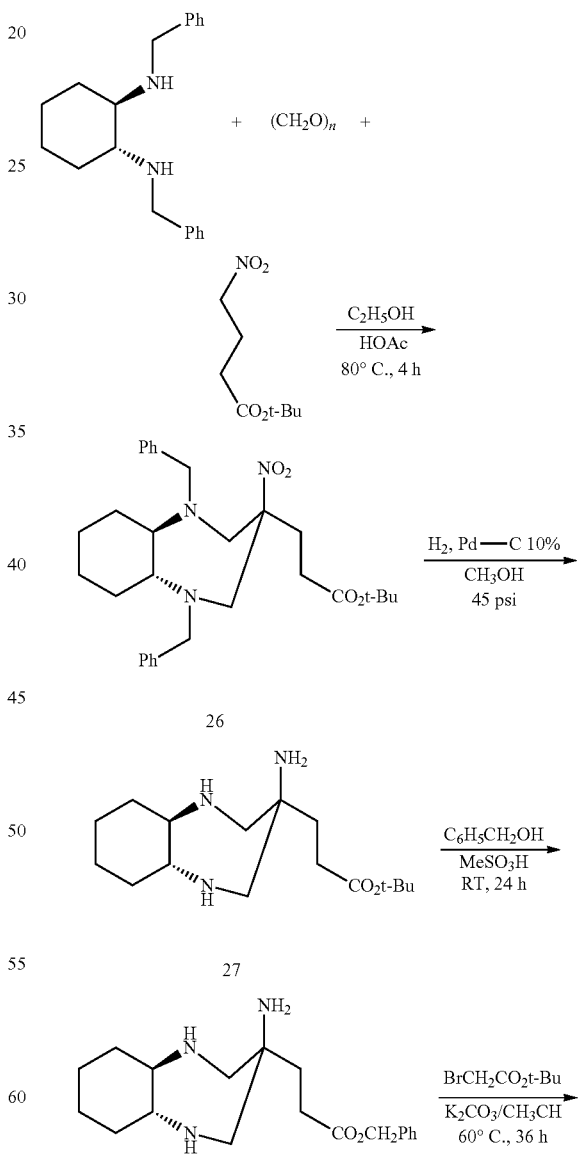

-continued
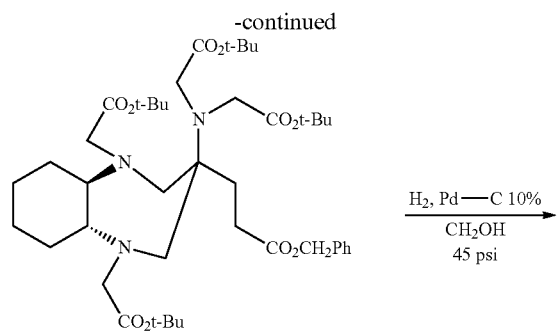
29
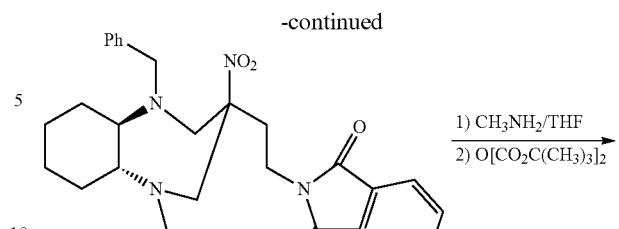
14
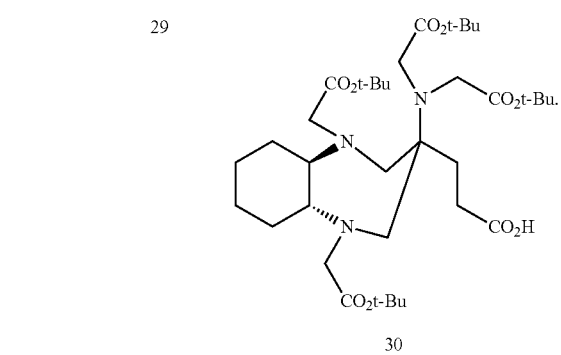
30
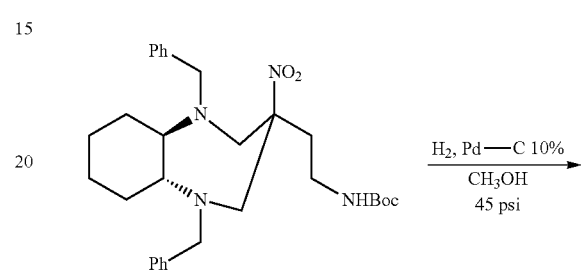
15
28. A compound of formula (18):
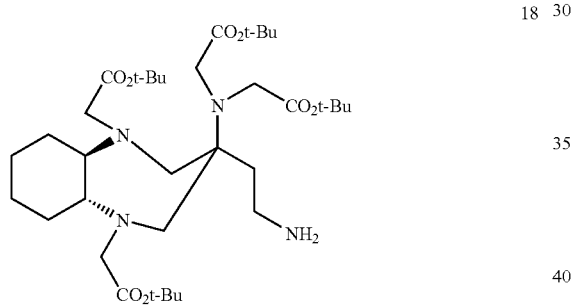
18
optionally de-protected, complexed with a metal and/or attached to a targeting moiety.
29. A method of making the compound of formula (18) of claim 28 which comprises the following reaction:
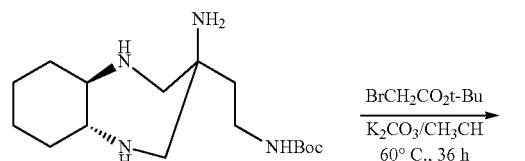
16
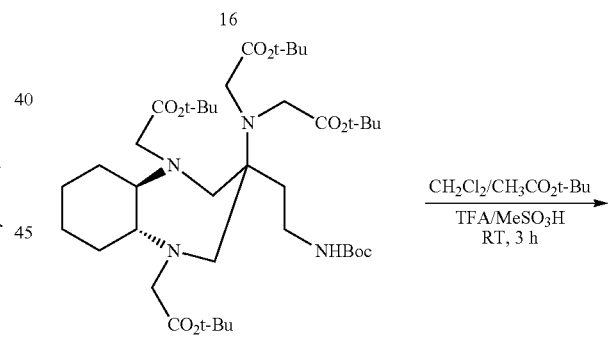
17
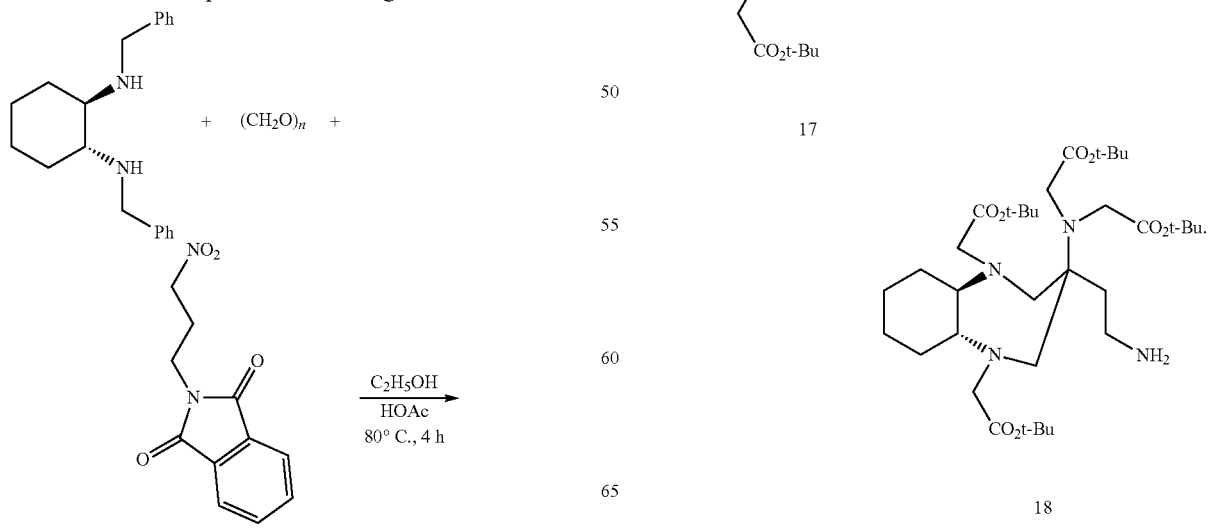

30. A method of coupling a fibrin-binding targeting peptide to compound (5) of claim 22 which comprises employing a reaction selected from the group consisting of:
(a)
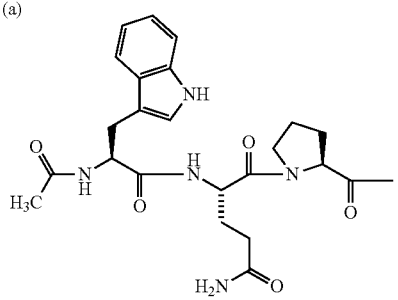
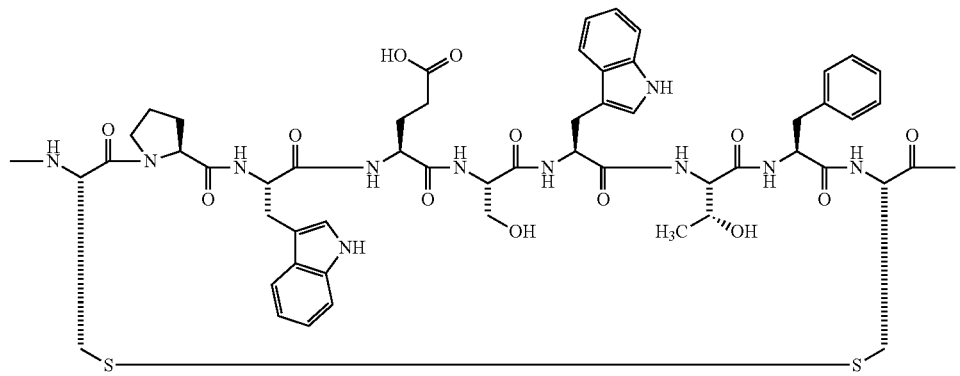
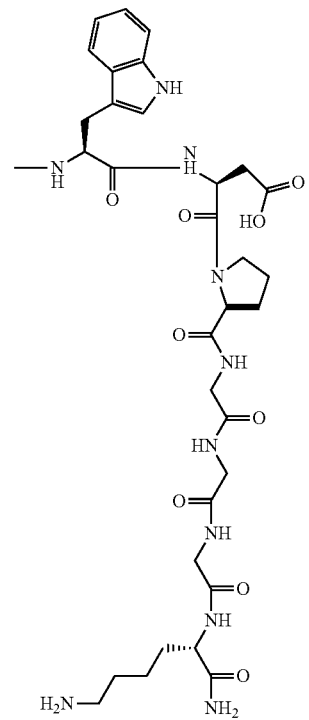

-continued
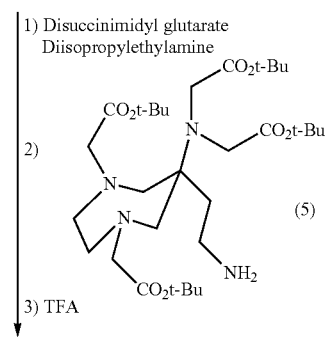
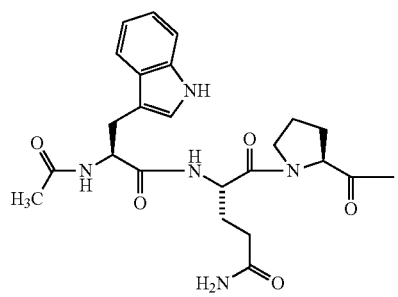
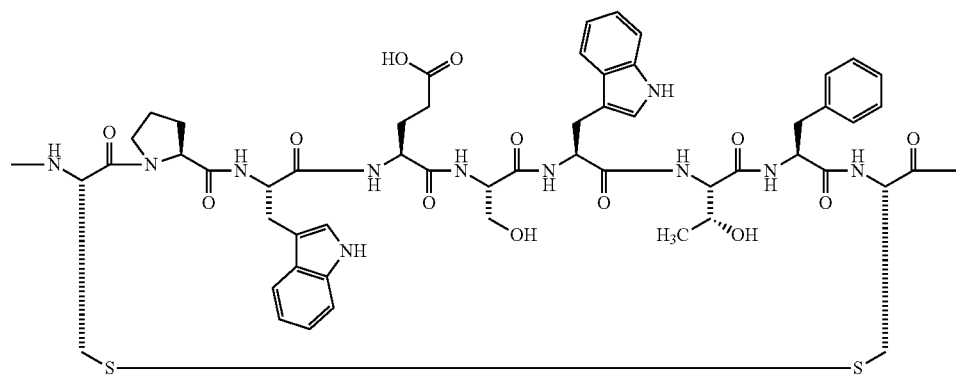

-continued
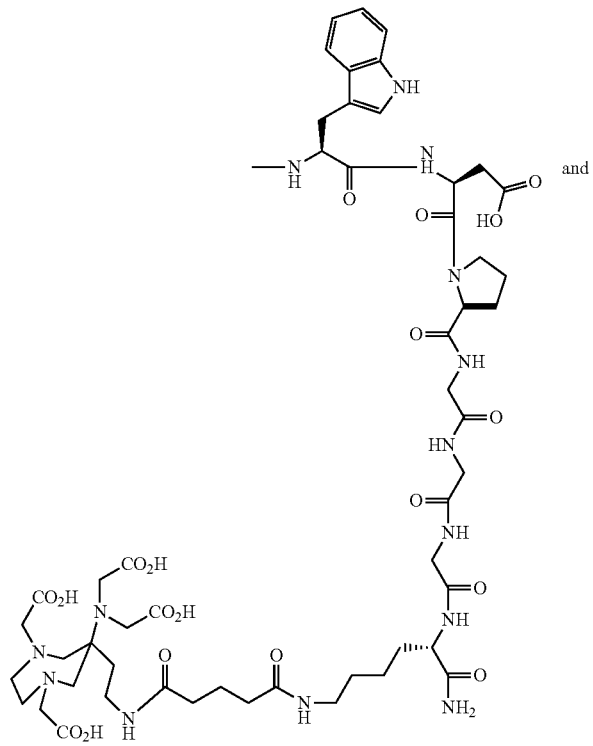
and
36
(b)
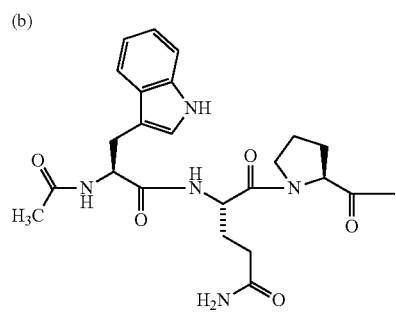
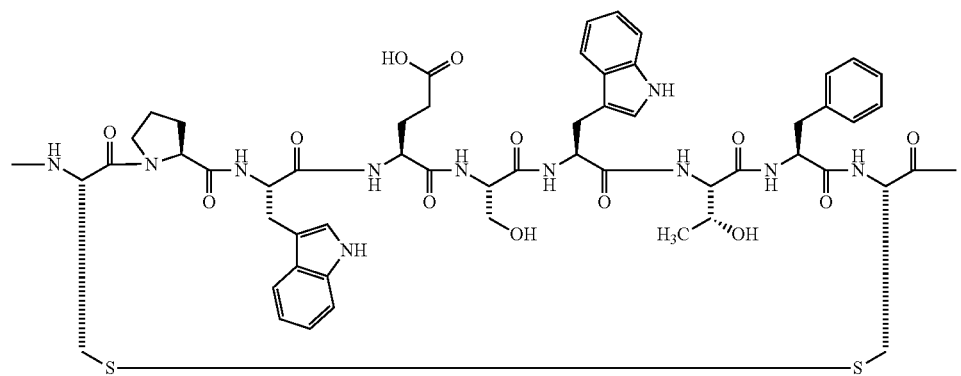

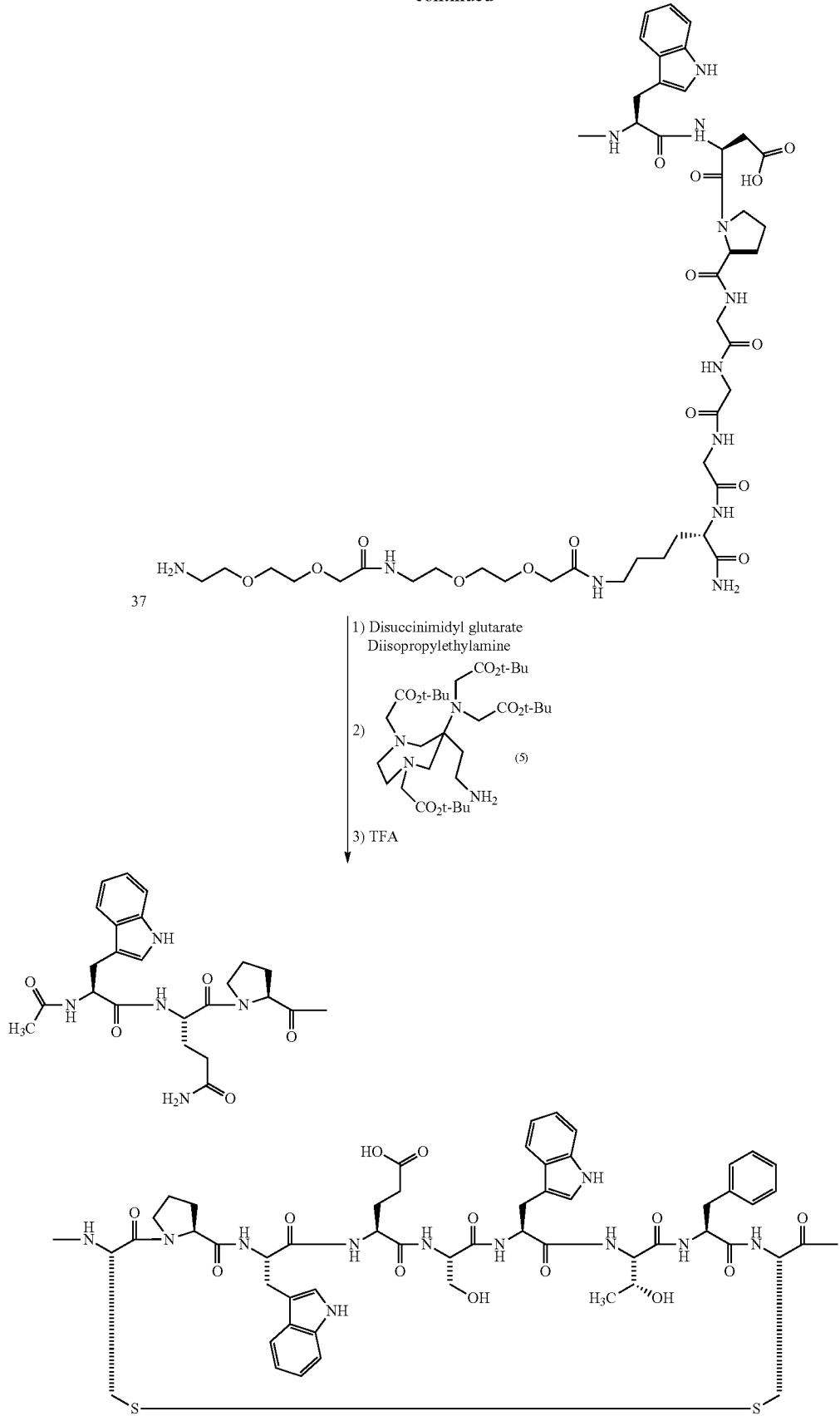

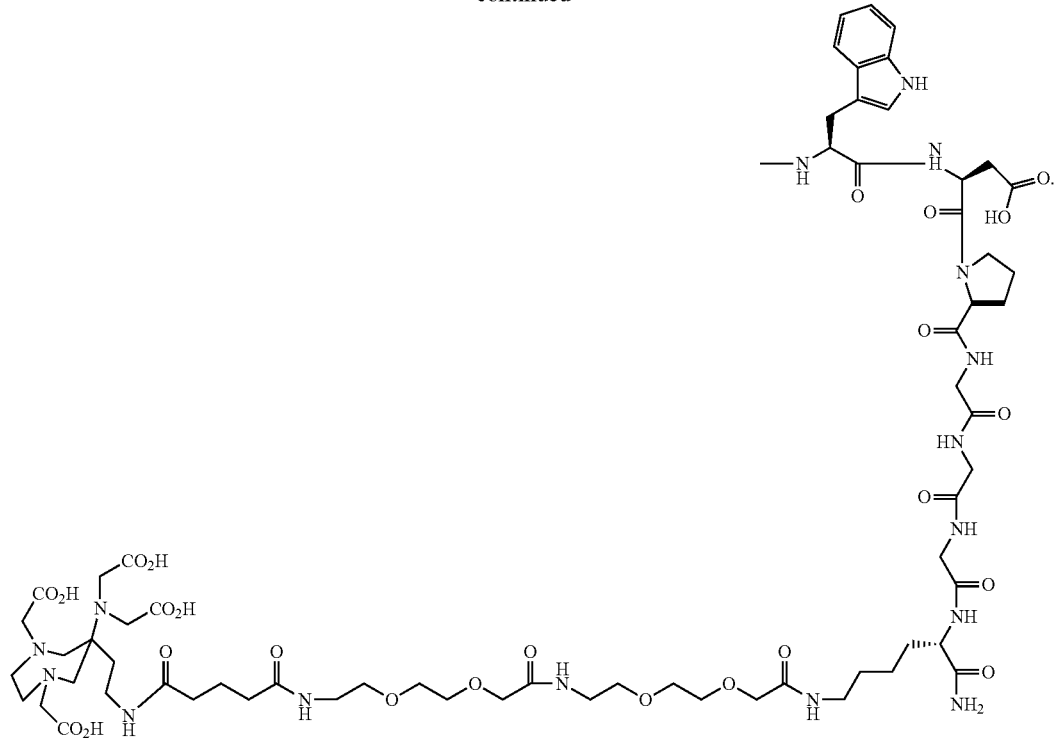
38
31. A method of coupling a fibrin-binding targeting peptide to compound (18) which comprises the following reaction, wherein compound (37) is the fibrin-binding targeting peptide from claim 30:
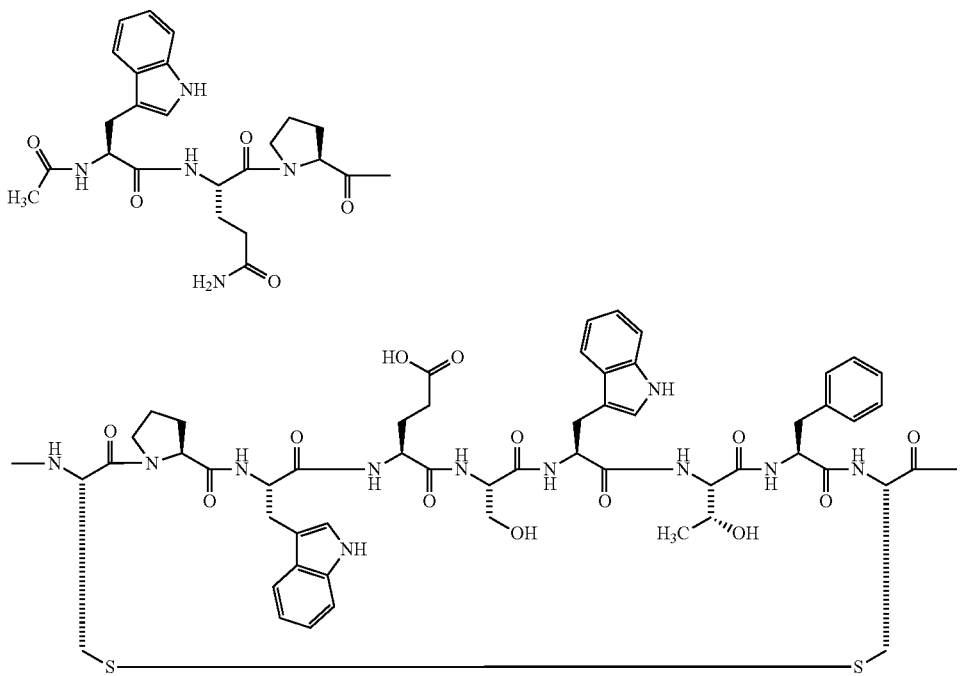

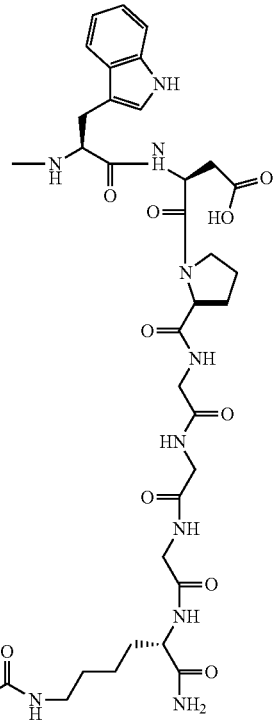
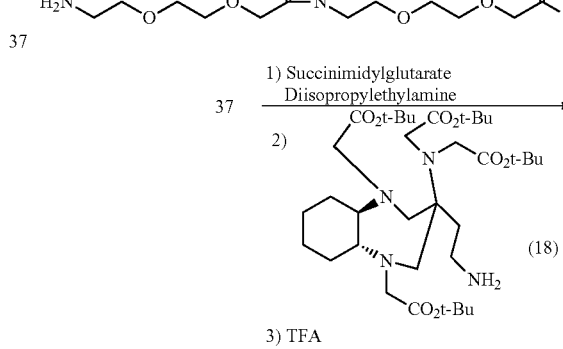
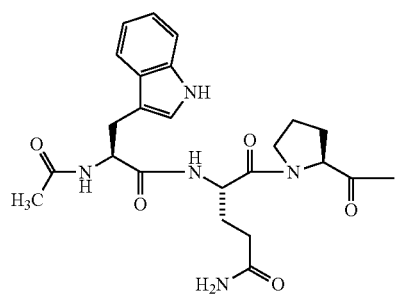
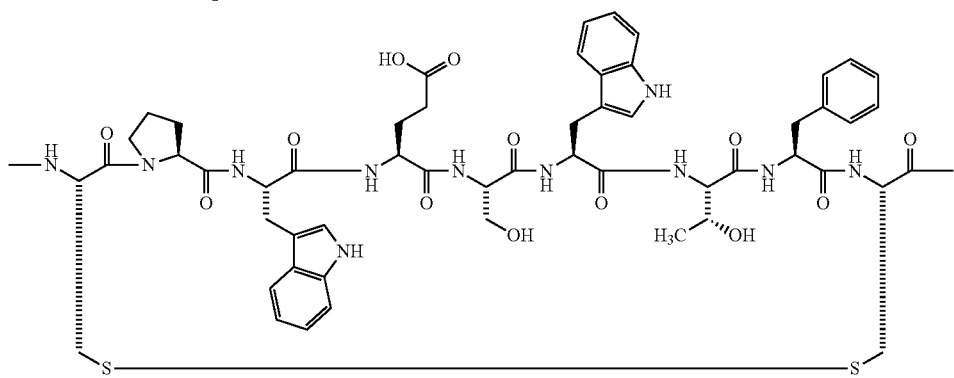

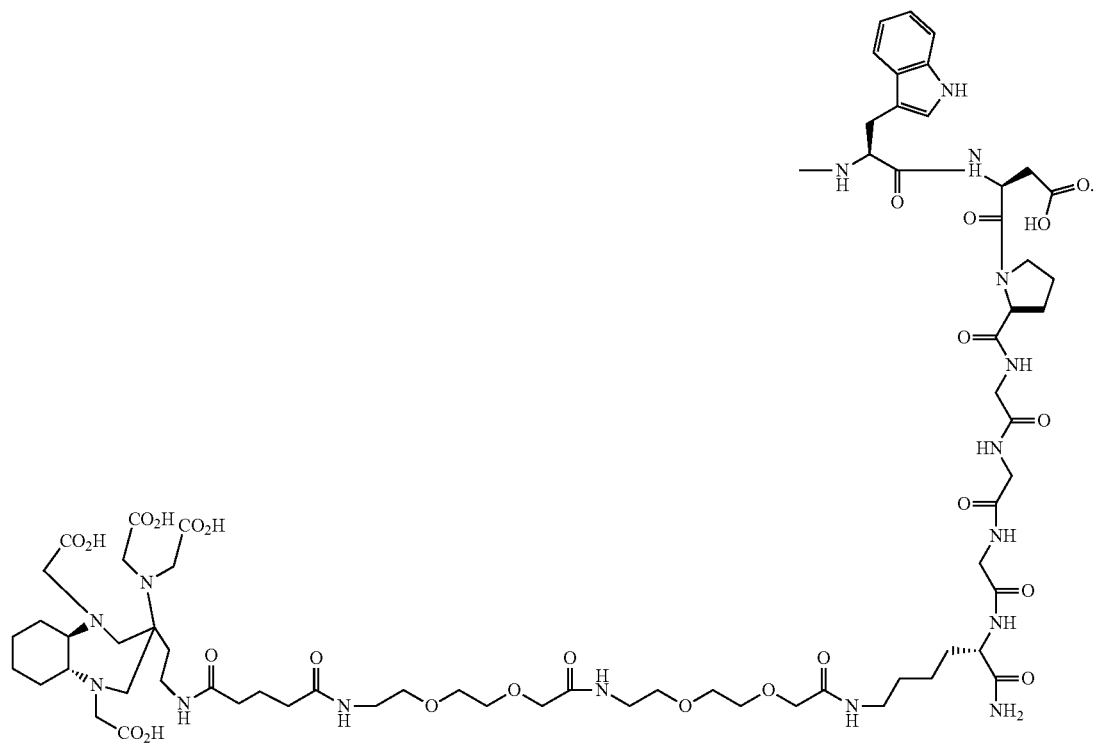
39
32. A method of coupling a fibrin-binding targeting peptide to compound (30) of claim 26 which comprises the following reaction:

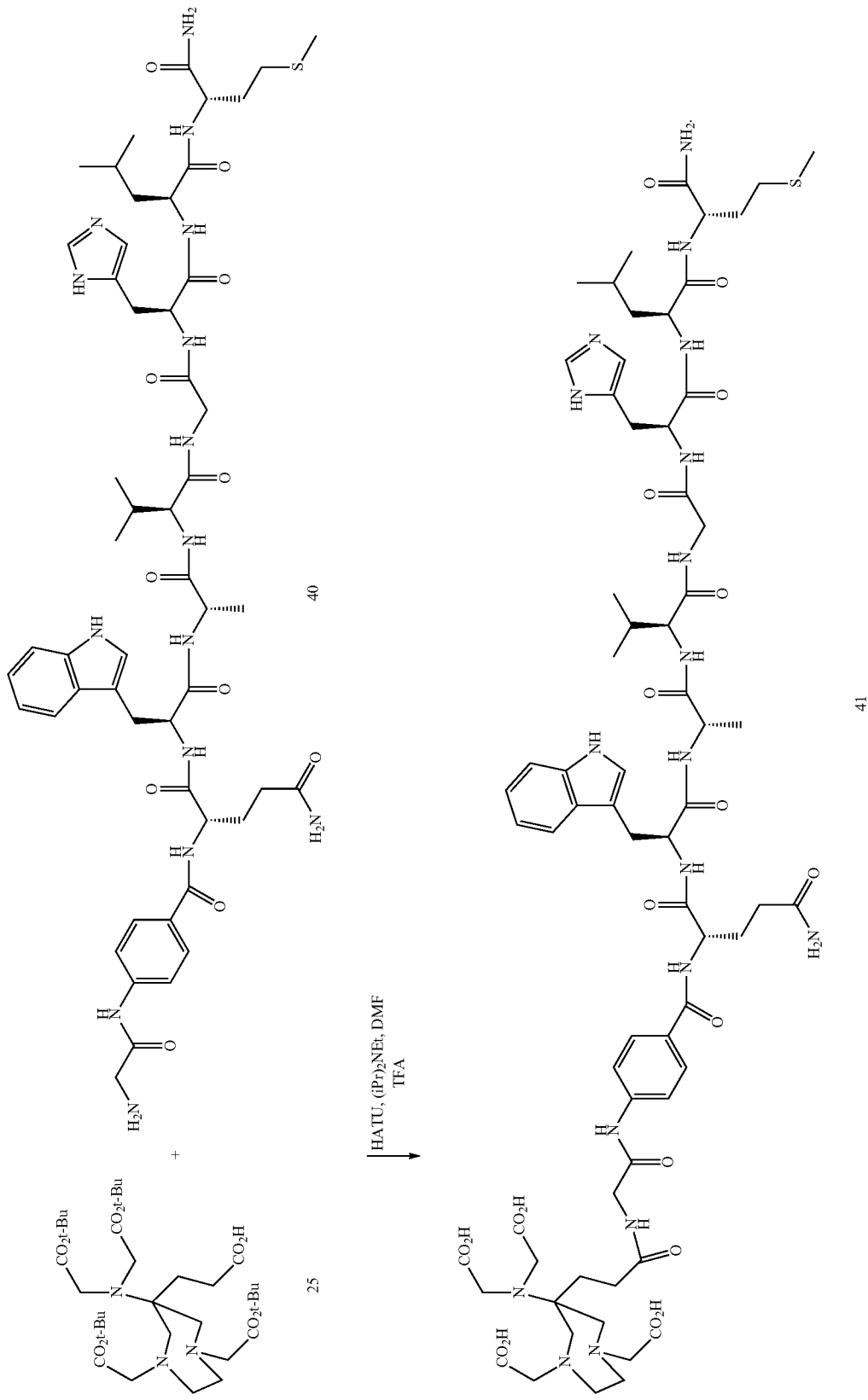

33. The method of claim 20 or 21 wherein the patient is to be treated for a tumor.

34. The method of claim 33 wherein the compound of formula (I) is conjugated to a molecule which will selectively bind to the tumor and the radioactive metal ion is therapeutically effective against the tumor.

35. A compound of formula (8):

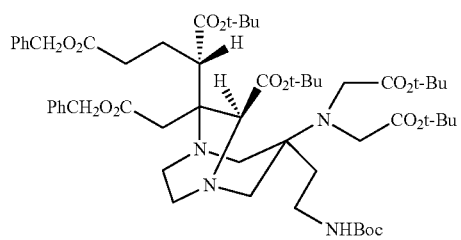

8 optionally de-protected, complexed with a metal and/or attached to a targeting moiety.

36. A compound of formula (13):

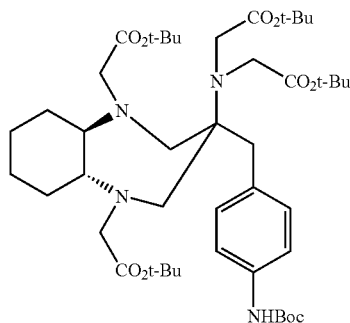

13 optionally de-protected, complexed with a metal and/or attached to a targeting moiety.

37. A compound of formula (71):

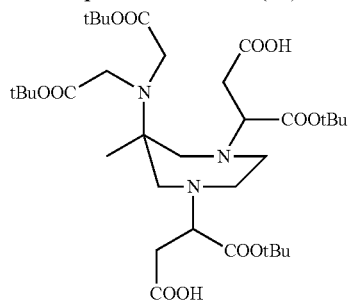

71 optionally de-protected, complexed with a metal and/or attached to a targeting moiety.

38. A compound of formula (78):

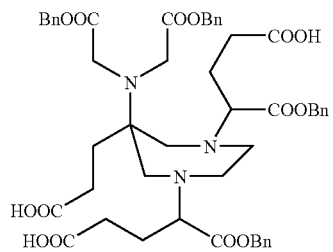

78 optionally de-protected, complexed with a metal and/or attached to a targeting moiety.

39. A compound of formula (84):

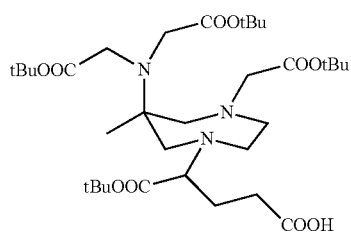

optionally de-protected, complexed with a metal and/or attached to a targeting moiety.

40. A compound of formula (87):

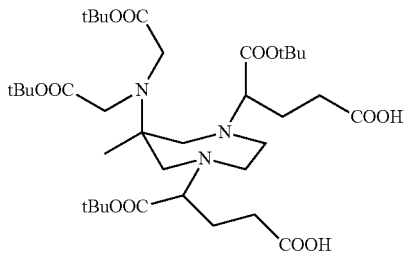

optionally de-protected, complexed with a metal and/or attached to a targeting moiety.

41. A compound of formula (93):

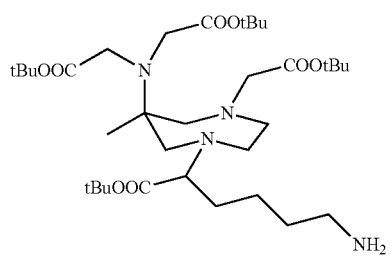

optionally de-protected, complexed with a metal and/or attached to a targeting moiety.

42. A compound of formula (34):

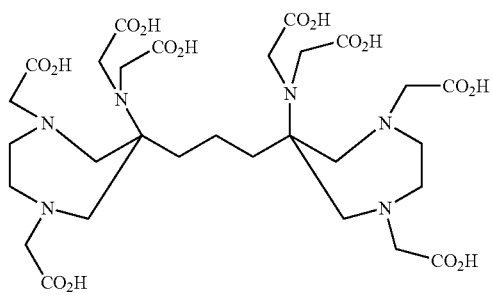

34 optionally complexed with a metal and/or attached to one or more targeting moiety.

43. A compound of formula (58):
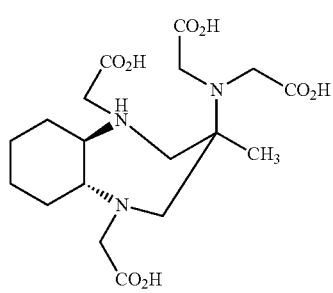
58
optionally complexed with a metal and/or attached to a targeting moiety.
44. A compound of the formula:
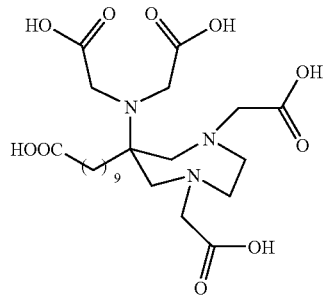
optionally complexed with a metal and/or attached to a targeting moiety.
45. A compound of the formula:
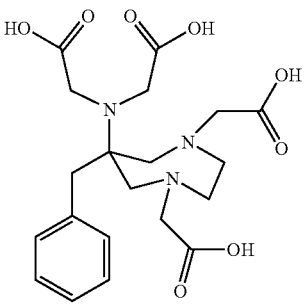
optionally complexed with a metal.
46. A compound of formula (64):
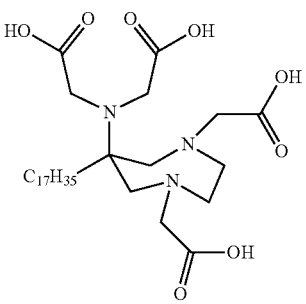
optionally complexed with a metal.
47. A compound of formula (36):
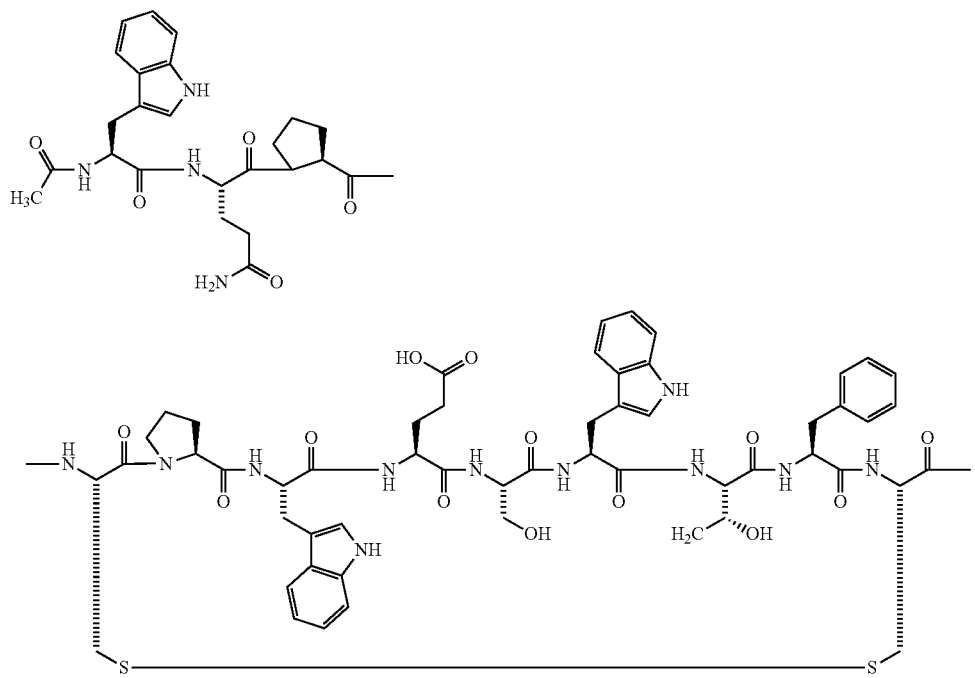

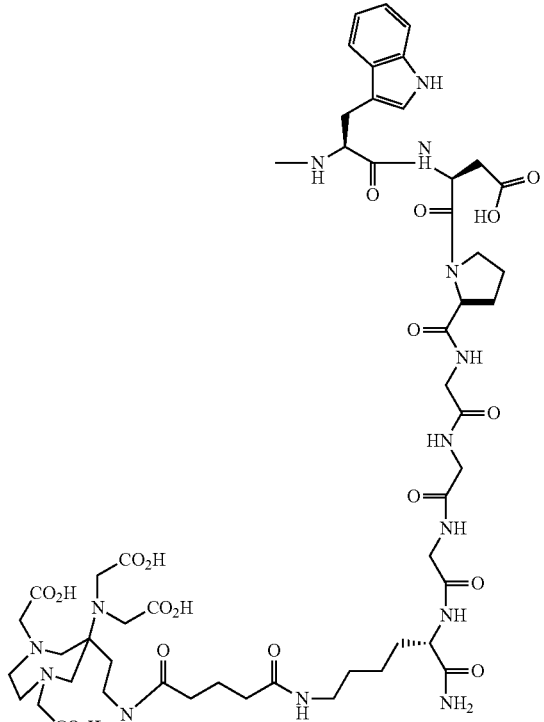
36
optionally complexed with a metal.
48. A compound of formula (38):
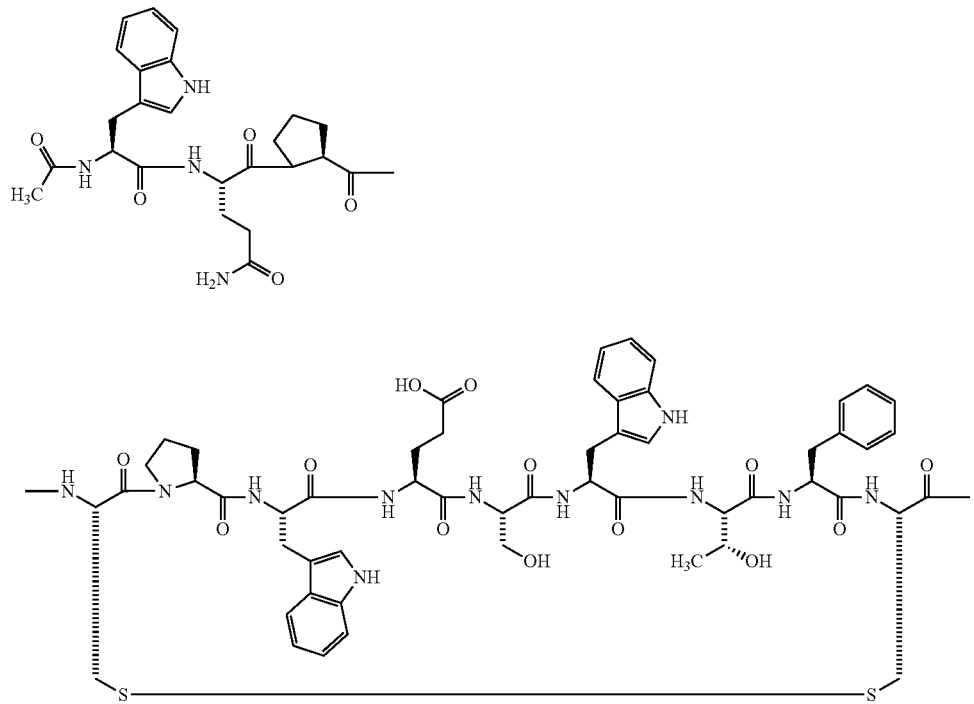

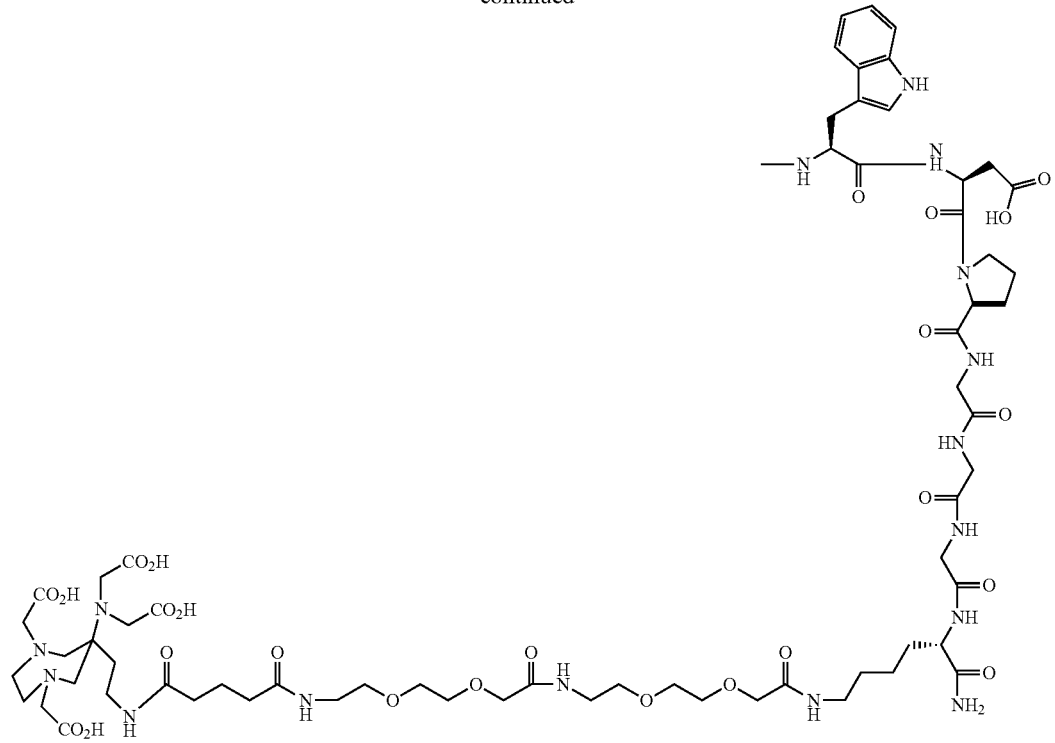
optionally complexed with a metal.
49. A compound of formula (39):
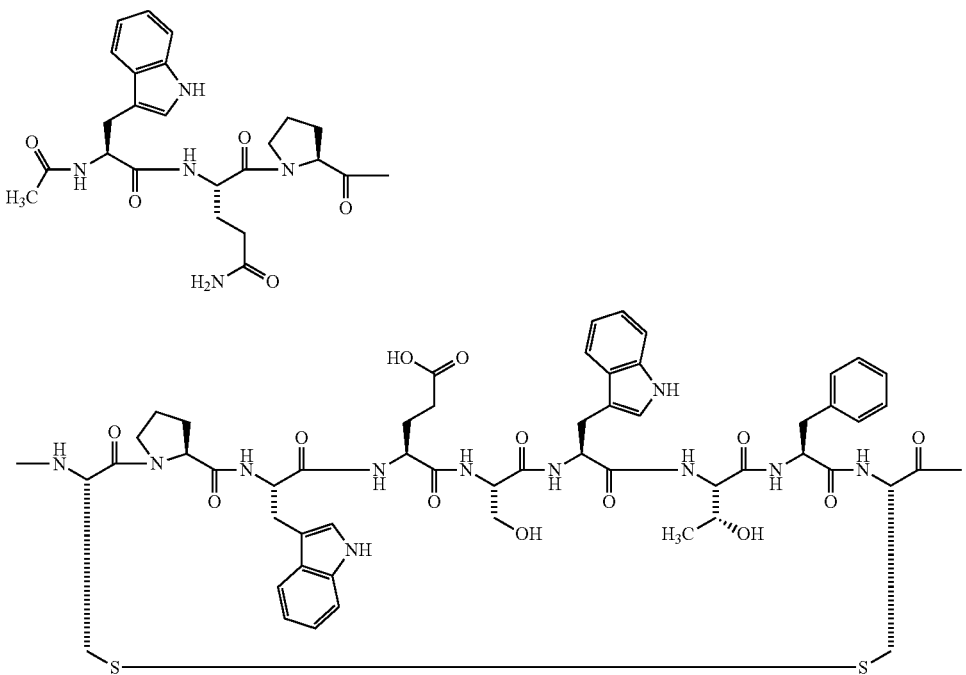

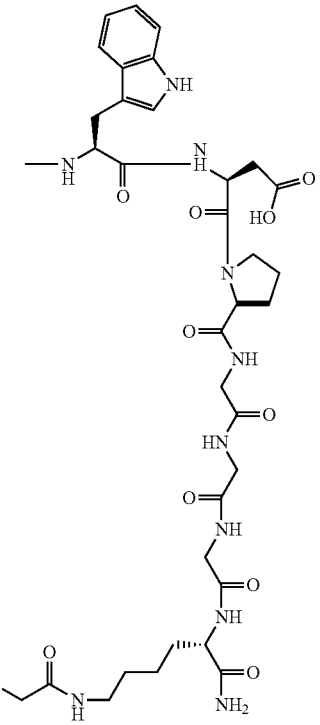
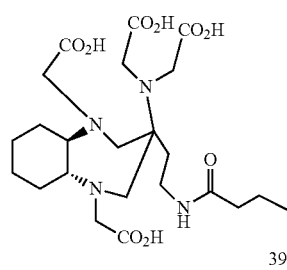
40
optionally complexed with a metal.
50. A compound of formula (41):
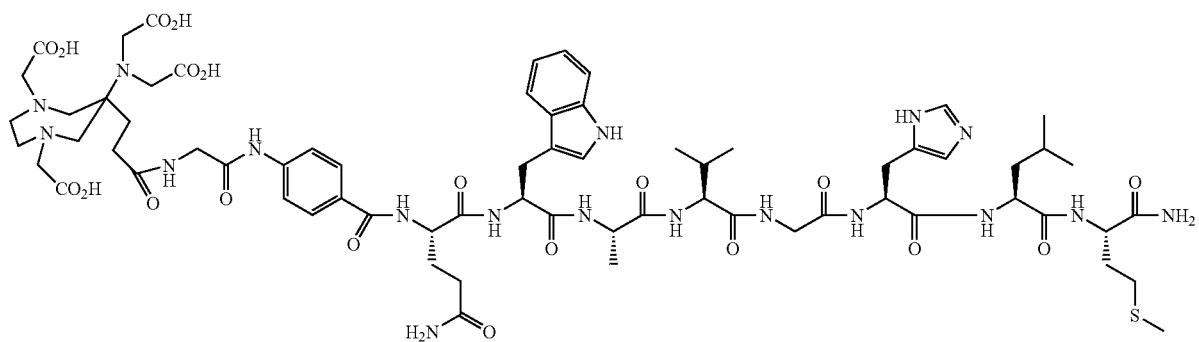
optionally complexed with a metal.

51. A compound of formula (42):

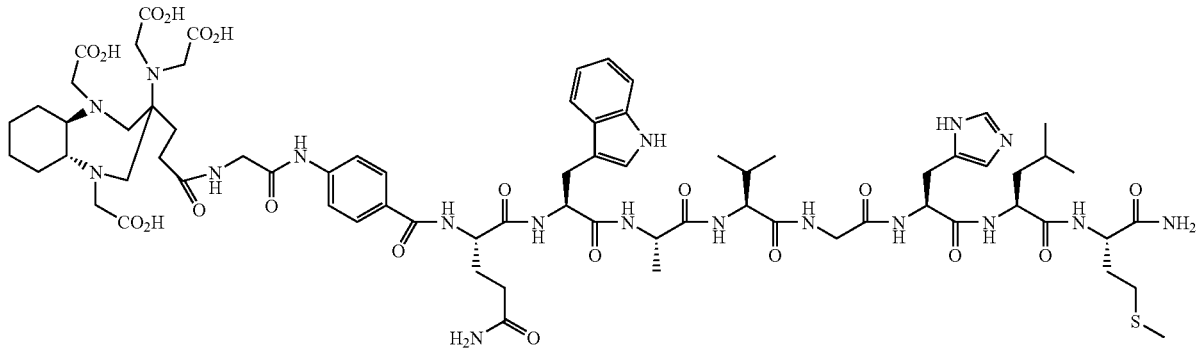

42 optionally complexed with a metal.

52. A method of treating cancer which comprises administering to a patient in need thereof a therapeutically effective amount of the compound 41 of claim 50 complexed with a therapeutic radioisotope, in a pharmaceutically or veterinarilly acceptable carrier.

53. A method of treating cancer which comprises administering to a patient in need thereof the compound 42 of claim 51 complexed with a therapeutic radioisotope, in a pharmaceutically or veterinarilly acceptable carrier.

54. A method of treating cardiovascular disease, fibrin containing blood clots, thrombus, plaques, or tumors which comprises administering to a patient in need thereof a therapeutically effective amount of the compound 36 of claim 47 complexed with a therapeutic radioisotope, in a pharmaceutically or veterinarilly acceptable carrier.

55. A method of treating cardiovascular disease, fibrin containing blood clots, thrombus, plaques, or tumors which comprises administering to a patient in need thereof a therapeutically effective amount of the compound 38 of claim 48 complexed with a therapeutic isotope, in a pharmaceutically or veterinarilly acceptable carrier.

56. A method of treating cardiovascular disease, fibrin containing blood clots, thrombus, plaques, or tumors which comprises administering to a patient in need thereof a therapeutic effective amount of the compound 39 of claim 49 complexed with a therapeutic isotope, in a pharmaceutically or veterinarily acceptable carrier.

57. The compound of claim 1, wherein two such compound together form a dimer through their $R_2$ substituents.

58. A dimer comprising two compounds of claim 1 linked at their $R_2$ substituents, optionally via amide bond formation.

59. A multimer comprising two or more compounds of claim 1 linked at their $R_2$ substituents optionally by having a polyamine or polyacid for the attachment of the alkyl acid or alkyl amine of $R_2$.

60. A compound of the formula:

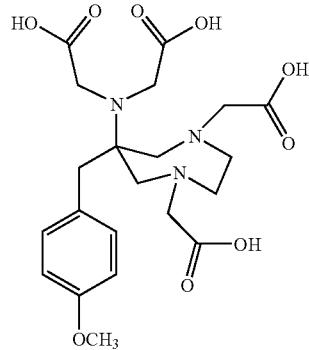

optionally complexed with a metal.

\* \* \* \* \*